United States Patent
Skinhoj

[11] Patent Number: 6,159,501
[45] Date of Patent: Dec. 12, 2000

[54] MODIFIED RELEASE MULTIPLE-UNITS DOSAGE COMPOSITION FOR RELEASE OF OPIOID COMPOUNDS

[75] Inventor: Annette Skinhoj, Rodovre, Denmark

[73] Assignee: Nycomed Danmark A/S, Denmark

[21] Appl. No.: 09/051,964

[22] PCT Filed: Mar. 7, 1997

[86] PCT No.: PCT/DK97/00101

§ 371 Date: Jun. 22, 1998

§ 102(e) Date: Jun. 22, 1998

[87] PCT Pub. No.: WO97/32573

PCT Pub. Date: Sep. 12, 1997

[30] Foreign Application Priority Data

Mar. 8, 1996 [DK] Denmark .................................. 0278/96
Dec. 20, 1996 [DK] Denmark .................................. 1466/96

[51] Int. Cl.[7] .......................... A61K 9/54; A61K 31/485; A61K 9/62
[52] U.S. Cl. .......................... 424/461; 424/494; 424/490; 424/489; 424/451; 424/456; 424/457; 424/458; 424/459
[58] Field of Search .................... 424/456, 457, 424/459, 460, 461, 462, 489, 490, 492, 493, 458, 494

[56] References Cited

U.S. PATENT DOCUMENTS

| | | |
|---|---|---|
| 4,797,410 | 1/1989 | El-Fakahany . |
| 5,330,766 | 7/1994 | Morella . |
| 5,411,745 | 5/1995 | Oshlack et al. . |
| 5,470,584 | 11/1995 | Hendrickson et al. . |
| 5,478,577 | 12/1995 | Sackler et al. . |
| 5,520,931 | 5/1996 | Persson et al. . |
| 5,549,912 | 8/1996 | Oshlack et al. . |
| 5,601,842 | 2/1997 | Bartholomaeus . |
| 5,672,360 | 9/1997 | Sackler et al. . |

FOREIGN PATENT DOCUMENTS

| | | |
|---|---|---|
| 0 282 698 | 9/1988 | European Pat. Off. . |
| 0 605 174 A1 | 7/1994 | European Pat. Off. . |
| 2170210A | 7/1986 | United Kingdom . |
| 88/06893 | 9/1988 | WIPO . |
| 95/14460 | 6/1995 | WIPO . |

*Primary Examiner*—Thurman K. Page
*Assistant Examiner*—Brian K. Seidleck
*Attorney, Agent, or Firm*—Peter F. Corless; Dike, Bronstein, Roberts, & Cushman, LLP

[57] ABSTRACT

An oral pharmaceutical modified release multiple-units composition for the administration of an analgesically effective amount of an opoid. The composition comprises at least two fractions wherein individual units containing an opoid are coated with a sustained release coating. A first fraction is adapted to relatively fast release while a second fraction is adapted to a delayed release. Such compositions make possible to obtain both a relatively fast onset of the analgesic effect and the maintenance of analgesically active plasma concentration for a relatively long period of time. The invention further relates to a process for the preparation of a composition according to the invention.

82 Claims, 26 Drawing Sheets

Effect evaluation, Patients treatment preference
Intent-to-treat Population

MODIFIED RELEASE MULTIPLE-UNITS DOSAGE COMPOSITION FOR RELEASE OF OPIOID COMPOUNDS

This application is a 371 PCT/DK97/00101 filed Mar. 7, 1997.

The present invention relates to an oral pharmaceutical modified release multiple-units dosage composition for the administration of an analgesically effective amount of an opioid to obtain both a relatively fast onset of the analgesic effect and the maintenance of an analgesically active plasma concentration for a relatively long period of time. The modified release multiple-units dosage composition comprises at least two fractions wherein individual units containing an opioid are coated with a sustained release coating designed to release the active ingredient in such a manner that both a relatively fast onset of the analgesic effect and the maintenance of an analgesically active plasma concentration for a relatively long period of time are obtained, the composition thereby being adapted to once- or twice-a-day administration.

TECHNICAL BACKGROUND

Drug levels can be maintained above the lower level of the therapeutic plasma concentration for longer periods of time by giving larger doses of conventionally formulated dosage forms. However, it is not a suitable approach to increase dosage as such doses may produce toxic and undesired high drug levels. Alternatively, another approach is to administer a drug at certain intervals of time, resulting in oscillating drug levels, the so-called peak and valley effect. This approach is generally associated with several potential problems, such as a large peak (toxic effect) and valley (non-active drug level) effect, and a lack of patient compliance leading to drug therapy inefficiency or failure. If, however, the plasma concentration is kept constant over the therapeutic level using conventional tablets, an unacceptably high daily dosage is required if the opioid is not administered very frequently.

Controlled release preparations are known which are designed to rapidly release a fraction of a total drug dose. This loading dose is an amount of a drug which will provide a desired pharmacological response as promptly as possible according to the biopharmaceutical properties of the drug. Such formulations which initially release a burst of a therapeutic agent and then release the agent at an essentially constant rate are described in WO 95/14460 published on Jun. 1, 1995. The composition described therein relates to a sustained release opioid formulation comprising a plurality of substrates comprising the active ingredient in a sustained release matrix or coated with a sustained release coating comprising a retardant material. The sustained release beads are then coated with an opioid in immediate release form or, in the case the composition is in the form of a gelatine capsule, the plain opioid is incorporated into the gelatin capsule via inclusion of the sufficient amount of immediate release opioid as a powder or granulated within the capsule. In a further alternative, the gelatine capsule itself is coated with an immediate release layer of the opioid.

A major disadvantage of the above formulation is that the incorporation of the plain opioid in gelatine capsules without a protecting coating on the opioid may easily result in lack of control of the exact dosage, especially if the capsule leaks or the patient breaks the capsule. In addition it is not possible to modify the release in relation to the sustained release fraction, and the only possibility of avoiding toxic plasma concentrations, or controlling the peak plasma concentration, is to decrease the exact amount of opioid of the immediate release portion.

The above-mentioned controlled release preparations are long-acting and release the drug in a sustained manner. However, these types of formulations may result in an undesirable decreased bioavailability, probably because the active ingredient is not released in due time.

Multiple-units formulation techniques according to the invention aim at a modified release of active substance in a predetermined pattern to reduce and delay the peak plasma concentration without affecting the extent of drug availability. The frequency of undesirable side effects may be reduced, and due to the delay in the time it takes to obtain the peak plasma concentration and the prolongation of the time at the therapeutically active plasma concentration, the frequency of the administration may be reduced to a dosage taken only twice or once a day. This also serves to improve patient compliance. A further advantage of the modified release multiple-units dosage form is that high local concentrations of the active substance in the gastrointestinal system are avoided, due to the units being distributed freely throughout the gastrointestinal tract, independent of emptying.

Moreover, patients suffering from chronic pains very often require high daily dosages of analgesic, e.g. about 100 mg of morphine. If such high dosage of an opioid should be given once a day, the release from the dosage form must be safe. The formulation should also be very storage stable because an immediate release due to accidental damaging of e.g. the coating or capsule of a high dosage form may result in undesired high plasma concentrations, so-called dose dumping, which could cause the death of the patient. By use of a coated multiple unit dosage form, the risk of dose dumping due to e.g. rupturing of a coating is reduced because the amount of active ingredient in each coated unit is negligible.

However, a major disadvantage of the once-a-day treatment in the art may be a low peak plasma concentration at the end of the day and thereby the lack of pain relief. As the treatment of pain is a balance of pain relief on the one hand and the risk of side effects on the other hand, e.g. due to accumulation of drug, the dosage interval is generally calculated so that the drug concentration is substantially decreased at the time of intake of the next dosage. Accordingly, the patient will very often suffer from increasing pain before the drug concentration subsequent to the next dosage has reached the therapeutic level. In addition, it should be noted that in the treatment of pain, relatively higher dosages, corresponding to a relatively higher peak concentration, are often needed in case the pain breaks through. Accordingly, a relatively higher initial plasma concentration of analgesic may be necessary compared to the plasma concentration which is capable of maintaining a state of pain relief.

As treatment of chronic pains very often involves a life-long treatment, and thereby involves high cost, once-a-day dosage forms should not imply an expensive and complicated production method, as a higher cost of such a product compared to the cost for the conventional products would indeed interfere with the success of the drug.

However, no oral analgesic pharmaceutical composition has been disclosed which at the same time can be produced in an easy, cheap and reliable manner and which provides a suitable profile for release of active substance resulting in an extended period of action so that pain is both rapidly alleviated after administration and avoided for a period of about 12 to 24 hours.

Therefore, there is a need of a formulation comprising an opioid substance permitting the administration of large as well as small, daily dosages only once or twice a day in a safe and reliable manner, and which is easy to produce, preferably involving conventional production methods and as few product steps as possible. It is also important that an opioid formulation for daily administration comprises the active ingredient in such a way that the formulation has a reliable dissolution rate since unexpected fast dissolution of the opioid could be dangerous for the patient.

BRIEF DISCLOSURE OF THE INVENTION

The purpose of the present invention is to provide an oral modified release multiple-units formulation for administration of a daily dosage of an opioid in a dosage form which only requires administration at the most twice daily, preferably once daily, and which overcomes the drawbacks of hitherto suggested formulations of modified release formulations in that the dosage form both provides a substantially fast release from a first fraction comprising modified release multiple units and a delayed and extended release from a second fraction of modified release multiple units of the opioid whereby alleviation of pain is achieved shortly after administration and is maintained for at least 12 hours, preferably 24 hours after administration.

A further aspect of the invention is to provide a process for the preparation of a composition of an oral pharmaceutical modified release multiple-units dosage composition, and in addition, a method for treating patients with a composition according to the invention whereby the interval between each administration is increased to about 12–24 hours.

Accordingly, the present invention relates to an oral pharmaceutical modified release multiple-units formulation containing an opioid as the active substance, the formulation comprising a dosage unit which contains at least two distinct fractions of multiple units having modified release properties, the construction of each fraction with respect to the modified release therefrom and the ratio between the fractions being adapted so as to obtain i) a relatively short duration uptake of part of the opioid resulting in an analgesically active plasma concentration within a relatively short period of time and derived from one fraction of the multiple units, and ii) a reduced and delayed peak plasma concentration resulting in the maintenance of an analgesically active plasma concentration for a relatively long period of time and derived from another fraction of the multiple units.

The modified release multiple-units dosage forms of the present invention achieve and maintain therapeutic levels and, at the same time, limit the concurrent side effects, such as nausea, vomiting or drowsiness, which are believed to be associated with high blood levels of opioid analgesics. It is also believed that the use of the present dosage forms leads to a reduced risk of drug addiction compared with conventional therapy. Furthermore, the modified release multiple-units dosage forms of the present invention preferably release the opioid analgesic at a rate that is independent of pH whereby pH-dependent "dose dumping" upon oral administration is avoided.

Since also the first relatively fast fraction of the formulation according to the invention comprises the opioid in a coated form, the release of the fraction can be modified to the desired release profile which is of great importance for the safety of the drug. First of all, "free opioid" in a capsule or on a coating which may be subject to degradation or leaking from the formulation is avoided.

As the coating of each fraction may be performed with substantially identical procedures and materials, the production cost can be kept on a low level.

DETAILED DISCLOSURE OF THE INVENTION

Accordingly, the present invention relates to an oral pharmaceutical modified release multiple-units composition for the administration of an analgesically effective amount of an opioid to obtain both a relatively fast onset of the analgesic effect and the maintenance of an analgesically active plasma concentration for a relatively long period of time, a unit dosage of the composition comprising at least two fractions of multiple units as follows:

a first fraction of coated modified release multiple units for relatively fast release in vivo of an opioid to obtain a therapeutically active plasma concentration within a relatively short period of time, and a second fraction of coated modified release multiple units for delayed release in vivo of an opioid to maintain an analgesically active plasma concentration for a period of at least 12 hours, the formulation of the first and the second fractions, with respect to modified release therefrom and with respect to the ratio between the first and the second fraction in the unit dosage, being adapted so as to obtain:

i) a relatively fast in vitro release of the opioid from the first fraction of modified release multiple units, as measured by the dissolution method III as described below in the paragraph "Materials and Methods", ii) a delayed in vitro release from the second fraction of modified release multiple units relative to the in vitro release of the first fraction of the opioid, as measured by the dissolution method III as described in the specification, the fast release and the delayed in vitro release being adapted so that the first fraction is substantially released when the release from the second fraction is initiated corresponding to at least 50% release of the first fraction at the time when 10% of the second fraction is released as measured by the dissolution method III described herein.

In one embodiment the composition may comprise modified release multiple units wherein the in vitro dissolution characteristics of the first fraction of modified release multiple-units within 0.5 hour provides a release as defined by the dissolution method III described herein of at least 30%, such as at least 40%, preferably at least 50%, more preferred at least 60%, even more preferred at least 70%, most preferred at least 90%.

In addition, the composition may comprise modified release multiple units wherein the in vitro dissolution characteristics of the first fraction of modified release multiple units within 1 hour provides a release as defined by the dissolution method III described herein of at least 50%, such as at least 60%, preferably at least 70%, more preferred at least 80%, even more preferred at least 90%, most preferred at least 95%.

The in vitro dissolution characteristics of the second fraction of modified release multiple units may in one embodiment within 1 hour provide a release as defined by the dissolution method III described herein in the range of 0%–30%, such as in the range of 0%–20%, preferably in the range of 0%–10%, most preferred about 5%.

Furthermore, the in vitro dissolution characteristics of the second fraction of modified release multiple units may within 3 hours provide a release as defined by the dissolution method III described herein in the range of 10%–70%, such as in the range of 15%–60%, preferably in the range of 20%–50%, more preferred in the range of 25%–45%, most preferred about 35%.

Within 6 hours, the in vitro dissolution characteristics of the second fraction of modified release multiple units may provide a release as defined by the dissolution method III described herein in the range of 35%–95%, such as in the range of 50%–90%, preferably in the range of 60%–80%, more preferred in the range of 65%–75%, most preferred about 70%.

In addition, within 9 hours the in vitro dissolution characteristics of the second fraction of modified release multiple units may provide a release as defined by the dissolution method III described herein in the range of 50%–100%, such as in the range of 60%–98%, preferably in the range of 70%–95%, more preferred in the range of 80%–90%, most preferred about 85%.

To ensure that the release of the second fraction has the desired time lag relative to the release of the first fraction, the in vitro dissolution characteristics of the first and second fractions are in one embodiment adapted so that the first fraction is substantially released when the release from the second fraction is initiated, corresponding to at least 50% release of the first fraction at the time 5% of the second fraction is released, as measured by the dissolution method III described herein. In addition, the in vitro dissolution characteristics of the first and second fractions in the same or a second embodiment as mentioned above are adapted so that the first fraction is substantially released when the release from the second fraction is initiated, corresponding to at least 70% release of the first fraction at the time 10% of the second fraction is released, as measured by the dissolution method III described herein.

The two fractions of modified multiple units may be selected, with respect to the modified release from each fraction and the ratio between the two fractions, so that the in vitro dissolution characteristics of the composition within 1 hour provide a release of the opioid in the first and second fractions in the range of 5%–50%, such as in the range of 5%–45%, preferably in the range of 15%–40%, most preferred in the range of 20%–35% such as about 27%, as defined by the dissolution method V described herein.

In addition, the two fractions of modified multiple units may be selected, with respect to the modified release from each fraction and the ratio between the two fractions, so that the in vitro dissolution characteristics of the composition within 3 hours provide a release as defined by the dissolution method V described herein in the range of 20%–80%, such as in the range of 25%–70%, preferably in the range of 30%–60%, most preferred in the range of 35%–55% such as about 50%.

In an additional aspect, the two fractions of modified multiple units may be selected, with respect to the modified release from each fraction and the ratio between the two fractions, so that the in vitro dissolution characteristics of the composition within 6 hours provide a release as defined by the dissolution method V described herein in the range of 40%–98%, such as in the range of 50%–95%, preferably in the range of 60%–90%, more preferred in the range of 65%–85%, most preferred in the range of 70%–83% such as about 80%.

Furthermore, the two fractions of modified multiple units may be selected, with respect to the modified release from each fraction and the ratio between the two fractions, so that the in vitro dissolution characteristics of the composition within 9 hours provide a release as defined by the dissolution method V described herein in the range of 50%–100%, such as in the range of 60%–99%, preferably in the range of 70%–98%, more preferred in the range of 75%–97%, most preferred in the range of 80%–95% such as in the range 85%–96%, such as about 95%.

In a preferred embodiment, the composition fulfils the above criteria with respect to the dissolution characteristics of the composition in the full time span mentioned.

The ratio between the first and the second fractions of modified release multiple units in the composition according to the invention may be in the range of 1:20–1:2, such as in the range of 1:10–1:3, preferably in the range of 1:8–1:3, more preferred in the range of 1:7–1:3.5, even more preferred in the range of 1:3.5–1:4.5, and most preferred in the range of 1:4.

In a preferred embodiment, the multiple units are coated, cross-sectionally substantially homogeneous pellets.

The individual units of the first and second fractions differ with respect to modified release properties, e.g. due to the amount of coating applied to each of the multiple-units of each fraction. However, the individual units of the two fractions are preferably of substantially the same size.

It is preferred that the modified multiple units of the first fraction result in a peak plasma concentration of opioid which is substantially the same as the peak concentration resulting from the second fraction. As the peak plasma concentration of the second fraction is adapted so that the peak has a prolonged character due to the dissolution characteristics of the fraction described herein, the peak of this second fraction should preferably substantially represent the lower level of the therapeutic plasma concentration. In this preferred embodiment, the plasma concentration level is of such a size that no opioid is in excess.

Since the total amount of opioid contained in the first fraction is generally relatively small (e.g. about 20%) compared to the total opioid of the composition, a peak plasma concentration of opioid derived from the first fraction which is higher than the peak concentration resulting from the second fraction does not necessarily represent a substantial waste of opioid.

However, unless the patient suffers from heavy breakthrough pain wherein a higher plasma concentration than the plasma concentration for maintaining pain alleviation often seems to be needed, the peak of the first fraction should not exceed the peak from the second fraction for a longer period of time.

Even in the circumstances wherein the peak of the first fraction is preferably higher than the peak from the second fraction, unsuitable high plasma concentrations (within the toxic level) derived from the first fraction may easily be avoided due to the modified release.

In another embodiment, e.g. in the circumstances wherein the patient is well treated by administration once or twice a day with the dosage composition according to the invention, the first fraction may be adapted so that it results in a peak plasma concentration of opioid which is lower than the peak concentration resulting from the second fraction. This would not necessarily result in breakthrough pain as opioid remaining in the plasma from the previous dosage administered may contribute to maintaining the plasma concentration sufficiently high until the second fraction of the composition is released. In other cases, the daily dosage may be administered at a suitable time of the day when the patient has experienced less need for the analgesic, e.g. before bedtime.

Accordingly, an important aspect of the invention is an embodiment wherein the first fraction results in a therapeutically active plasma concentration of opioid until the delayed release of an opioid from the second fraction of modified release multiple units contributes to the maintenance of a therapeutically active plasma concentration of opioid.

It is preferred that the modified release coating of each fractions comprises substantially the same coating components. The time lag of the release from the second fraction relative to the first fraction may be obtained by a modified release coating of the first fraction which is present in a range of about 10% to about 80%, calculated on the dry weight of the amount of the modified release coating of the second fraction.

It is also preferred that the modified release coating of the fractions is substantially water-insoluble, but water-diffusible and substantially pH-independent which will give an absorption independent of the presence of food in the stomach.

The amount of opioid of the modified release multiple-units composition according to the invention may be selected so that is corresponds to about 5 mg, 10 mg, 20 mg, 30 mg, 50 mg, 60 mg, 100 mg, 200 mg or 300 mg of morphine which are all dosages generally known in the art. However, the composition according to the invention preferably comprises an amount of an opioid which is a daily analgesically effective amount of the opioid.

Generally, with conventional dosage forms such as tablets comprising plain opioid, it is not always possible to obtain identical release profiles when different dosages are administered together as the load of active ingredient may differ depending on the size of the tablet. The release profile for 100 mg given in a single dosage may thus differ from 100 mg given as 5 dosages comprising 20 mg each. Not even with the commercially available modified release dosage forms, a substantially identical release profile within the different dosages is always observed.

With the composition according to the present invention, it is now possible to administer different dosages with identical release profiles. As long as each modified release multiple-units composition according to the invention is prepared with the same type of coated multiple units of the first and second fractions and in the same ratios, each of the dosage forms may be administered together to obtain any desired total dosage without altering the overall release profile from the total dosage. Accordingly, reliable and predictable plasma concentrations during the complete time span between administration may be obtained independently of the total dosage.

Therefore, a further advantage of the composition according to the invention is that the composition may be produced in different series of dosage forms of e.g. 10 mg, 30 mg, etc., each of the series having individual properties resulting from the design of modified release of the first and second fractions as well as from the ratio between the fractions. Any desired total dosage can then be selected from the relevant dosage forms within each of the series.

The preferred dosage form according to the invention is in the form of a capsule. The size of the capsule is adapted to the amount of opioid of the composition.

The above suggested dosage amounts should not be regarded as a limitation of the scope of the invention as it is obvious for the skilled person that any desired amount of opioid may be applied and is only limited by the size of the composition.

The overall goal of the present invention is to provide a unit dosage for the administration of an analgesically effective amount of an opioid only once a day. However, as some patients may still need to, or prefer to, receive administration twice a day, the invention should not be limited to a once-a-day unit dosage composition as long as each of the unit dosage compositions fulfils the criteria with respect to the dissolution mentioned above.

In a further aspect, the invention relates to a process for the preparation of a unit dosage of an oral pharmaceutical modified release multiple-units composition described above and in the examples, the process comprising incorporating into the unit dosage at least two fractions of coated multiple-units as follows:

a first fraction of coated modified release multiple units for relatively fast release in vivo of an opioid to obtain a therapeutically active plasma concentration within a relatively short period of time, and a second fraction of coated modified release multiple units for delayed release in vivo of an opioid to maintain an analgesically active plasma concentration for a period of at least 12 hours, the formulation of the first and the second fractions, with respect to modified release therefrom and with respect to the ratio between the first and the second fraction in the unit dosage, being adapted so as to obtain:

i) a relatively fast in vitro release of the opioid from the first fraction of modified release multiple units, as measured by the dissolution method III as described in the specification, ii) a delayed in vitro release from the second fraction of modified release multiple units relative to the in vitro release of the first fraction of the opioid, as measured by the dissolution method III as described in the specification, the fast release and the delayed in vitro release being adapted so that the first fraction is substantially released when the release from the second fraction is initiated corresponding to at least 50% release of the first fraction at the time when 10% of the second fraction is released as measured by the dissolution method III described herein.

The term "modified multiple-units composition" used in the present context is defined as the release of the drug in such a rate that plasma concentration levels are maintained for the longest possible period above the therapeutic (the analgetically active) level, but below the toxic level.

The term "fraction" of multiple units in the present context refers to a part of the multiple units of a dosage unit. The fraction will generally differ from another fraction of multiple units of the dosage unit. Even though only two fractions have been defined, it is within the scope of the invention to have more than two fractions in one dosage unit. Accordingly, the dosage unit according to the invention comprises at least two distinct fractions.

The term "dosage unit" in the present context refers to one single unit, e.g. a capsule. A dosage unit represents a plurality of individual units which in accordance with the general state of the art may be in the form of a capsule, a tablet, a sachet, etc.

The term "opioid" is used here to designate a group of drugs that are, to varying degrees, opium- or morphine-like in their properties. The term includes natural and synthetic opioids as well as active metabolites such as morphine-6-glucuronide and morphine-3-glucuronide, and mixtures of opioids. Pharmaceutically acceptable salts and/or complexes of opioids are also within the definition of opioids.

Further relevant examples of opioids include alfentanil, allylprodine, alphaprodine, anileridine, benzylmorphine, bezitramide, buprenorphine butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocondone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, myrophine, nalbuphine, narceine, nicormorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, salts thereof, mixtures of any of the foregoing, mixed μ-agonists/antagonists, μ- and/or κ-agonists, combinations of the above, and the like.

The modified release opioid oral dosage form of the present invention preferably includes morphine as the therapeutically active ingredient in an amount corresponding to from 5 to about 800 mg of morphine sulphate by weight. Alternatively, the dosage form may contain molar equivalent amounts of morphine salts. In other preferred embodiments where the opioid analgesic is other than morphine, the dosage form contains an appropriate amount to provide a substantially equivalent therapeutic effect.

In general, the opioids are readily absorbed from the gastro-intestinal tract after oral administration. Many opioids, including morphine, are subject to a first-pass effect metabolism in the liver. Satisfactory analgesia in cancer patients has been associated with a very broad range of steady-state concentrations of morphine in plasma of 16–364 ng/ml (Goodman and Gilman's; The Pharmacological Basis of Therapeutics, 8th Edition 1990: p. 496). The half-life of morphine is about 1.5–2 hours, however, morphine is metabolized to active products such as morphine-6-glucuronide which has a longer half-life. The average duration of action for the first single dose of 10 mg of oral, i.m. or s.c. morphine is about 4–5 hours. Examples of dosages of other opioid analgesics providing approximately the same analgesic effect as 10 mg of morphine are well known in the art, see for instance Goodman and Gilman's; The Pharmacological Basis of Therapeutics, 8th Edition 1990: p. 497.

The term "bioavailability" designates the extent to which the drug is absorbed from the modified multiple-units composition.

In the present context the term "therapeutically active plasma concentration for a period of at least 12 (24) hours" includes the situation wherein the opioid administered has been metabolized to active products resulting in an analgetic effect for the stated period. Accordingly, the exact opioid as administered may not be directly detectable in the plasma in an amount generally regarded as the analgetically effective level.

The daily dosage for each patient is generally calculated on the accumulated dosages given orally p.n. (=when needed) during a few days. Accordingly, if the need for a specific opioid during a period of 48 hours has been 120 mg, the daily dosage is 60 mg irrespective of whether the administration reflects a specific pattern, such as a need for higher dosages during day time.

In one embodiment of the present invention, the first fraction of multiple units comprises an amount of opioid corresponding to about 25% to about 17% (between ¼ and ⅙) of the daily dosage. In patients which are satisfactorily treated on 4 daily dosages of a conventional non-sustained formulation, the first fraction may in one example contain an amount of opioid corresponding to 25% of the daily dosage. The second fraction may then contain the remaining 75% of the daily dosage.

However, a preferred amount of the first fraction may comprise 20% of the daily dosage and the second fraction 80% of the daily dosage.

In another embodiment of the present invention, the first fraction of multiple units comprises an amount of opioid corresponding to the amount of opioid necessary for obtaining an analgesic effect upon a first single oral dose of a conventional non-sustained formulation of the opioid.

The individual units of the multiple-units formulations according to the invention will normally be pellets or beads having a size (average diameter) of from about 0.1 to 2 mm. The most preferred pellet size is from 0.5 to 0.8 mm. The pellets or beads comprise a combination of active substance, the opioid and excipients. When the pellets or beads are not coated, the combination of the active substance and the excipients is referred to as a core.

In the present context, the term "cores which are cross-sectionally substantially homogeneous" designates cores in which the active substance is not confined to an exterior layer on the core body, in other words normally cores which, through the cross-section of the core body, contain substantially the same type of composition comprising minor particles containing active substance, in contrast to the non-pareil type of cores which each consists of an excipient body with active substance applied to its surface. From this definition, it will be understood that the cores which are cross-sectionally substantially homogeneous will normally consist of a mixture of active substance with excipient(s), this mixture will not necessarily be qualitatively or quantitatively homogeneous through the total cross-sectional area of the core but may show, e.g., a concentration gradient of the opioid substance or they may consist substantially solely of opioid substance. In the following specification and claims, such cores which are cross-sectionally substantially homogeneous will, for the sake of brevity, often simply be designated "cores".

It is contemplated that the core comprising the opioid substance in a substantially homogeneous form provides a more reproducible release of the active ingredient than compared to e.g. particles in which the active ingredient forms part of the coating.

It is preferred that the release profile of the core of the individual unit is substantially non-limiting with respect to the desired release of the coated pellet, e.g. that the core itself provides about 100% release within 1 hour, preferably within 45 minutes as measured in the in vitro dissolution test described in the Examples. However, pellet cores showing a slower release of the active substance are still within the scope of the invention.

The oral pharmaceutical modified release multiple-units formulation according to the invention will typically be a capsule containing a multiplicity of the units, typically more than 100, a sachet containing a multiplicity of the units, typically more than 1000, or a tablet made from a multiplicity of the units, typically more than 100, in such a manner that the tablet will disintegrate substantially immediately upon ingestion in the stomach into a multiplicity of individual units which are distributed freely throughout the gastro-intestinal tract.

In the present context the term "once daily"/"once-a-day" is intended to mean that it is only necessary to administer the pharmaceutical formulation once a day in order to obtain a suitable therapeutic and/or prophylactic response; however, any administration may comprise co-administration of more than one dosage unit, such as, e.g., 2–4 dosage units if the amount of active substance required may not be formulated in only one composition unit or if a composition unit of a minor size is preferred.

In agreement with the above-mentioned definition of "once daily"/"once-a-day", "twice daily"/"twice-a-day" is supposed to mean that it is only necessary to administer the pharmaceutical formulation at the most twice a day in order to obtain a suitable therapeutic and/or prophylactic response in the patient.

In this respect it is a substantial advantage of the composition according to the invention that the release profile of each of the dosage units is constant irrespective of the overall amount of active ingredient in the dosage unit as long as the ratios of the substantially identical pellets having "fast" and "slow" release are constant.

Irrespective of the above-mentioned definitions of "once" and "twice" daily, a dosage unit constructed to deliver the active ingredient after only one daily administration is preferred. However, due to individual circumstances some patients may need a new dosage after e.g. 12 or 18 hours if the patient e.g. has an abnormal absorption or bowel transit time. If the individual has a relatively fast bowel transit time, some of the active ingredient may be excreted before the full dosage is released, or may be released in the colon from which the absorption is decreased. A multiple unit pharmaceutical formulation according to the present invention is preferably formed as a unit dosage form which upon oral administration disintegrates into a multiplicity of individual units. The dosage unit form is preferably a solid dosage unit form such as, e.g., a capsule, or a sachet, especially in the form of capsules.

The actual load of the opioid in the pharmaceutical formulation according to the invention, i.e. the concentration in % w/w of the opioid calculated on the total weight of the pellet, may depend on the particular opioid employed in the formulation. When the load of the opioid in the individual pellets of the two fractions and the ratio of the two fractions for one dosage unit comprising e.g. 10 mg of morphine is identical with another dosage unit comprising e.g. 100 mg, the release profile for each of the dosages will be identical. Consequently, an individual total dosage can be administered to the patient by combining the relevant dosage units e.g. selected from 10, 30 and 100 mg of opioid without altering the overall release profile of the total amount of opioid administered.

Preferably, the pellets of the pharmaceutical formulation according to the invention comprise about 10% w/w or more of the opioid of the total weight of the pellet.

The formulations mentioned above may be prepared by conventional methods known in the art. The invention also relates to a method for preparing an oral pharmaceutical modified release multiple-units formulation. The process for the preparation of a unit dosage of an oral pharmaceutical modified release multiple-units composition comprises incorporating into the unit dosage at least two fractions of coated multiple-units as follows:

a first fraction of coated modified release multiple units for
relatively fast release in vivo of an opioid to obtain a therapeutically active plasma concentration within a relatively short period of time, and a second fraction of coated modified release multiple units for delayed release in vivo of an opioid to maintain an analgesically active plasma concentration for a period of at least 12 hours, the formulation of the first and the second fractions, with respect to modified release therefrom and with respect to the ratio between the first and the second fraction in the unit dosage, being adapted so as to obtain:

i) a relatively fast in vitro release of the opioid from the first fraction of modified release multiple units, as measured by the dissolution method III mentioned in the specification, ii) a delayed in vitro release of the opioid from the second fraction of modified release multiple units relative to the in vitro release of the first fraction of the opioid, as measured by the dissolution method III mentioned in the specification, the fast release and the delayed in vitro release being adapted so that the first fraction is substantially released when the release from the second fraction is initiated, corresponding to at least 50% release of the opioid contained in the first fraction at the time when 10% of the opioid contained in the second fraction is released as measured by the dissolution method III mentioned in the description.

In a further embodiment, the invention relates to a method for preparing an oral pharmaceutical modified release multiple-units formulation in which a) individual units containing an active substance are coated with an inner film-coating mixture comprising a film-forming substance, a first fraction of the individual units of the dosage form being coated with an amount of coating, calculated on dry weight, which corresponds to from about 10% to about 90% of the amount of coating, calculated on dry weight of the coating of a second fraction of the individual units of the dosage, b) the thus coated units are optionally provided with an outer film layer comprising a film-forming agent, c) a mixture of individual units of the first and second fraction are formulated in a dosage form in the desired ratio of the two fractions.

The film-forming agent of step b) may be so selected that adhesion between the units is prevented at elevated temperatures, the coated units are then subsequently heated to a temperature above 40° C., preferably not above 65–75° C., and thereby a continuous phase is formed in the inner film layer in homogeneous admixture with the film-forming substance. In some cases, this curing process may also take place before the outer coating layer is applied.

As mentioned above, the pellets comprising opioid employed in a pharmaceutical formulation according to the present invention are coated with a modified release coating. The modified release coating is applied on the pellets from a solution and/or suspension preferably in an aqueous solvent, but an organic coating composition may also be applied.

Examples of film-forming agents which are suitable for use in accordance with the present invention are agents selected from the group consisting of cellulose derivatives such as, e.g., ethylcellulose, cellulose acetate, cellulose propionate, cellulose butyrate, cellulose valerate, cellulose acetate propionate; acrylic polymers such as, e.g., polymethyl methacrylate; vinyl polymers such as, e.g., polyvinyl acetate, polyvinyl formal, polyvinyl butyryl, vinyl chloride-vinyl acetate copolymer, ethylene-vinyl acetate copolymer, vinyl chloride-propylene-vinyl acetate copolymer; silicon polymers such as, e.g., ladder polymer of sesquiphenyl siloxane, and colloidal silica; polycarbonate; polystyrene; polyester; coumarone-indene polymer; polybutadiene; and other high molecular synthetic polymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquer used in the form of an aqueous dispersion, such as that which is commercially available from Rohm Pharma under the tradename Eudragit®. In further preferred embodiments, the acrylic coating comprises a mixture of two acrylic resin lacquers commercially available from Rohm Pharma under the tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. Eudragit® RL/RS mixtures are insoluble in water and in digestive fluids. However, coatings formed from the same are swellable and permeable in aqueous solutions and digestive fluids. The Eudragit® RL/RS dispersions may be mixed together in any desired ratio in order to ultimately obtain a modified release formulation having a desirable dissolution profile. The most desirable modified release formulations may be obtained from a retardant coating based on Eudragit® NE 30D, which is a neutral resin having a molecular weight of 800,000.

The amount of coating applied is adapted so as to obtain a predetermined dissolution characteristic of the fraction of the composition. The percentage by weight of the modified release coating on the individual pellet will, for the fraction providing the extended duration of effect of the opioid substance, be at the most about 15% w/w on an average, such as, e.g. 12% w/w, preferably at the most about 10% w/w on an average, more preferred in the range of about 6% to 9% w/w on an average, based on the weight of the uncoated individual pellet. The amount of coating applied depends on the predetermined dissolution characteristics of the particular core composition and the desired release profile of the fraction. For the fraction providing a substantial immediate release of the opioid substance, the amount of coating may be at the most about 8% w/w on an average, such as at the most about 6% w/w, preferably at the most about 5 w/w on an average, preferably at the most about 4% w/w such as about 3,5% w/w, preferably about 3% w/w on an average, based on the weight of the uncoated individual pellet.

However, the amount of coating applied should also be adapted so that there will be no rupturing problems.

The coating may be admixed with various excipients such as plasticizers, anti-adhesives such as, e.g., colloidal silicium dioxide, inert fillers, and pigments in a manner known per se.

Tackiness of the water-dispersible film-forming substances may be overcome by simply incorporating an anti-adhesive in the coating. The anti-adhesive is preferably a finely divided, substantially insoluble, pharmaceutically acceptable non-wetting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially water-insoluble calcium sulphates, colloidal silica, titanium dioxide, barium sulphates, hydrogenated aluminium silicates, hydrous aluminium potassium silicates and talc. The preferred anti-adhesive is talc. The anti-adhesive or mixture of anti-adhesives is preferably incorporated in the coating in an amount of about 0.1–70% by weight, in particular about 1–60% by weight, and preferably about 8–50% by weight of the inner film layer. By selecting a small particle size of the talc, a larger surface area is obtained; the consequent higher anti-adhesive effect makes it possible to incorporate smaller amounts of specific anti-adhesives.

The individual control release coated multiple-units may further comprise a second coating. Such coating may be adapted to stabilize the controlled release coated multiple-units and to prevent undesired changes of the release profile of each coated unit. Accordingly, the second lacquer or coating may contribute to stability of the release profile of the dosage unit.

It has surprisingly been found that if calcium is added to the second coating, e.g. in the form of calcium sulphate, an improved storage stability has been observed.

Accordingly, the multiple units may further comprise an outer film layer.

In one aspect, the outer second layer comprises a water-based film-forming agent which prevents adhesion between the units at elevated temperatures and imparts flowability to the units, the water-based film-forming agent being anti-adhesive at temperatures above about 40° C., especially temperatures above about 50° C., such as a temperature between about 60° C. and about 120° C., and being selected from diffusion coating materials such as ethylcellulose or enteric coating materials such as anionic poly(meth)acrylic acid esters, hydroxypropylmethylcellulosephthalate, celluloseacetatephthalate, polyvinylacetatephthalate, polyvinylacetatephthalate-crotonic acid copolymerisates, or mixtures thereof, or water-soluble coating materials such as water-soluble cellulose derivatives, e.g. hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose or hydroxypropylmethylcellulose.

Examples of plasticizers for use in accordance with the present invention include triacetin, acetylated monoglyceride, rape oil, olive oil, sesame oil, acetyl tributyl citrate, acetyl triethyl citrate, glycerin, sorbitol, diethyloxalate, diethylmalate, diethylmaleate, diethylfumarate, diethylsuccinate, diethylmalonate, dioctylphthalate, dibutylsebacetate, triethylcitrate, tributylcitrate, glyceroltributyrate, polyethyleneglycol, propyleneglycol, and mixtures thereof. The plasticizer is normally incorporated in an amount of less than 10% by weight, calculated on the dry matter content of the coating composition.

Apart from the active drug substance in the form of coated pellets, the pharmaceutical composition according to the invention may further comprise pharmaceutically acceptable excipients.

In the present context, the term "pharmaceutically acceptable excipient" is intended to denote any material which is inert in the sense that it substantially does not have any therapeutic and/or prophylactic effect per se. A pharmaceutically acceptable excipient may be added to the active drug substance with the purpose of making it possible to obtain a pharmaceutical formulation which has acceptable technical properties. Although a pharmaceutically acceptable excipient may have some influence on the release of the active drug substance, materials useful for obtaining modified release are not included in this definition.

Fillers/diluents/binders may be incorporated such as sucrose, sorbitol, mannitol, lactose (e.g., spray-dried lactose, α-lactose, β-lactose, Tablettose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tal® and Solka-Floc®), L-hydroxypropylcellulose (low-substituted) (e.g. L-HPC-CH31 and L-HPC-LH11), dextrins, maltodextrins (e.g. Lodex® 5 and Lodex® 10), starches or modified starches (including potato starch, maize starch and rice starch), sodium chloride, sodium phosphate, calcium phosphate (e.g. basic calcium phosphate), calcium sulfate, calcium carbonate. In pharmaceutical formulations according to the present invention, especially microcrystalline cellulose, L-hydroxypropylcellulose, dextrins, maltodextrins, starches and modified starches have proved to be well suited.

Disintegrants may be used such as cellulose derivatives, including microcrystalline cellulose; starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone° XL, Polyplasdone® XL-10); sodium carboxymethyl starch (e.g. Primogel® and Explotab®).

Other appropriate pharmaceutically acceptable excipients may include colorants, flavouring agents, surfactants, and buffering agents.

In the following examples, the invention is further disclosed.

BRIEF DESCRIPTION OF THE DRAWINGS

The terms "dissolution method III", "dissolution method V" and any such specified methods as used herein are defined to mean the same as those methods are specified in the examples below, particularly the MATERIALS AND METHODS section which follows.

Materials and Methods

Figure 1:
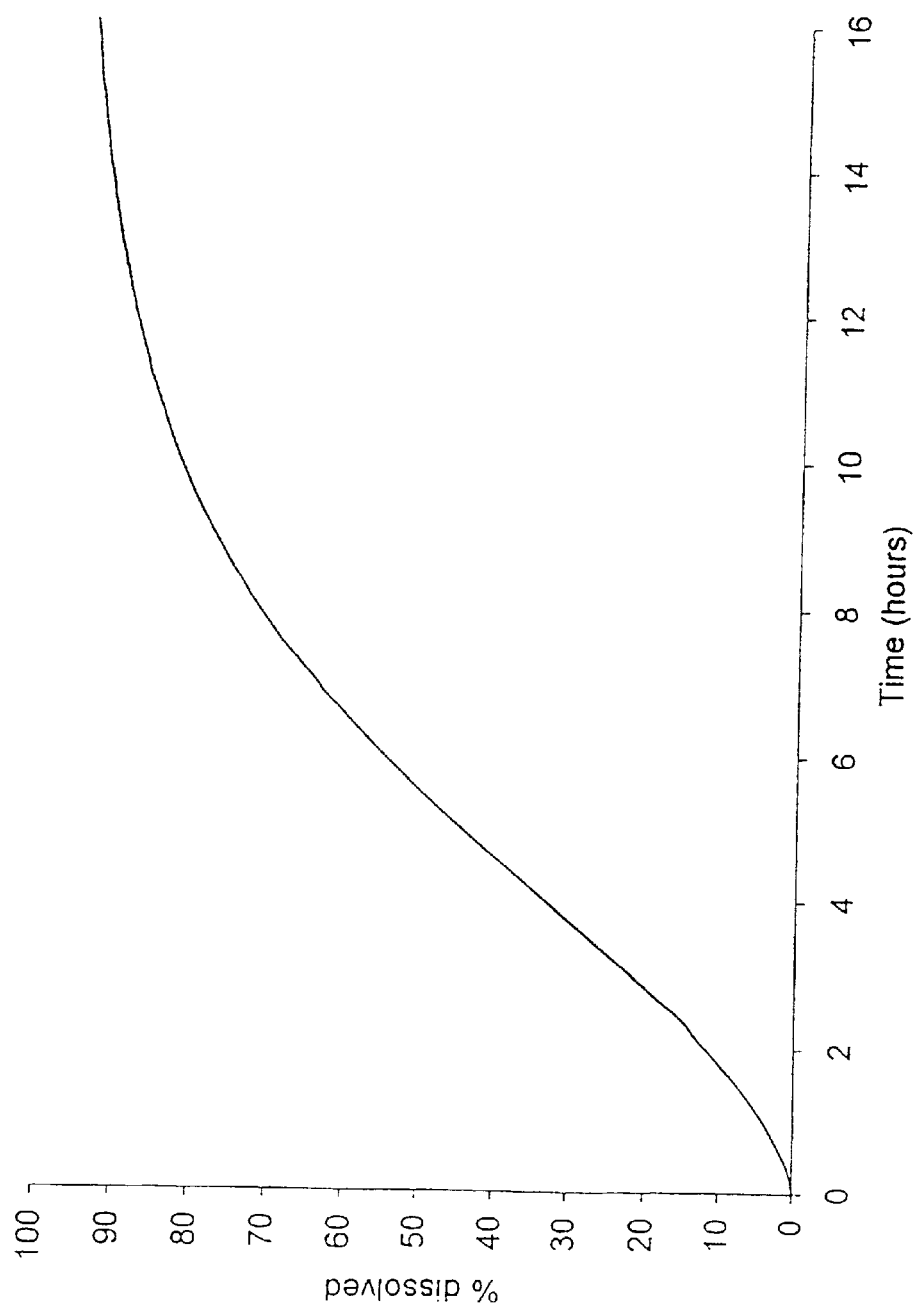
FIG. 1 shows a diagram of the release profile of the modified release coated cores prepared in accordance with Example 1.
Figure 2:
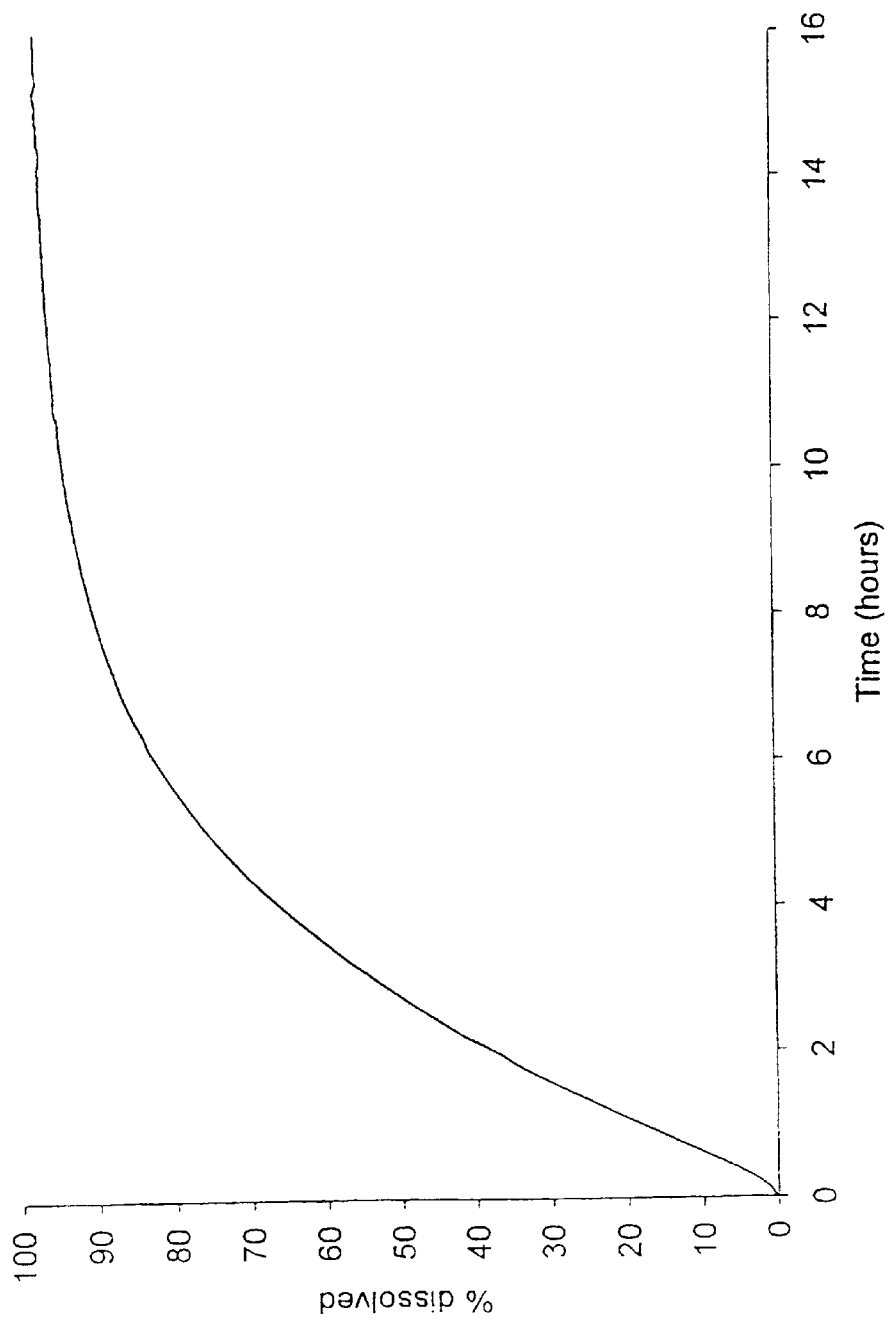
FIG. 2 shows a diagram of the release profile of the modified release coated cores prepared in accordance with Example 2.
Figure 3:
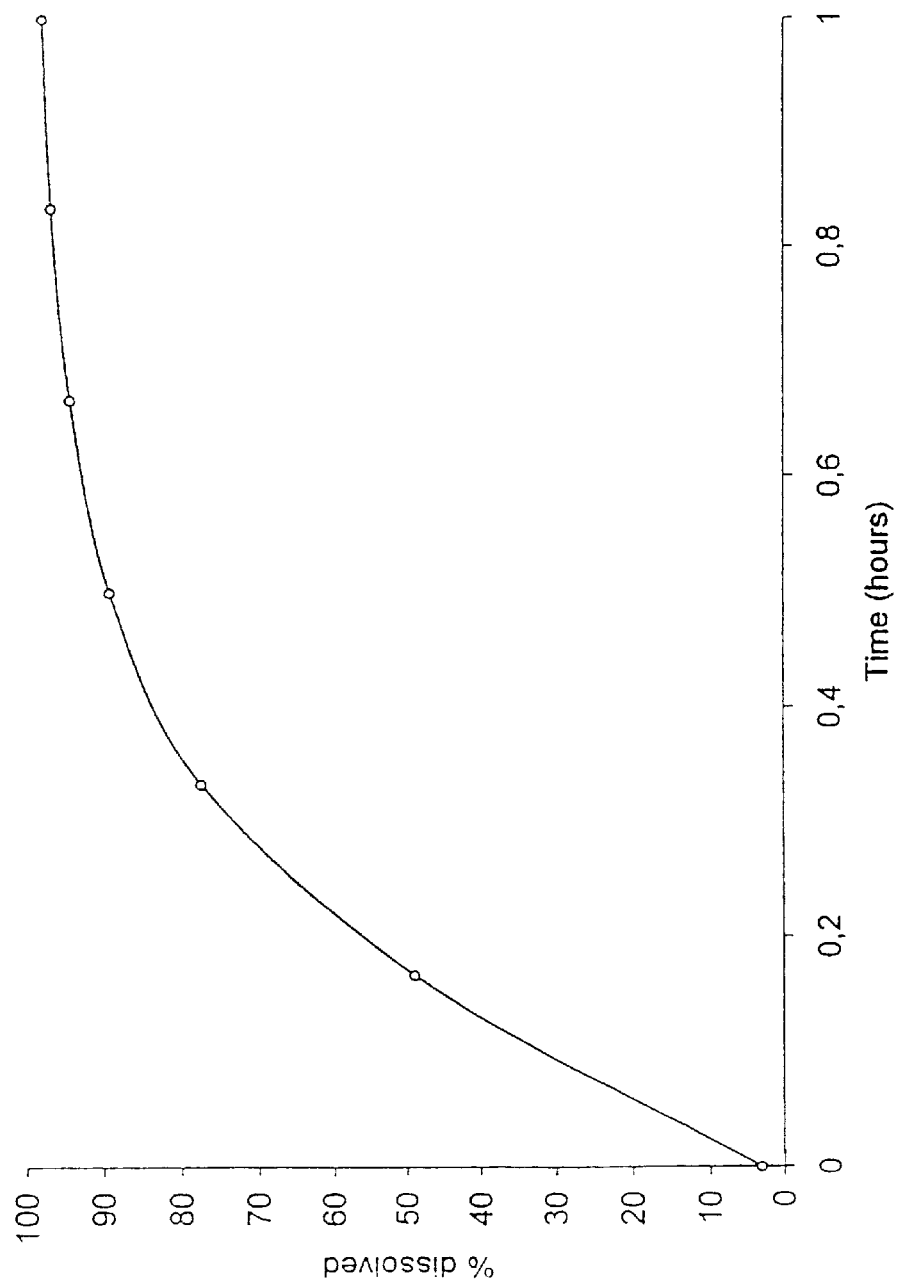
FIG. 3 shows a diagram of the release profile of the modified release coated cores prepared in accordance with Example 3.
Figure 4:
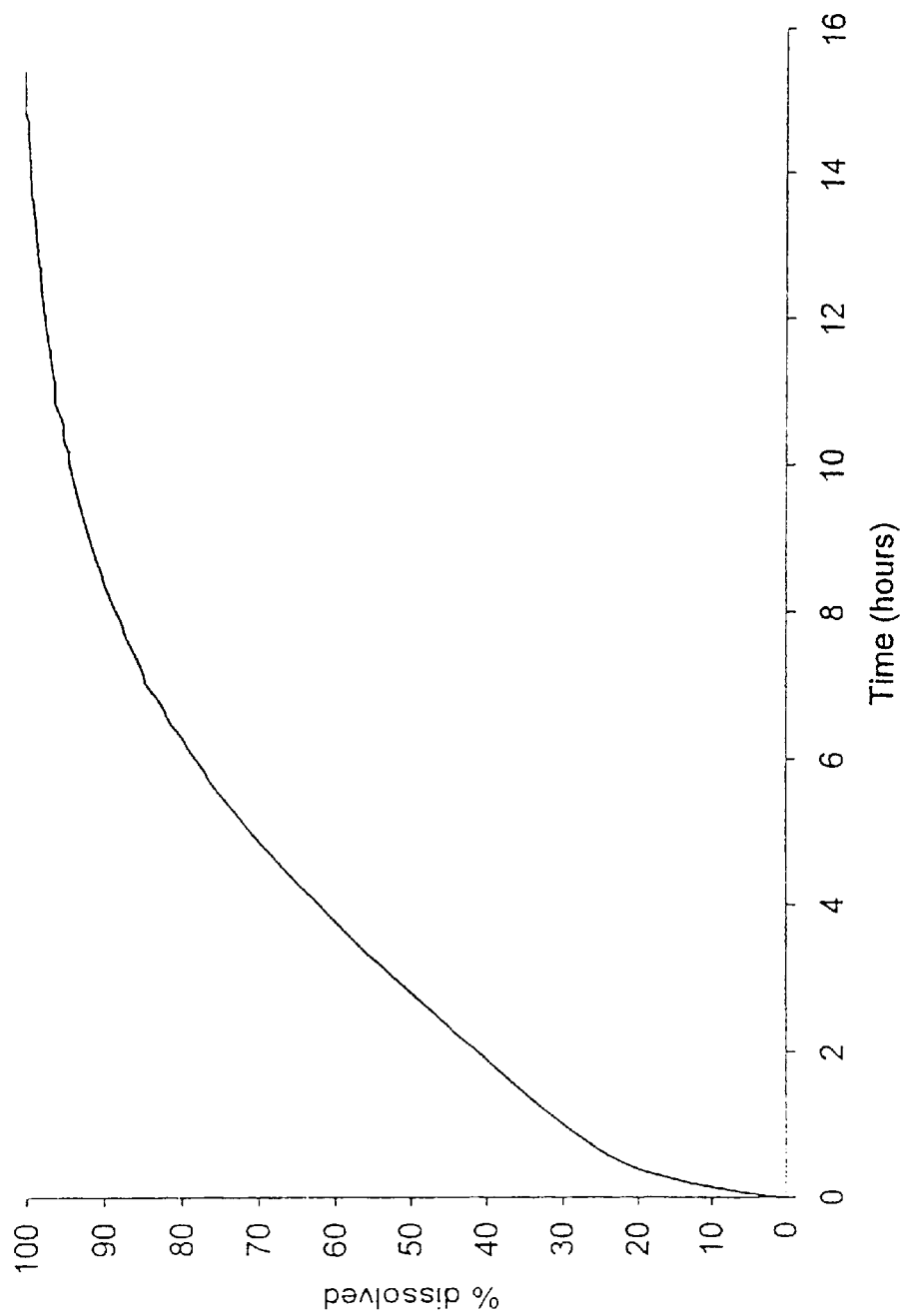
FIG. 4 shows a diagram of the release profile of the modified release coated cores prepared in accordance with Example 19.
Figure 5:
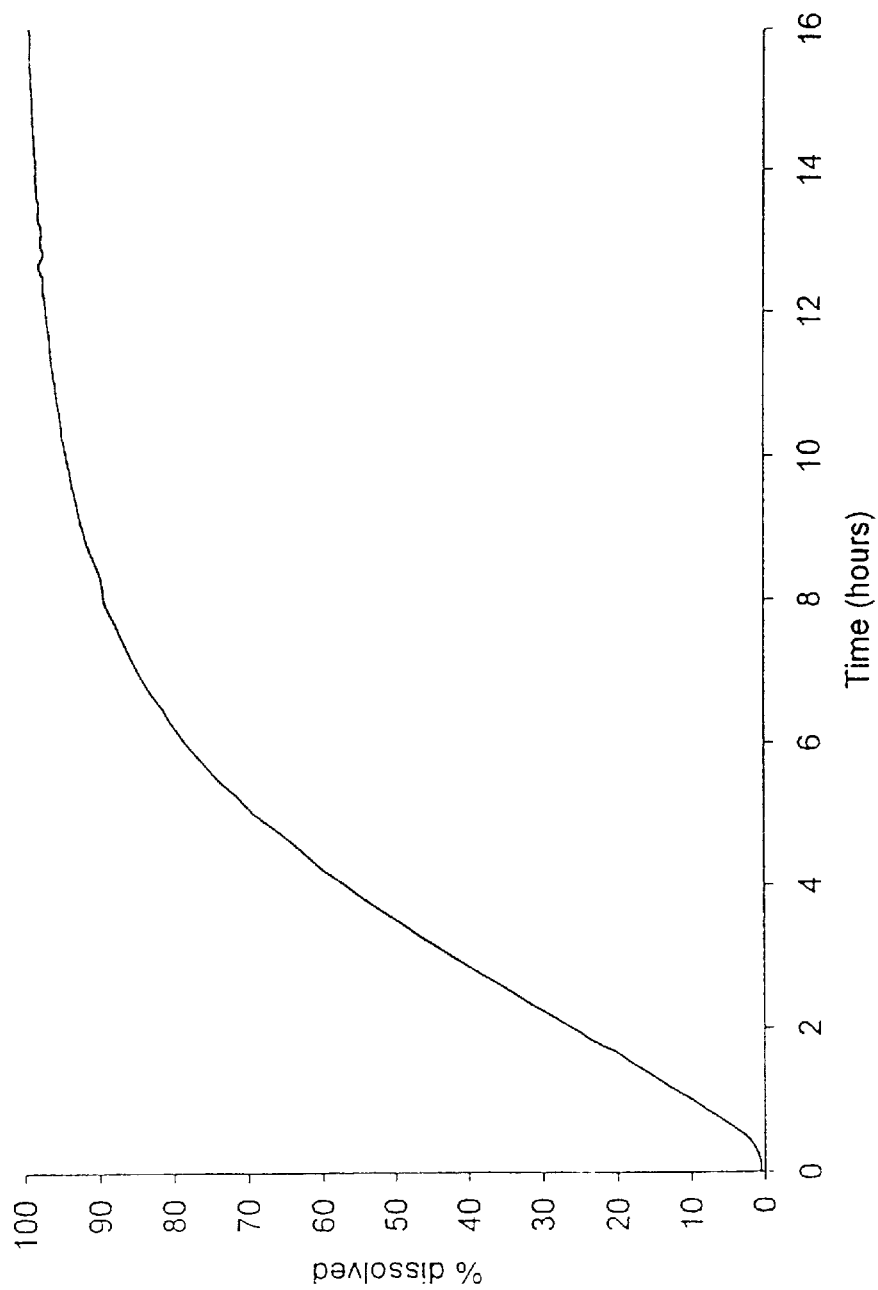
FIG. 5 shows a diagram of the release profile of the modified release coated cores prepared in accordance with Example 22, Batch No. 1.
Figure 6:
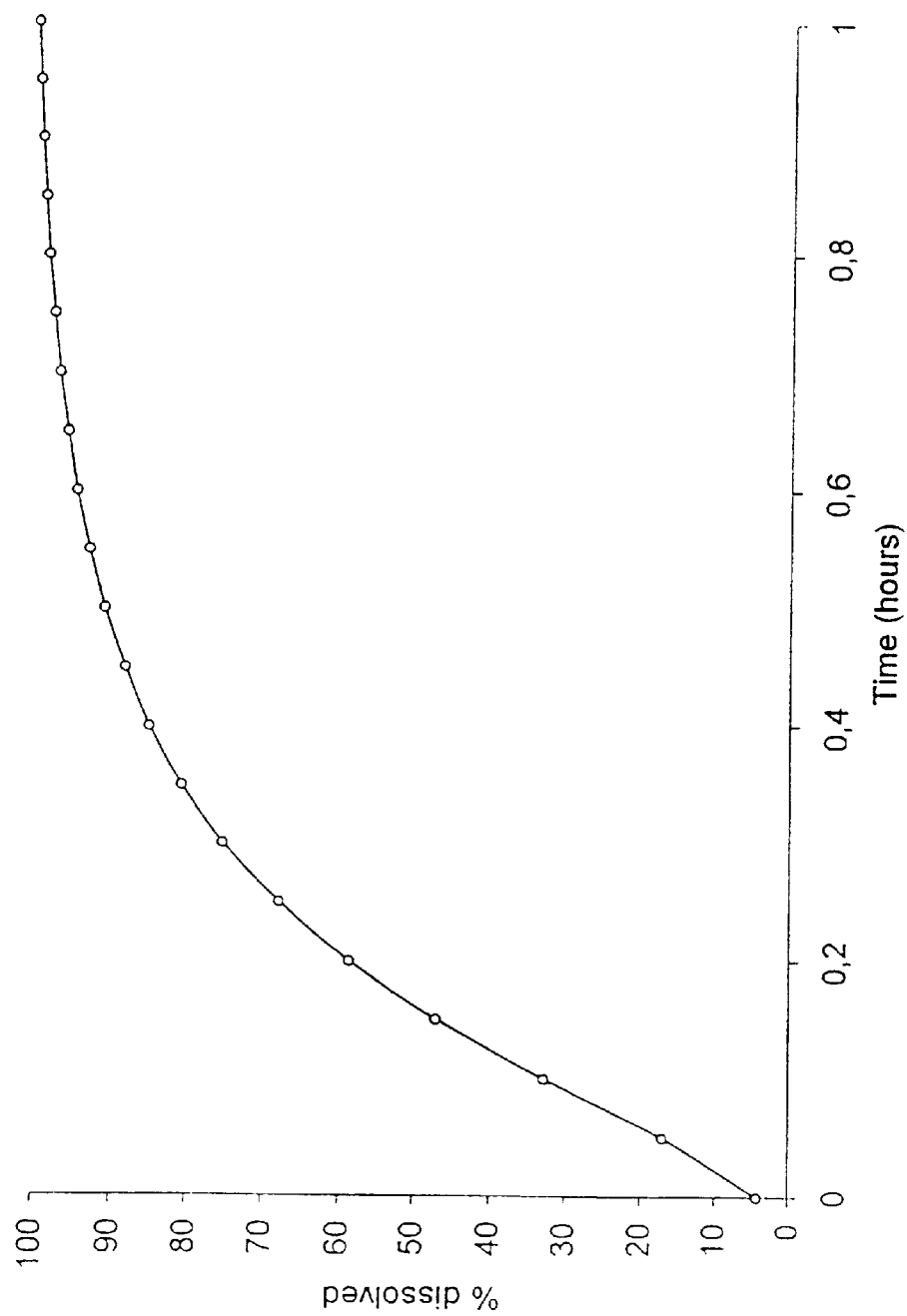
FIG. 6 shows a diagram of the release profile of the modified release coated cores prepared in accordance with Example 22, Batch No. 2.
Figure 7:
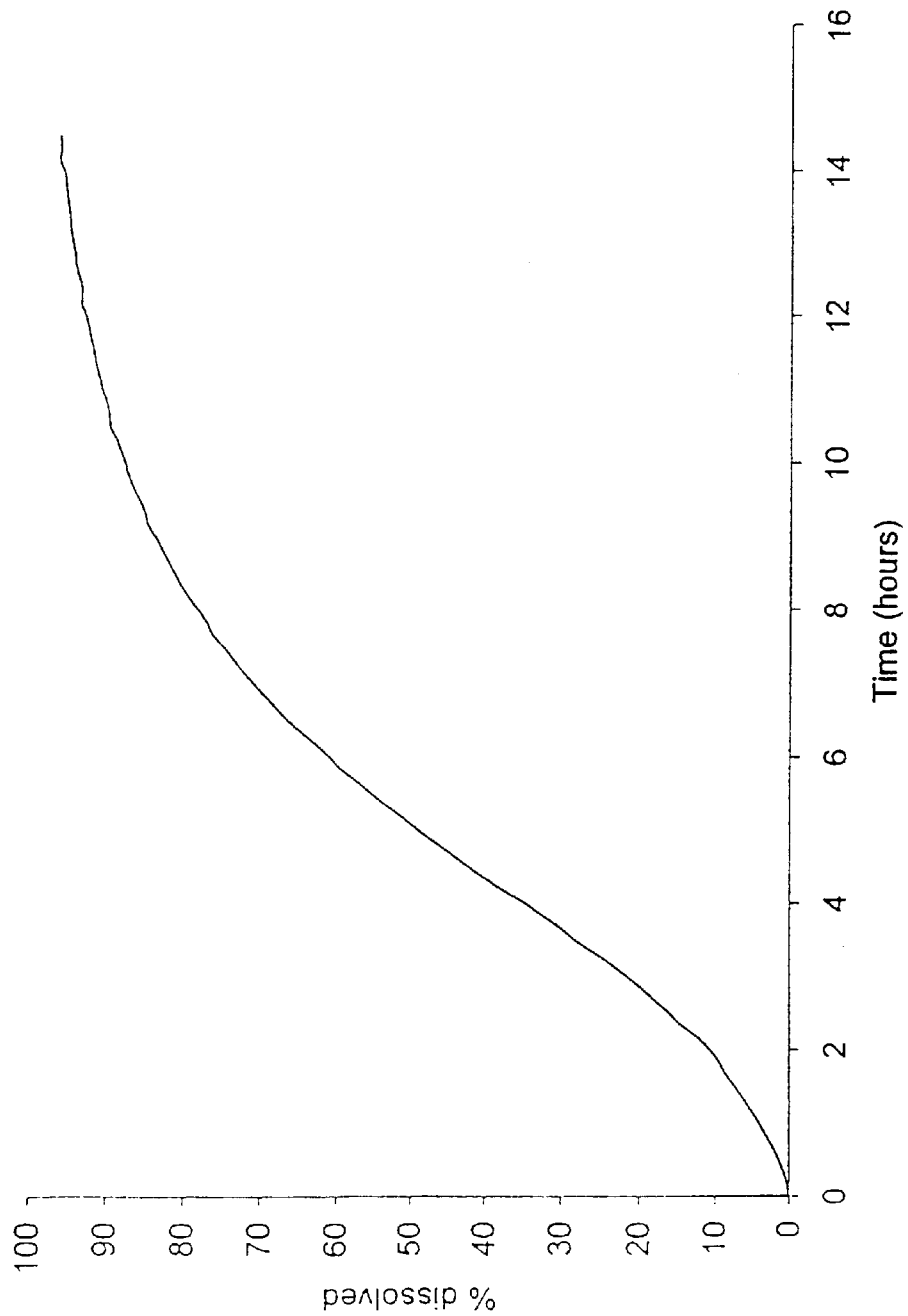
FIG. 7 shows a diagram of the release profile of the modified release coated cores prepared in accordance with Example 22, Batch No. 3.
Figure 8:
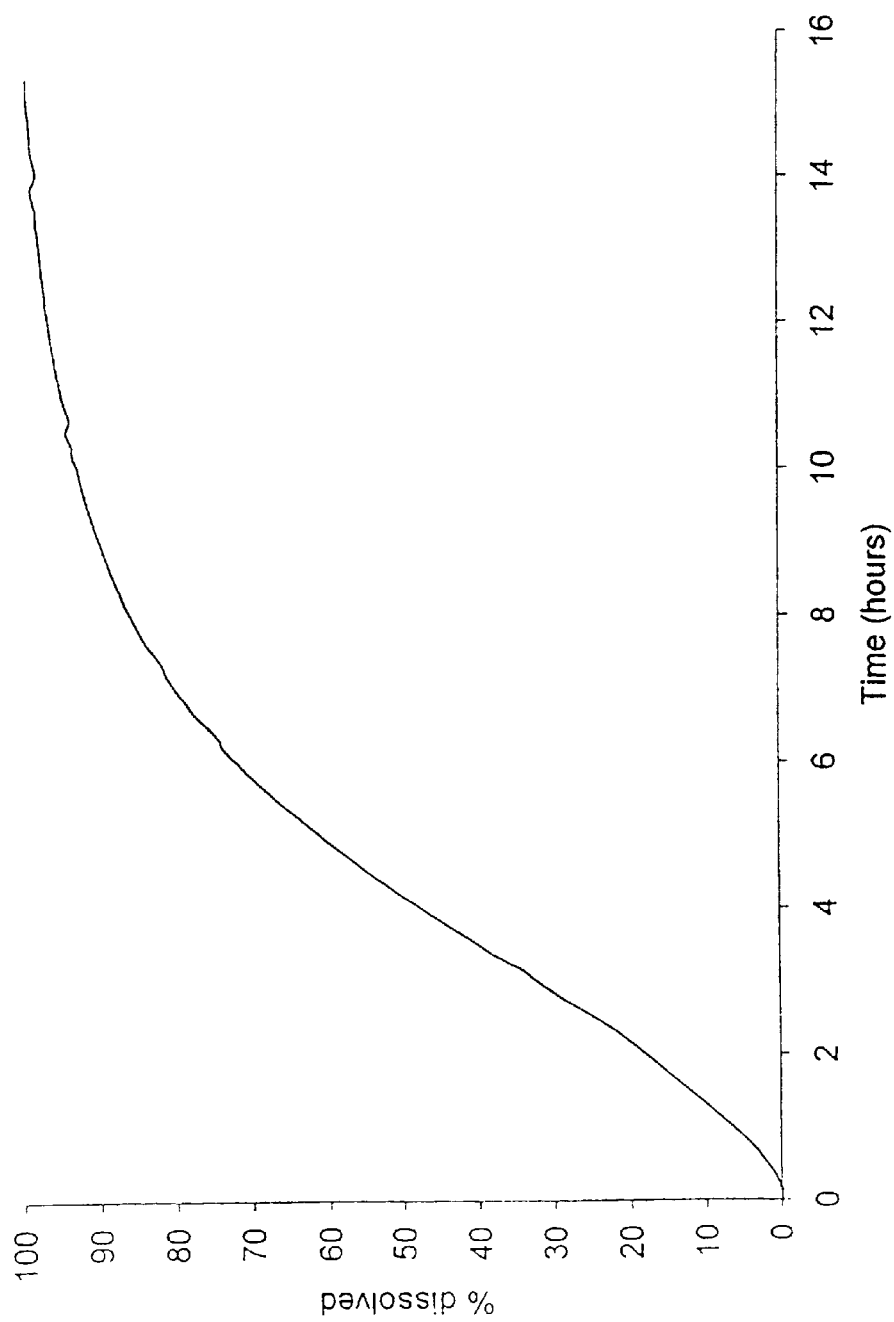
FIG. 8 shows a diagram of the release profile of the modified release coated cores prepared in accordance with Example 22, Batch No. 4.
Figure 9:
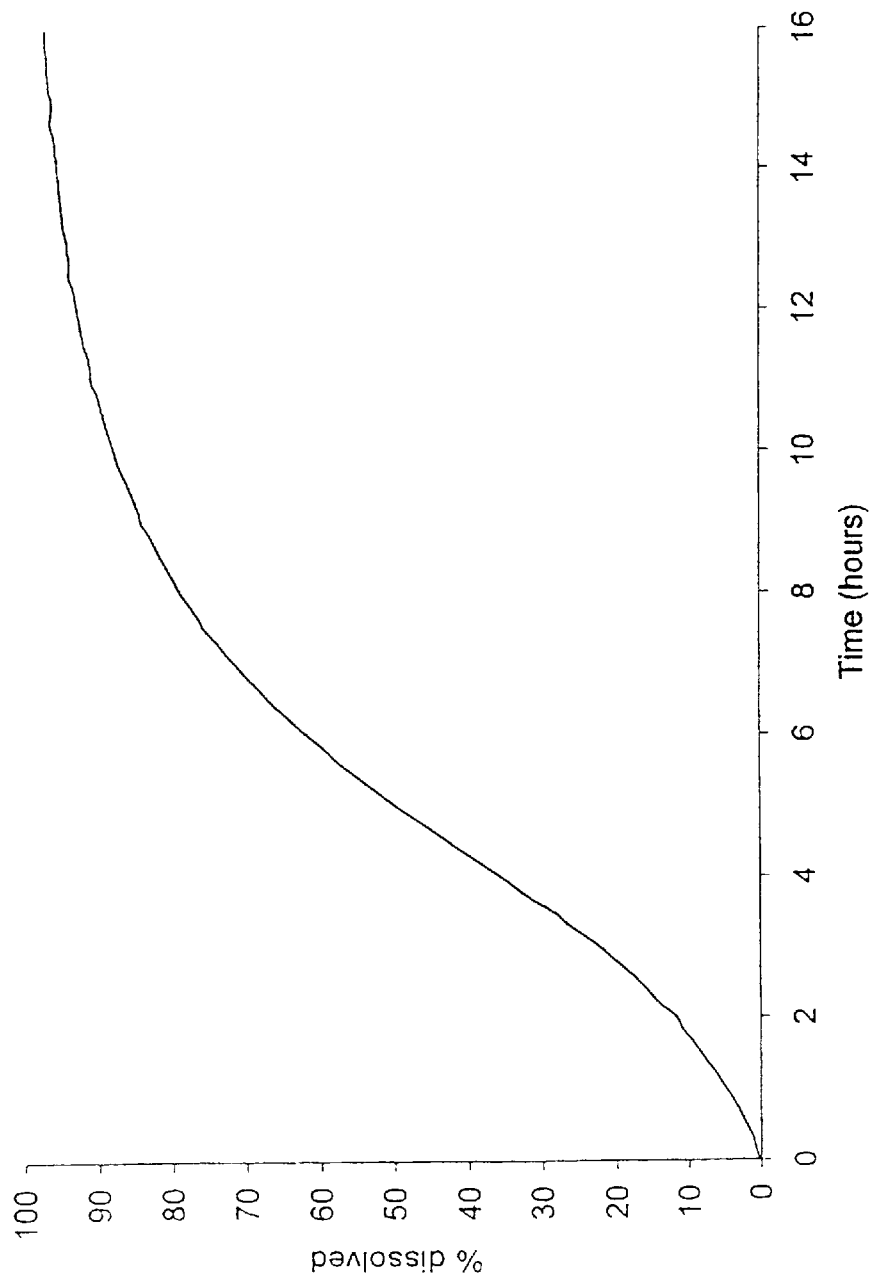
FIG. 9 shows a diagram of the release profile of the modified release coated cores prepared in accordance with Example 22, Batch No. 5.
Figure 10:
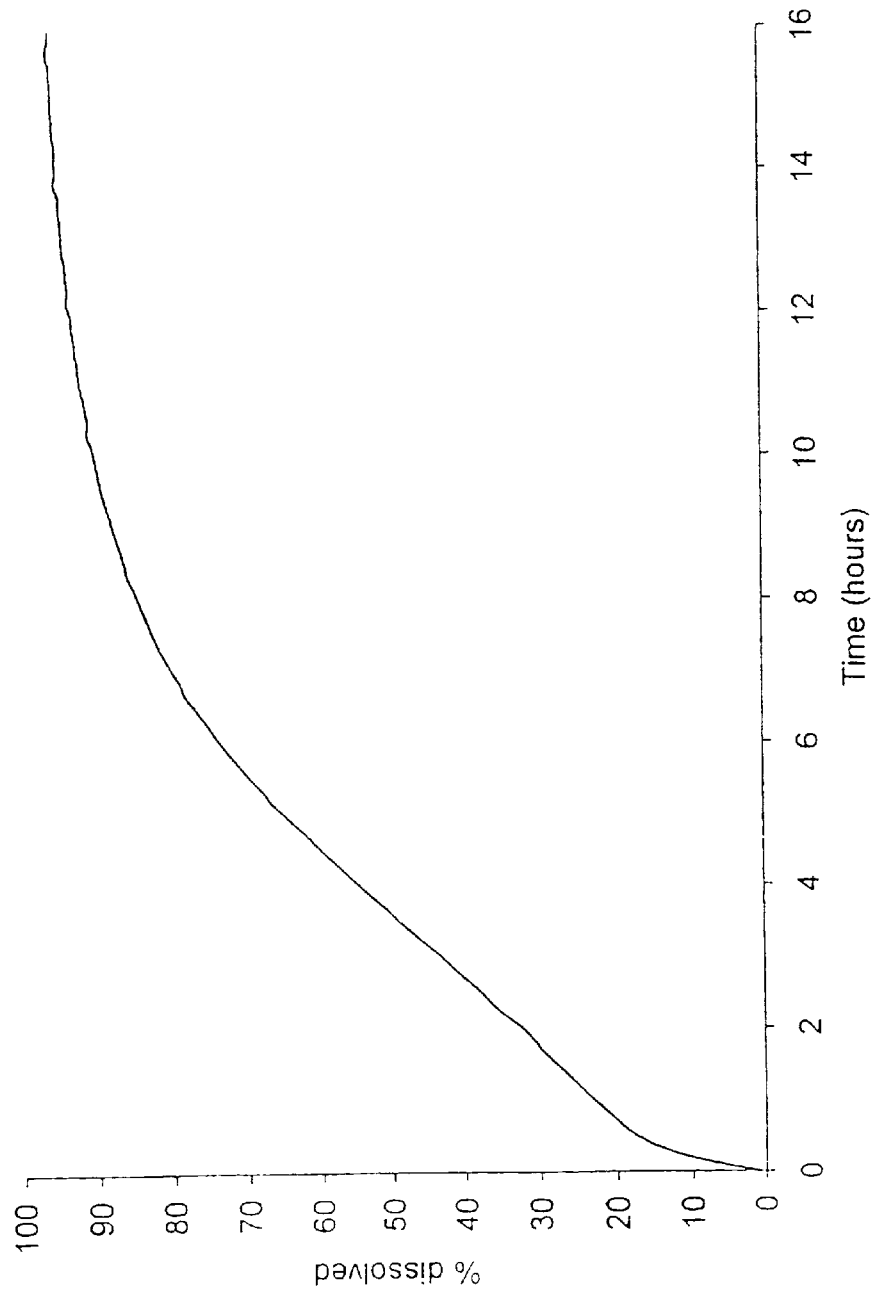
FIG. 10 shows a diagram of the release profile of the modified release coated cores prepared in accordance with Example 23.
Figure 11:
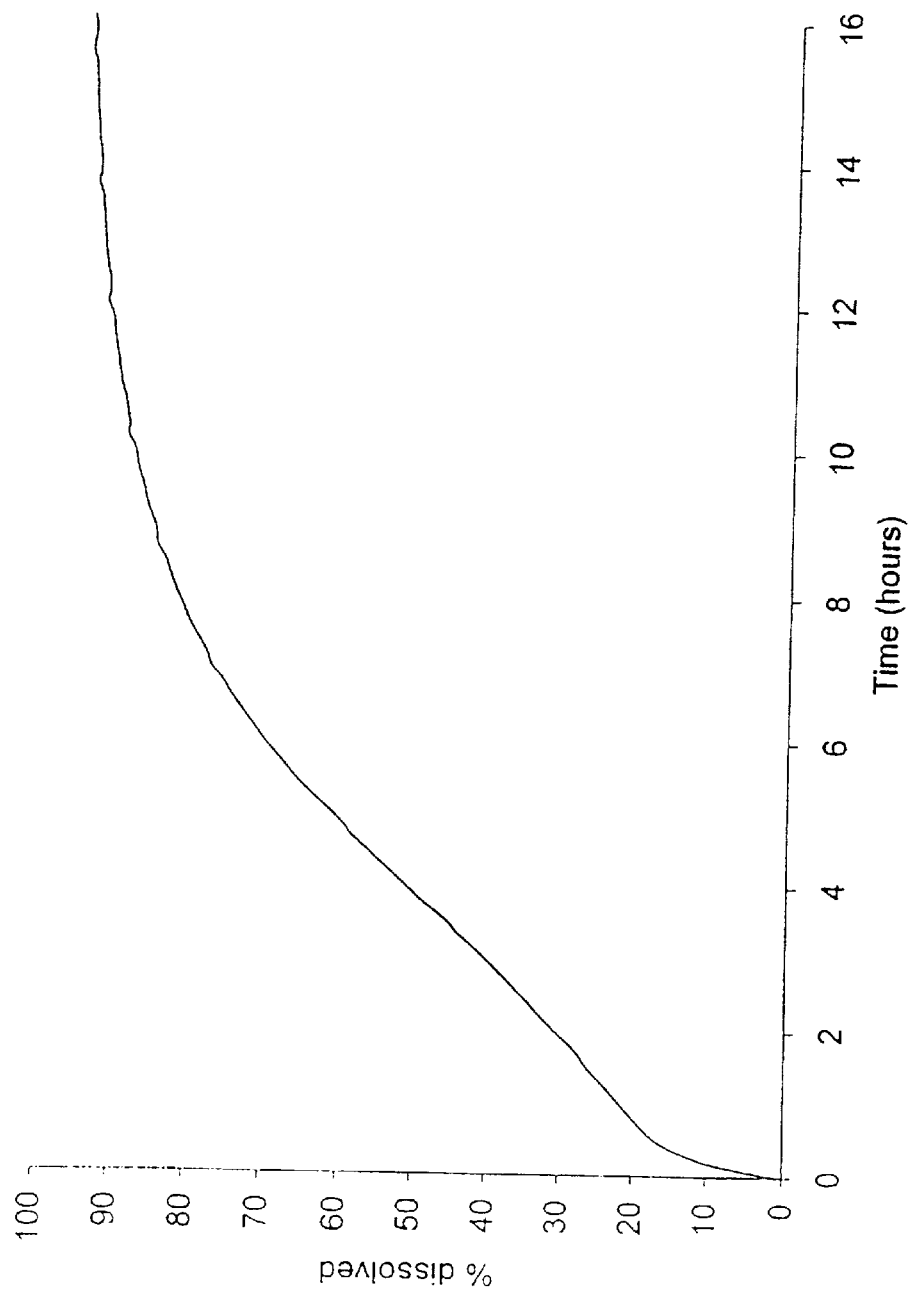
FIG. 11 shows a diagram of the release profile of the modified release coated cores prepared in accordance with Example 24.
Figure 12:
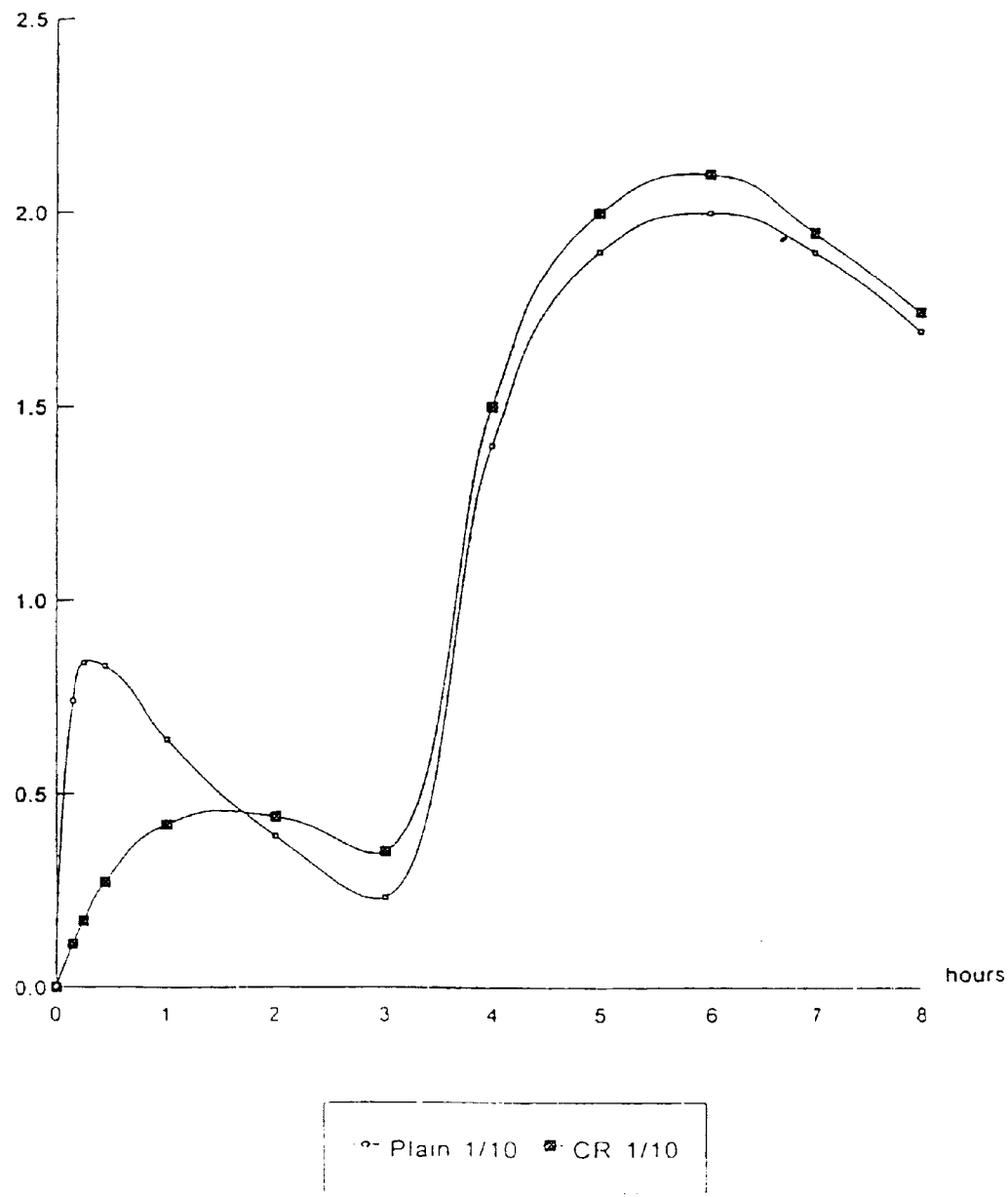
FIG. 12 shows a diagram for the plasma concentration of morphine (morphine sulphate) in arbitrary concentration units after administration of identical total amounts of morphine. The second fraction of both formulations is identical having a substantially slow release. The formulation illustrated by small white squares comprises 10% plain morphine sulphate (non-modified). The other formulation illustrated by filled-in squares comprises a similar amount of morphine in the form of a fraction of modified release multiple units according to the invention. The diagram is based on the assumption of a one compartment open model, wherein the elimination rate constant ($K_e$) for morphine is 0.5; the absorption rate constant ($K_a$) for plain morphine is 10; the absorption rate constant for the slow modified release multiple units of the second fraction is 0.2; and 0.8 for the fast modified release multiple units of the first fraction. This model is intended to illustrate the effect of a first fraction comprising modified release multiple units compared to non-modified release.
Figure 13:
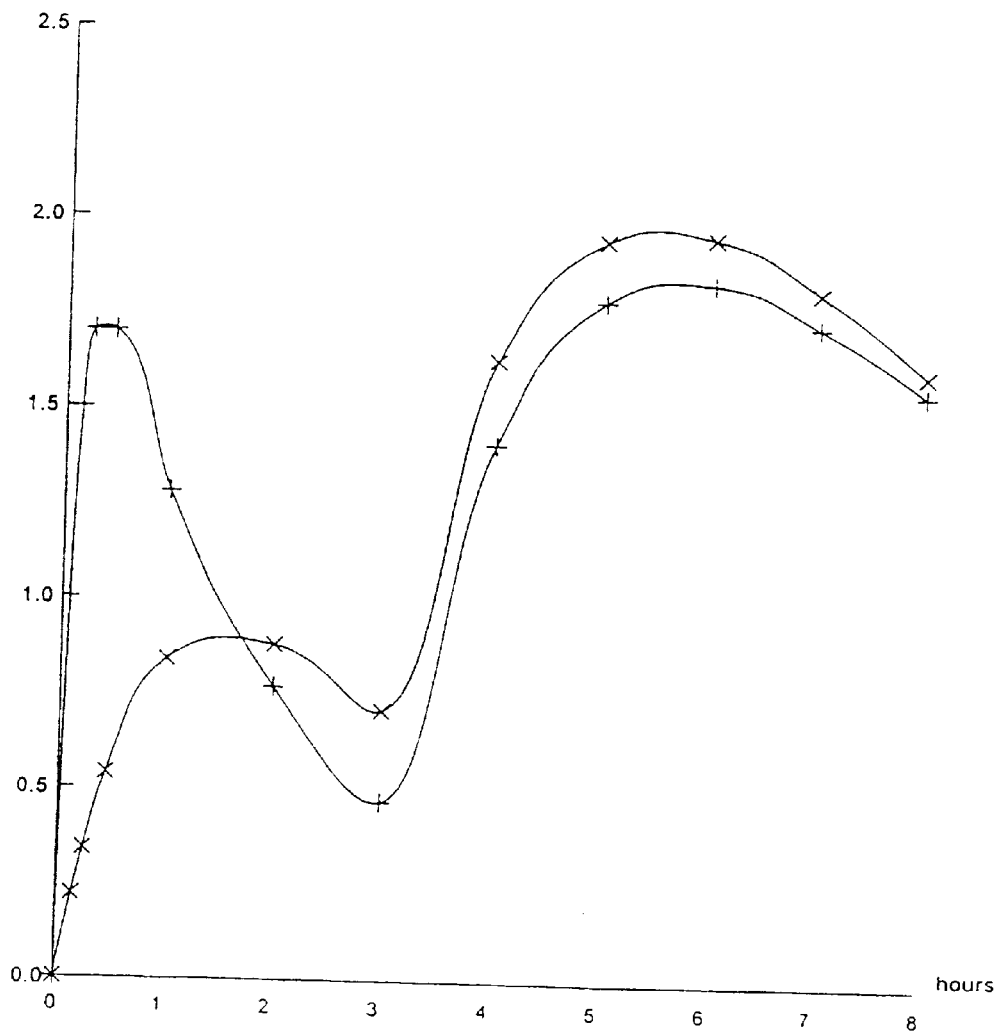
FIG. 13 shows a diagram similar to the one shown in FIG. 12, but wherein the ratio between the first and second fraction of each formulation is 2/10. The formulation comprising 20% plain morphine is illustrated by a cross and the formulation comprising the same amount of a first modified release multiple units fraction is illustrated by a star. The second fraction of each of the formulations is identical.
Figure 14:
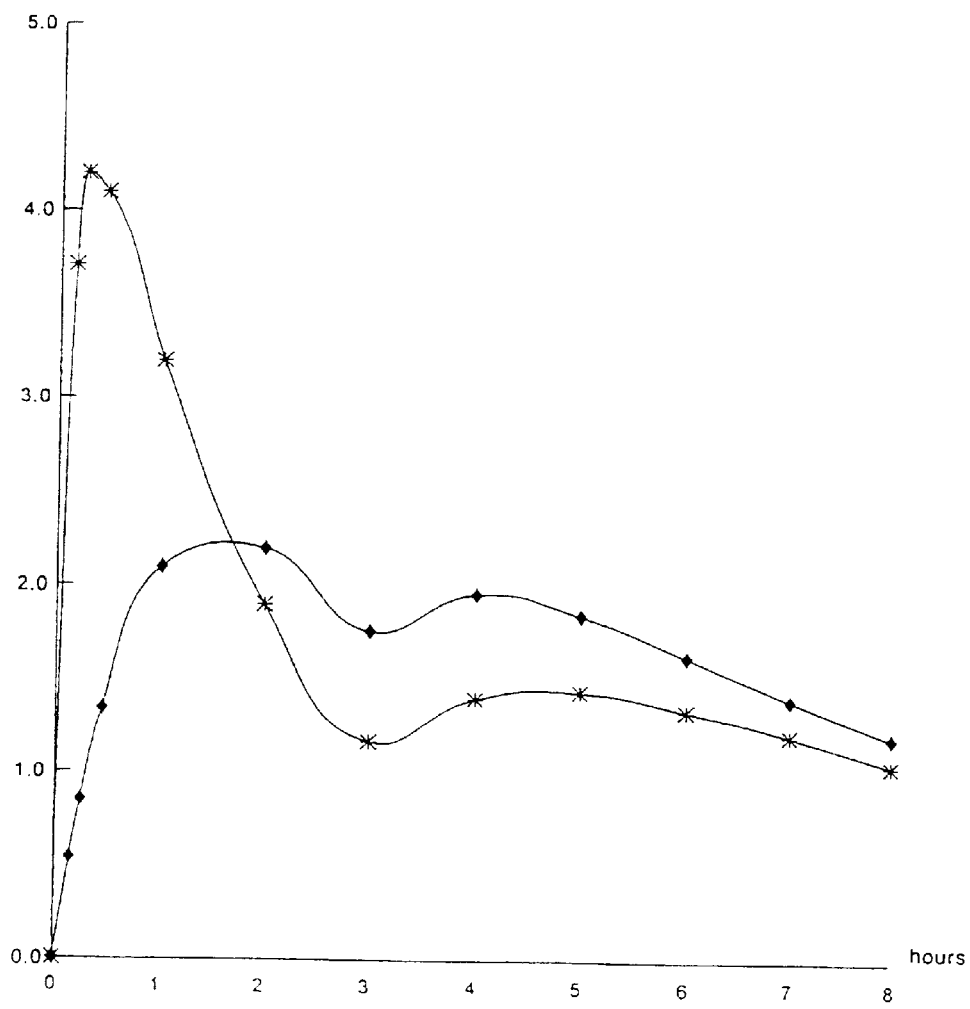
FIG. 14 shows a diagram similar to the one shown in FIG. 12, but wherein the ratio between the fraction is 5/10 and the formulation comprising plain morphine is illustrated by a star and the formulation comprising a first modified release multiple units fraction is illustrated by a filled-in box.
Figure 15:
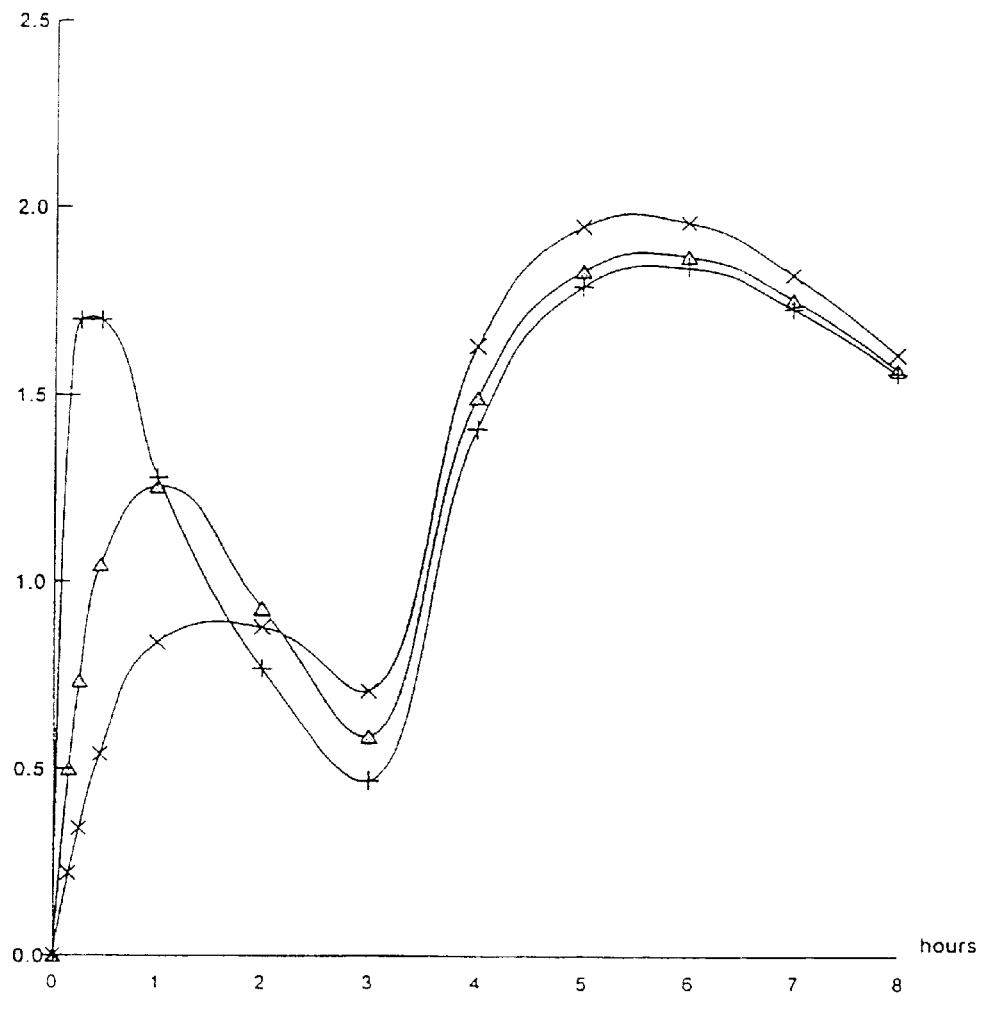
FIG. 15 shows a diagram of three formulations wherein the ratio between the two fractions is 2/10. The curve illustrated by a cross comprises plain morphine in the fast fraction, the curve illustrated by a star comprises modified release multiple units having an absorption rate constant of 0.8 as the fast fraction and the curve illustrated by filled-in triangles comprises a faster modified release multiple units fraction having an absorption rate constant of 2. The modified release multiple units of the second fraction of all three formulations have an absorption rate constant of 0.2. The time lag for absorption of this second fraction is three hours similar to the formulations illustrated in FIGS. 12, 13 and 14.

Materials employed in the formulations which were investigated in the course of development of the present invention were as given in the following. In those cases where reference is given to an official pharmacopoeia, the reference is to the current edition of the stated pharmacopoeia.

The following abbreviations are used:
Ph. Eur.: European Pharmacopoeia
BP: British Pharmacopoeia
USP: United States Pharmacopoeia
NF: National Formulary

| Excipients | Quality | Manufacturer |
| --- | --- | --- |
| Morphine sulphate | BP | Macfarlan |
| Natriumalginat LF 200S | Ph.Eur. | Protan Biopolymer |
| Aspartame | NF | Holland Sweetner Company |
| Maydis Amylum | Ph.Eur. | Cerestar |
| Natrii Citras | Ph.Eur. | Kirsch |
| Natrii Hydrogenocarbonas | Ph.Eur. | Solvay |
| Titanii Dioxidum | Ph.Eur. | Bayer |
| Acidum Tartaricum | Ph.Eur. | Vinal |
| Lemon juice flavour | | Givaudan Dübendorf |
| Lemon flavour | | Givaudan Dübendorf |
| Polyvidonum K 30 | Ph.Eur. | ISP and BASF |
| Cellulosum microcristallinum | Ph.Eur. | FMC |
| Carboxymethylcellulosum Natricum | Ph.Eur. | Henkel |
| Lactosum monohydricum | Ph.Eur. | Hollandse Melksvirkerfabrik and DMV |
| Aqua Purificate | Ph.Eur. | |
| Methylhydroxypropylcellulosum (Pharma Coat 606) | Ph.Eur. | Shin-etsu |
| Methylhydroxypropylcellulosum (Methocel E 5 Premium) | Ph.Eur. | Dow |
| Magnesii stearas | Ph.Eur. | Akcros Chemicals |
| Talcum | Ph.Eur. | Whittaker, Clark and Daniels |
| Simethicone Emulsion | USP | Dow Corning |
| Eudragit NE 30 D | | Supplied by: Rohm Pharma Gmbh, Darmstadt, BRD |
| Calcium sulphate | NF | Giulini Chemie |
| Polysorbatum 20 | Ph.Eur. | Hefti |
| Syloid 244 | Ph.Eur. | Grace |
| Tablettose | Ph.Eur | Meggle |
| Pregelatinized Starch | NF | Colorcon |

Dissolution Method I for Opioid (Morphine Sulphate) (morphine units)
Apparatus: USP/Ph. Eur. dissolution apparatus+PERKIN ELMER fully automatic dissolution system+PEDS PC-programme
Glass fibre filter: Whatman GF/D
Dissolution medium: 900.0 ml 0.1 N HCl
Rotation speed: 100 rpm
Stirrer: Paddle
Sampling times: As appear from tables
Detection wavelength: $\lambda = 284$ nm
Measuring equipment: UV-spectrophotometer, 1 cm cuvette.
Temp. of dissolution medium: 37.0° C.±0.5° C.

Preparation of reagents:
Dissolution medium 0.1 N HCl: 83.0 ml of conc. HCl (37%) is diluted with purified $H_2O$ up to 10.00 l.
Standard stock solution S (2 solutions are prepared): 100 mg (=q, mg) of morphine sulphate R is dissolved in 50.00 ml of 0.1 N HCl.
Control of the 2 standards: 3.00 ml of S is diluted with 0.1N HCl to 200.00 ml(b). Blank specimen: 0.1N HCl(c).
Measurement: At a maximum about 284 nm, the difference in absorbance is measured between solutions b and c ($k_1$).Ph.Eur.V.6.19.
Calculation: For each of the $k_1$-measurements, the response is calculated (with 3 significant figures)

$$R_1 = \frac{k_{1,1}}{q_1} \quad R_2 = \frac{k_{1,2}}{q_2}$$

The deviation between $R_1$ and $R_2$ should not exceed 2%.
Determination of $E_{1\ cm}^{1\%}$:
Stock solutions 1 and 2 are mixed in a ratio of 1:1. 4.00 ml of this solution is diluted with 0.1N HCl to 200.00 ml. The standard solution and the blank specimen (0.1N HCl) are heated to 37° C. When the 2 solutions have reached 37° C., the blank specimen (0.1N HCl) is pumped into a measurement cell. The pumping is performed until all possible air bubbles are removed from the cell.

Background correction procedure is performed and the standard solution is pumped into a measuring cell.
The absorbance of the standard is measured and $E_{1\ cm}^{1\%}$ is calculated:

$$E_{1cm}^{1\%} = \frac{abs_{st} \times 50 \times 200 \times 10}{q_x^- \times 4}$$

$abs_{st}$=absorbance of the standard used
$q_{\bar{x}}$=average weight (mg) of morphine sulphate R weighed to the 2 standard solutions
The calculated $E_{1\ cm}^{1\%}$ is entered the PEDS PC-programme.
Programming of the PEDS-programme in accordance with the PERKIN ELMER manual.
Procedure: 900.0 ml of dissolution medium 0.1 N HCl is filled into each of the desired number of 7 vessels which are heated to 37.0° C.±0.5° C. The dissolution medium of the 7 vessels is pumped into the measuring cells of the UV-spectrophotometer and the background correction procedure is performed. 6 morphine sulphate units and a placebo unit are each weighed into a 25 ml cup. The placebo unit is used as blank specimen during the run.
Procedure for preparing and transferring the units:
1. Mix the content of the cups thoroughly.
2. 10.0 ml of tap water is poured into a measuring glass. The water is poured into the cup, and stirring is performed until the mixture looks homogeneous. The mixture is ready for use after 1 minute.
3. The mixture is stirred immediately before being transferred to the USP vessel. The 7 units prepared are transferred to separate vessels. Each cup is rinsed with dissolution medium from the vessel so that the entire mixture is transferred to the vessel.
4. Immediately after transferring all units to the vessels the dissolution run is started.

Dissolution Method II For Opioid (Morphine Sulphate) (morphine capsules 10 mg, 30 mg, and 60 mg)
Apparatus: USP/Ph. Eur. dissolution apparatus+autosampler (ISCO/Sotax dissolution sampler) or PERKIN ELMER fully automatic dissolution system Glass fibre filter: As described in Method I
Dissolution medium: As described in Method I
Rotation speed: As described in Method I
Stirrer: As described in Method I
Sampling times: As described in Method I
Sampling: Automatic, approximately 9.00 ml (v), no replacement of liquid removed (compensation is made by calculation)
PERKIN ELMER fully automatic dissolution system: UV-measurements at every 10 minutes during 16 hours of test time
Detection wavelength: As described in Method I
Measuring equipment: As described in Method I
Temp. of dissolution medium: As described in Method I
Preparation of reagents:
Dissolution medium 0.1N HCl: As described in Method I
Standard stock solution (S) (2 solutions are prepared): As described in Method I
Solutions for diluting the standard
10 mg
1 clear capsule size 5, is dissolved in 900.0 ml of 0.1N HCl.
30 mg
1 clear capsule size 3, is dissolved in 900.0 ml of 0.1N HCl.
60 m
1 clear capsule size 1, is dissolved in 900.0 ml of 0.1N HCl.
These solutions are used for diluting the standard, and as blank specimen(c).
Standard solution:
10 mg: 5.00 ml of S is diluted with 0.1 N HCl to 50.00 ml. 10.00 ml is diluted with 0.1 N HCl up to 100.00 ml(b).
30 mg: 3.00 ml S is diluted with 0.1 N HCl to 200.00 ml(b).
60 mg: 3.00 ml S is diluted with 0.1 N HCl up to 100.00 ml(b).
Test solutions: The samples are measured undiluted (a).
Measurement: At a maximum about 284 nm the difference of absorbance between solutions b and c ($k_1$) and between solutions a and c ($k_2$) is measured. Ph. Eur. V.6.19.
Calculation: As described in Method I
Manual calculation:

$$GSR = \tfrac{1}{2}(R_1 + R_2)$$

The released amount of morphine sulphate (y) in mg is calculated by means of the formula:

10 mg:

1h:
$$y_1 = \frac{k_2 \times n \times 900 \times 5 \times 10}{GSR \times 100 \times 50 \times 50 \times 100} \quad \text{(released mg morphine sulphate)}$$

3h:
$$z_3 = \frac{k_2 \times n \times (900-v) \times 5 \times 10}{GSR \times 100 \times 50 \times 50 \times 100} \quad y_3 = z_3 + y_1 \times \frac{v}{900}$$

6h:
$$z_6 = \frac{k_2 \times n \times (900-2 \times v) \times 5 \times 10}{GSR \times 100 \times 50 \times 50 \times 100} \quad y_6 = z_6 + y_1 \times \frac{v}{900} + y_3 \times \frac{v}{900-v}$$

9h:
$$z_9 = \frac{k_2 \times n \times (900-3 \times v) \times 5 \times 10}{GSR \times 100 \times 50 \times 50 \times 100}$$
$$y_9 = z_9 + y_1 \times \frac{v}{900} + y_3 \times \frac{v}{900-v} + y_6 \times \frac{v}{900-2 \times v}$$

30 mg:

1h:
$$y_1 = \frac{k_2 \times n \times 900 \times 3}{GSR \times 100 \times 50 \times 200} \quad \text{(released mg morphine sulphate)}$$

3h:
$$z_3 = \frac{k_2 \times n \times (900-v) \times 3}{GSR \times 100 \times 50 \times 200} \quad y_3 = z_3 + y_1 \times \frac{v}{900}$$

6h:
$$z_6 = \frac{k_2 \times n \times (900-2 \times v) \times 3}{GSR \times 100 \times 50 \times 200} \quad y_6 = z_6 + y_1 \times \frac{v}{900} + y_3 \times \frac{v}{900-v}$$

9h:
$$z_9 = \frac{k_2 \times n \times (900-3 \times v) \times 3}{GSR \times 100 \times 50 \times 200}$$
$$y_9 = z_9 + y_1 \times \frac{v}{900} + y_3 \times \frac{v}{900-v} + y_6 \times \frac{v}{900-2 \times v}$$

60 mg:

1h:
$$y_1 = \frac{k_2 \times n \times 900 \times 3}{GSR \times 100 \times 50 \times 100} \quad \text{(released mg morphine sulphate)}$$

3h:
$$z_3 = \frac{k_2 \times n \times (900-v) \times 3}{GSR \times 100 \times 50 \times 100} \quad y_3 = z_3 + y_1 \times \frac{v}{900}$$

6h:
$$z_6 = \frac{k_2 \times n \times (900-2 \times v) \times 3}{GSR \times 100 \times 50 \times 100} \quad y_6 = z_6 + y_1 \times \frac{v}{900} + y_3 \times \frac{v}{900-v}$$

9h:
$$z_9 = \frac{k_2 \times n \times (900-3 \times v) \times 3}{GSR \times 100 \times 50 \times 100}$$
$$y_9 = z_9 + y_1 \times \frac{v}{900} + y_3 \times \frac{v}{900-v} + y_6 \times \frac{v}{900-2 \times v}$$

n=purity of the morphine sulphate standard in percent.
v=sampled amount in ml
Results in %=(y×100)/x
x=stated content (10, 30 or 60)
Procedure: 900.0 ml of dissolution medium 0.1N HCl is filled into each of the desired number of vessels, e.g. 6 vessels which are heated to 37.0° C.±0.5° C. One capsule is transferred into each of the vessels.
Adjustment of autosampler: according to the instructions of the apparatus.
Dissolution Method by Means of a Fully Automatic Equipment
Apparatus: USP/Ph.Eur. dissolution apparatus+PERKIN ELMER Dissolution system (PEDS)+PEDS PC-programme.
Control of the 2 standards: As described in Method I
Measurement: As described in Method I
Calculation: As described in Method I
Determination of $E_1\ _{cm}^{1\%}$: As described in Method I
Procedure: 900.0 ml of dissolution medium 0.1N HCl is filled into each of e.g. 7 vessels which are heated to 37.0° C.±0.5° C. The dissolution medium of the 7 vessels is pumped into the measuring cells of the UV-spectrophotometer and the background procedure is performed. A capsule is transferred to each of 6 vessels. To the 7th vessel the relevant clear capsule is added and used as blank specimen during the run:
10 mg. 1 clear capsule size 5.
30 mg: 1 clear capsule size 3.
60 mg: 1 clear capsule size 1.
Dissolution Method III for Opioid Modified Release Multiple Units (Morphine Sulphate)
Apparatus: As described in Method II
Glass fibre filter: As described in Method I
Dissolution medium: As described in Method I
Rotation speed: As described in Method I
Stirrer: As described in Method I
Sampling times: USP/Ph. Eur. dissolution system+ autosampler: Slow modified release multiple units: 1, 3, 6, 9 h Fast modified release multiple units: ½, 1 h
Mixture of slow and fast modified release multiple units: 1, 3, 6, 9 h
Sampling: As described in Method II
PERKIN ELMER fully automatic dissolution system as described in Method II
Detection wavelength: As described in Method I
Measuring equipment: As described in Method I
Temp. of dissolution medium: As described in Method I
Preparation of reagents: As described in Method I
Standard stock solution (S) (2 solutions are prepared): As described in Method I
Standard solution: 3.00 ml of S is diluted with 0.1N HCl up to 100.00 ml (b).
Test solutions: The samples are measured undiluted (a).
Blank specimen: 0.1N HCl (c).
Measurement: As described in Method I
Calculation: As described in Method I
Manual calculation:

$$GSR = \tfrac{1}{2}(R_1 + R_2)$$

The amount released of morphine sulphate (y) in mg is calculated by means of the formula:
Slow Modified Release Multiple Units 1h:
$$y_1 = \frac{k_2 \times n \times 900 \times 3}{GSR \times 100 \times 50 \times 100} \quad \text{(released mg morphine sulphate)}$$

3h:
$$z_3 = \frac{k_2 \times n \times (900 - v) \times 3}{GSR \times 100 \times 50 \times 100} \quad y_3 = z_3 + y_1 \times \frac{v}{900}$$

6h:
$$z_6 = \frac{k_2 \times n \times (900 - 2v) \times 3}{GSR \times 100 \times 50 \times 100} \quad y_6 = z_6 + y_1 \times \frac{v}{900} + y_3 \times \frac{v}{900 - v}$$

9h:
$$z_9 = \frac{k_2 \times n \times (900 - 3v) \times 3}{GSR \times 100 \times 50 \times 100}$$
$$y_9 = z_9 + y_1 \times \frac{v}{900} + y_3 \times \frac{v}{900 - v} + y_6 \times \frac{v}{900 - 2v}$$

Fast Modified Release Multiple Units

½h:
$$y_{1/2} = \frac{k_2 \times n \times 900 \times v \times 3}{GSR \times 100 \times 50 \times 100} \quad \text{(released mg morphine sulphate)}$$

1h:
$$z_1 = \frac{k_2 \times n \times (900 - v) \times v \times 3}{GSR \times 100 \times 50 \times 100}$$
$$y_1 = z_1 + y_{1/2} \times \frac{v}{900}$$

n=purity of morphine sulphate standard in percent.
v=sampled amount in ml

900 Procedure: 900.0 ml of dissolution medium 0.1N HCl is filled into each of 6 vessels which are heated to 37.0° C.±0.5° C. An amount of modified release multiple units (=p, mg) corresponding to 60 mg of morphine sulphate is transferred to each vessel.
Adjustment of autosampler: according to the instructions of the apparatus.
Dissolution Method by Means of a Fully Automatic Equipment Apparatus
USP/Ph.Eur. dissolution apparatus+PERKIN ELMER Dissolution System (PEDS)+PEDS PC-programme.
Control of the 2 standards: As described in Method I
Procedure: 900.0 ml of dissolution medium 0.1N HCl is filled into each of 6 vessels which are heated to 37.0° C.±0.5° C. An amount of modified release multiple units (=p, mg) corresponding to 60 mg of morphine sulphate is transferred to each of the 6 vessels. In vessel 7 a standard solution is added having a concentration corresponding to 0.07 mg/ml (60 mg/900 ml).
Programming of the PEDS-programme in accordance with the PERKIN ELMER manual.
Dissolution Method IV For Opioid (Morphine Sulphate) (Morphine tablets 40 mg and modified release multiple units for tablets)
Apparatus: As described in Method I
Glass fiber filter: As described in Method I
Dissolution medium: As described in Method I
Rotation speed: As described in Method I
Stirrer: As described in Method I
Sampling times: As appear from tables
Temp. of dissolution medium: As described in Method I
Preparation of reagents:
Dissolution medium 0.1N HCl: As described in Method I
Standard stock solution S (2 solutions are prepared): As described in Method 1.
Control of the 2 standards: As described in Method I.
Measurement: As described in Method I.
Calculation: As described in Method I.
Determination of $E_{1\ cm}^{1\%}$: As described in Method I.
Procedure: 900 ml of dissolution medium 0.1 N HCl is filled into each of the desired number of vessels, which are heated to 37.0° C.±0.5° C.
Tablets:
One tablet is transferred to each of the vessels.
Modified release multiple units:
An amount of units corresponding to 40 mg morphine sulphate is transferred to each of the vessels.
Dissolution Method V for Opioid (Morphine Sulphate) (Morphine capsules 10 mg, 20 mg, 30 mg, 50 mg, 60 mg and 100 mg)
Apparatus: USP/Ph.Eur. dissolution apparatus+autosampler (ISCO/Sotax)
Glass fiber filter: Whatman GF/F
Dissolution medium: As described in Method I
Rotation speed: As described in Method I
Stirrer: As described in Method I
Sampling times: As appear from tables
Sampling: As described in Method II
Temp. of dissolution medium: As described in Method I
Preparation of reagents:
Dissolution medium 0.1 N HCl: As described in Method I
Procedure: As described in Method II.
Standard stock solution (S) (2 solutions are prepared): As described in Method 1.
Calibration curve: Each of the two Standard stock solutions (solution S) are diluted with dissolution medium in order to obtain standard solutions covering three concentration levels:

| Level, calibration curve | Concentration |
|---|---|
| 1 | approx. 18% of declared content |
| 2 | approx. 60% of declared content |
| 3 | approx. 105% of declared content |

Measurement:

Measuring of standard- and test solutions is performed by HPLC

Column: Superspher RP 18 100, 250·4.6 mm
Detector:
 UV-absorption detector, λ=287 nm
Mobile phase:
 11.54 g sodium lauryl sulphate 15.60 g $NaH_2PO_4$, $2H_2O$ are dissolved in 500 ml HPLC grade $H_2O$, 500 ml acetonitrile and 5.00 ml triethyl amine are added and mixed thoroughly. Then pH is adjusted with phosphoric acid (conc.) to pH 3.6±0.05 (approx. 3 ml).
 Vacuum filter through Whatman GF/A filter.
Flow:
 1.0 ml/min.
Loop:
 20 μl for 50, 60, and 100 mg capsules.
 100 μl for 10, 20 and 30 mg capsules.
 Chromatography time for test- and standard solution: approx: 1.75 * $t_{r,morptie}$ [minutes] (=approx. 10 minutes).
Notice:

Test solution specimen for HPLC determination of the samples (=test solution) and solutions for calibration curve are filtered through Whatman GF/F filters before analysis. Test solutions are not diluted.

Calculation: The six solutions described in "CALIBRATION CURVE" are analyzed before injecting samples and linear regression of the responses versus concentrations are performed. The slope ($slope_{calibcurve}$) and intercept ($intercept_{calibcurve}$) is used for calculation.

The 95% confidence interval of intercept must include origin.

Calculate the quantity ($y_1$, $y_3$, $y_6$, $y_9$) of morphine sulphate dissolved in per cent of the stated content in each of the capsules by means of the following expressions:

1h:
$$y_1 = \frac{(A_2 - intercept_{calibcurve}) \times n \times 900 \times 100}{slope_{calibcurve} \times 100 \times x}$$

3h:
$$z_3 = \frac{(A_2 - intercept_{calibcurve}) \times n \times (900 - v) \times 100}{slope_{calibcurve} \times 100 \times x}$$
$$y_3 = z_3 + y_1 \times \frac{v}{900}$$

6h:
$$z_6 = \frac{(A_2 - intercept_{calibcurve}) \times n \times (900 - 2 \times v) \times 100}{slope_{calibcurve} \times 100 \times x}$$
$$y_6 = z_6 + y_1 \times \frac{v}{900} + y_3 \times \frac{v}{900 - v}$$

9h:
$$z_9 = \frac{(A_2 - intercept_{calibcurve}) \times n \times (900 - 3 \times v) \times 100}{slope_{calibcurve} \times 100 \times x}$$
$$y_9 = z_9 + y_1 \times \frac{v}{900} + y_3 \times \frac{v}{900 - v} + y_6 \times \frac{v}{900 - 2 \times v}$$

$A_2$=Area of morphine peak in the chromatogram of test solution
n=purity of the morphine sulphate standard in percent
v=sampled amount in ml
x=stated content of the capsule

EXAMPLE 1

In Example 1 morphine sulphate modified release coated cores were prepared by a manufacture of cores and subsequent coating with an amount of 13.5% (% of core weight).

The cores were prepared by the use of an extrusion/spheronization technique. The ingredients are listed in Table 1. The ingredients are mixed and wetted in a Diosna high shear mixer in which the water is applied by a nozzle (pressure nozzle type Delevan CJ with a bore size of 4.0 mm).

TABLE 1

| Ingredients | Amount (kg) |
|---|---|
| Morphine sulphate | 8.10 |
| Microcrystalline cellulose | 7.26 |
| Lactose | 29.16 |
| Sodium carboxymethlycellulose | 0.45 |
| Purified water | 12.6 |

The wetted mass was extruded in a Nica E 140 extruder with a screen size of 0.6 mm. The extrudate was spheronized in a Fuji-Paudal Marumerizer for 4 min. The cores thus produced were dried on trays for approximately 13 h at 40° C.

The dried cores were fractionated in a Sweco apparatus equipped with a lower screen of 0.500 mm and an upper screen of 0.790 mm.

27.9 kg of these cores were coated with an inner coat, a middle coat and an outer coat in a Glatt WSG 30 fluid bed with a 1.8 mm spray nozzle and a spray pressure of 3 bars for the inner coat and 3.5 bars for the middle and outer coat. The composition of the coating is shown in Table 2.

TABLE 2

| Ingredients | Amount (kg) |
|---|---|
| Inner coat | |
| Hydroxypropylmethylcellulose | 0.163 |
| Magnesium stearate | 0.034 |
| Talc | 0.304 |
| Simethicon emulsion | 0.025 |
| Eudragit NE 30 D | 10.800 |
| Purified water | 13.674 |
| Total | 25.000 |
| Middle coat | |
| Calcium sulphate | 1.817 |
| Hydroxypropylmethylcellulose | 0.230 |
| Simethiconemulsion | 0.012 |
| Polysorbatum 20 | 0.017 |
| Eudragit NE 30 D | 2.428 |

TABLE 2-continued

| Ingredients | Amount (kg) |
|---|---|
| Purified water | 6.941 |
| Total | 11.500 |
| *Outer coat* | |
| Hydroxypropylmethylcellulose | 0.360 |
| Talc | 0.360 |
| Purified water | 8.280 |
| Total | 9.000 |

In the coating process the following amount of inner, middle and outer coat were applied. The amount of dry matter applied calculated in percentage of the core weight also appears from below.

Inner coat:
15.82 kg coating solution
(Dry matter: 8.5% of the core weight)

Middle coat:
4.59 kg coating solution
(Dry matter: 4.0% of the core weight)

Outer coat:
3.49 kg coating solution
(Dry matter: 1.0% of the core weight)

Throughout the coating process the bed temperature was maintained substantially in the interval from 19.5 to 20.9° C. by adjustment of the liquid flow rate. The inlet air temperature was kept at approximately 43° C. After the application of the coatings, the coated cores were cured at a bed temperature of approximately 70° C. for 30 min and thereafter the coated cores were cooled to a bed temperature below 35° C.

The desired dissolution (target) profile and the lower and upper limits for the dissolution rate are shown below:

| | Target | Lower limit | Upper limit |
|---|---|---|---|
| 1 h | 5.0% | 0% | 21.0% |
| 3 h | 33.0% | 11.0% | 55.0% |
| 6 h | 68.0% | 52.0% | 84.0% |
| 9 h | 84.0% | 73.0% | — |

After coating, the coated cores were screened though a 1.2 mm screen. Oversized material was discarded.

The coated cores thus produced had the dissolution data shown in Table 3 (determined by the dissolution method III mentioned above):

TABLE 3

| 1 h | 2.1% |
|---|---|
| 2 h | 9.9% |
| 3 h | 19.9% |
| 4 h | 31.3% |
| 5 h | 42.8% |
| 6 h | 53.3% |
| 7 h | 62.6% |
| 8 h | 70.3% |
| 9 h | 76.2% |
| 10 h | 80.7% |
| 12 h | 86.8% |
| 16 h | 92.5% |

EXAMPLE 2

In Example 2 morphine sulphate modified release coated cores were prepared by manufacturing of cores and subsequent coating with an amount of 11.5 % (% of core weight).

The cores were prepared and coated as described in Example 1 with the exception that in Example 2, 30 kg cores were coated with an amount of inner, middle and outer coat as follows:

Inner coat:
13.01 kg coating solution
(Dry matter: 6.5% of the core weight)

Middle coat:
4.94 kg coating solution
(Dry matter: 4.0% of the core weight)

Outer coat:
3.75 kg coating solution
(Dry matter: 1.0% of the core weight)

and throughout the coating process the bed temperature was maintained substantially in the interval from 19.0 to 20.8° C. by adjustment of the liquid flowrate.

The coated cores thus produced had the dissolution data shown in Table 4 (determined by the dissolution method III mentioned above):

TABLE 4

| 1 h | 18.2% |
|---|---|
| 2 h | 37.4% |
| 3 h | 53.4% |
| 4 h | 65.8% |
| 5 h | 75.3% |
| 6 h | 82.1% |
| 7 h | 86.8% |
| 8 h | 90.1% |
| 9 h | 92.4% |
| 10 h | 94.0% |
| 12 h | 95.9% |
| 16 h | 97.5% |

EXAMPLE 3

In Example 3 morphine sulphate modified release coated cores were prepared by manufacturing of cores and subsequent coating with an amount of 8.0% (% of core weight).

The cores were coated as described in Example 1 with the exception that in Example 3, 30 kg cores were coated with an amount of inner, middle and outer coat as follows:

Inner coat:
6.00 kg coating solution
(Dry matter: 3.0% of the core weight)

Middle coat:
4.94 kg coating solution
(Dry matter: 4.0% of the core weight)

Outer coat:
3.75 kg coating solution
(Dry matter: 1.0% of the core weight)

The desired dissolution profile (target) and the lower and upper limits for the dissolution rate are shown below:

| Target | Lower limit | Upper limit |
|---|---|---|
| 0.5 h 67.0% | 47.0% | 95.0% |
| 1.0 h 91.0% | 71.0% | — | and throughout the coating process the bed temperature was maintained substantially in the interval from 19.3 to 20.5° C. by adjustment of the liquid flow rate.

The coated cores thus produced had the dissolution data shown in Table 5 (determined by the dissolution method III mentioned above):

TABLE 5

| | |
|---|---|
| 10 min | 49.0% |
| 20 min | 77.6% |
| 30 min | 89.5% |
| 40 min | 94.6% |
| 50 min | 97.2% |
| 60 min | 98.4% |

EXAMPLE 4

In Example 4 morphine sulphate modified release coated cores were prepared by manufacturing of cores and subsequent coating with an amount of 12.5% (% of core weight).

The cores were prepared and coated as described in Example 1 with the exception that in Example 4, the liquid addition during the wetting in the Diosna mixer was 12.83 kg and that 30 kg cores were coated with an amount of inner, middle and outer coat as follows:

Inner coat:
 15.01 kg coating solution
 (Dry matter: 7.5% of the core weight)
Middle coat:
 4.94 kg coating solution
 (Dry matter: 4.0% of the core weight)
Outer coat:
 3.75 kg coating solution
 (Dry matter: 1.0% of the core weight)
and throughout the coating process the bed temperature was maintained substantially in the interval from 18.0 to 19.6° C. by adjustment of the liquid flowrate.

The coated cores thus produced had the dissolution data shown in Table 6 (determined by dissolution the method III mentioned above):

TABLE 6

| | |
|---|---|
| 1 h | 10.3% |
| 2 h | 24.9% |
| 3 h | 40.2% |
| 4 h | 54.4% |
| 5 h | 66.7% |
| 6 h | 76.1% |
| 7 h | 83.1% |
| 8 h | 88.1% |
| 9 h | 91.6% |
| 10 h | 94.1% |
| 12 h | 97.3% |
| 16 h | 100.1% |

EXAMPLE 5

In Example 5 morphine sulphate modified release coated cores were prepared by manufacturing of cores and subsequent coating with an amount of 13.5% (% of core weight).

The cores were prepared and coated as described in Example 4 with the exception that in Example 5, 30 kg cores were coated with an amount of inner, middle and outer coat as follows:

Inner coat:
 17.01 kg coating solution
 (Dry matter: 8.5% of the core weight)
Middle coat:
 4.94 kg coating solution
 (Dry matter: 4.0% of the core weight)
Outer coat:
 3.75 kg coating solution
 (Dry matter: 1.0% of the core weight)
and throughout the coating process the bed temperature was maintained substantially in the interval from 18.3 to 19.8° C. by adjustment of the liquid flowrate.

The coated cores thus produced had the dissolution data shown in Table 7 (determined by the dissolution method III mentioned above):

TABLE 7

| | |
|---|---|
| 1 h | 3.4% |
| 2 h | 10.1% |
| 3 h | 19.8% |
| 4 h | 31.3% |
| 5 h | 43.5% |
| 6 h | 54.9% |
| 7 h | 64.9% |
| 8 h | 72.9% |
| 9 h | 79.1% |
| 10 h | 83.7% |
| 12 h | 90.0% |
| 16 h | 95.8% |

EXAMPLE 6

In Example 6 morphine sulphate modified release coated cores were prepared by manufacturing of cores and subsequent coating with an amount of 8.0% (% of core weight).

The cores were prepared and coated as described in Example 4 but with a desired dissolution profile as described in Example 3. Furthermore the following exceptions from Example 4 were chosen: In Example 6, 30 kg cores were coated with an amount of inner, middle and outer coat as follows:

Inner coat:
 6.0 kg coating solution
 (Dry matter: 3.0% of the core weight)
Middle coat:
 4.94 kg coating solution
 (Dry matter: 4.0% of the core weight)
Outer coat:
 3.75 kg coating solution
 (Dry matter: 1.0% of the core weight)
and throughout the coating process the bed temperature was maintained substantially in the interval from 18.2 to 19.8° C. by adjustment of the liquid flowrate.

The coated cores thus produced had the dissolution data shown in Table 8 (determined by the dissolution method III mentioned above):

TABLE 8

| | |
|---|---|
| 10 min | 51.0% |
| 20 min | 79.1% |
| 30 min | 90.5% |
| 40 min | 95.5% |
| 50 min | 98.0% |
| 60 min | 99.2% |

EXAMPLE 7

In Example 8 morphine sulphate modified release coated cores were prepared by manufacturing of cores and subsequent coating with an amount of 13.0% (% of core weight).

The cores were prepared and coated as described in Example 1 with the exception that in Example 7 the liquid addition during the wetting in the Diosna mixer was 12.38 and that 30 kg cores were coated with an amount of inner, middle and outer coat as follows:

Inner coat:

16.01 kg coating solution (Dry matter: 8.0% of the core weight)

Middle coat:

4.94 kg coating solution (Dry matter: 4.0% of the core weight)

Outer coat:

3.75 kg coating solution (Dry matter: 1.0% of the core weight)

and throughout the coating process the bed temperature was maintained substantially in the interval from 20.5 to 22.5° C. by adjustment of the liquid flowrate.

The coated cores thus produced had the dissolution data shown in Table 9 (determined by the dissolution method III mentioned above):

TABLE 9

| | |
|---|---|
| 1 h | 4.3% |
| 2 h | 12.3% |
| 3 h | 24.3% |
| 4 h | 38.6% |
| 5 h | 52.6% |
| 6 h | 64.4% |
| 7 h | 73.6% |
| 8 h | 80.5% |
| 9 h | 85.4% |
| 10 h | 88.9% |
| 12 h | 93.4% |
| 16 h | 97.4% |

EXAMPLE 8

In Example 8 morphine sulphate modified release coated cores were prepared by manufacturing of cores and subsequent coating with an amount of 8.0% (% of core weight).

The cores were prepared and coated as described in Example 7, but with the desired dissolution profile as described in Example 3 and with the exception that in Example 8 30 kg cores were coated with an amount of inner, middle and outer coat as follows:

Inner coat:

6.0 kg coating solution (Dry matter: 3.0% of the core weight)

Middle coat:

4.94 kg coating solution (Dry matter: 4.0% of the core weight)

Outer coat:

3.75 kg coating solution (Dry matter: 1.0% of the core weight)

and throughout the coating process the bed temperature was maintained substantially in the interval from 20.0 to 22.2° C. by adjustment of the liquid flowrate.

The coated cores thus produced had the dissolution data shown in Table 10 (determined by the dissolution method III mentioned above):

TABLE 10

| | |
|---|---|
| 10 min | 41.1% |
| 20 min | 70.7% |
| 30 min | 84.9% |
| 40 min | 92.2% |
| 50 min | 96.0% |
| 60 min | 98.1% |

EXAMPLE 9

In Example 9 morphine sulphate modified release coated cores were prepared by manufacturing of cores and subsequent coating with an amount of 12.2% (% of core weight).

The manufacture of these coated cores was done as described in Example 7 with the exception that in Example 9, 30 kg cores were coated with an amount of inner, middle and outer coat as follows:

Inner coat:

14.41 kg coating solution/suspension (Dry matter: 7.2% of the core weight)

Middle coat:

4.94 kg coating solution/suspension (Dry matter: 4.0% of the core weight)

Outer coat:

3.75 kg coating solution/suspension (Dry matter: 1.0% of the core weight)

and throughout the coating process the bed temperature was maintained substantially in the interval from 20.0 to 22.2° C. by adjustment of the liquid flowrate.

The coated cores thus produced had the dissolution data shown in Table 11 (determined by the dissolution method III mentioned above):

TABLE 11

| | |
|---|---|
| 1 h | 12.2% |
| 2 h | 28.7% |
| 3 h | 44.6% |
| 4 h | 59.1% |
| 5 h | 70.5% |
| 6 h | 78.6% |
| 7 h | 84.2% |
| 8 h | 88.1% |
| 9 h | 90.5% |
| 10 h | 92.3% |
| 12 h | 94.7% |
| 16 h | 96.4% |

EXAMPLE 10

In Example 10 morphine sulphate modified release coated cores were prepared by coating the cores with an amount of 13.5% (% of core weight).

The cores were prepared by the use of an extrusion/spheronization technique. The ingredients are listed in Table 12. The ingredients were mixed and wetted in a Diosna high shear mixer in which the water is applied by a nozzle (Pressure nozzle, Delevan CJ with a bore size of 2.5 mm).

TABLE 12

| Ingredients | Amount (kg) |
| --- | --- |
| Morphine sulphate | 7.20 |
| Microcrystalline cellulose | 6.48 |
| Lactose | 25.92 |
| Sodium Carboxymethylcellulose | 0.40 |
| Purified water | 10.6 |

The wetted mass was extruded in a Nica E 140 extruder with a screen size of 0.6 mm. The extrudate was spheronized in a Fuji-Paudal Elanco Marumerizer for 3.5 min. The cores thus produced were dried on trays for approximately 7 h at 40° C.

The dried cores were fractionated in a Sweco apparatus equipped with a lower screen of 0.500 mm and an upper screen of 0.790 mm.

The above mentioned procedure was replicated 4 times giving a total yield of 147 kg of cores.

28.0 kg of these cores were coated with an inner coat, a middle coat and an outer coat in a Glatt WSG 30 fluid bed with a 1.8 mm spray nozzle and a spray pressure of 3 bars for the inner coat and 3.5 bars for the middle and outer coat. The composition of the coating is shown in Table 13.

TABLE 13

| Ingredients | Amount (kg) |
| --- | --- |
| Inner coat | |
| Hydroxypropylmethylcellulose | 0.104 |
| Magnesium stearate | 0.022 |
| Talc | 0.194 |
| Simethicon emulsion | 0.016 |
| Eudragit NE 30 D | 6.912 |
| Purified water | 8.752 |
| Total | 16.000 |
| Middle coat | |
| Calcium sulphate | 0.790 |
| Hydroypropylmethylcellulose | 0.100 |
| Simethicon emulsion | 0.005 |
| Polysorbatum 20 | 0.0075 |
| Eudragit NE 30 D | 1.055 |
| Purified water | 3.0425 |
| Total | 5.000 |
| Outer coat | |
| Hydroxypropylmethylcellulose | 0.160 |
| Talc | 0.160 |
| Purified water | 3.680 |
| Total | 4.000 |

In the coating process the following amounts of inner, middle and outer coat were applied
Inner coat:
  15.88 kg coating solution/suspension
  (Dry matter: 8.5% of the core weight)
Middle coat:
  4.61 kg coating solution/suspension
  (Dry matter: 4.0% of the core weight)
Outer coat:
  3.50 kg coating solution/suspension
  (Dry matter: 1.0% of the core weight)
Throughout the coating process the bed temperature was maintained substantially in the interval from 18.0 to 20.5° C. by adjustment of the liquid flow rate. The inlet air temperature was kept at approximately 30° C. After the application of the coat the coated cores were cured at a bed temperature of approximately 70° C. for 30 min and thereafter the coated cores were cooled to a bed temperature below 35° C.

After coating, the coated cores were screened through a 1.0 mm screen. Oversized material was discarded.

The coated cores thus produced had the dissolution data shown in Table 14 (determined by the dissolution method III mentioned above):

TABLE 14

| | |
| --- | --- |
| 1 h | 5.4% |
| 2 h | 15.6% |
| 3 h | 29.1% |
| 4 h | 43.6% |
| 5 h | 57.4% |
| 6 h | 68.6% |
| 7 h | 77.2% |
| 8 h | 83.6% |
| 9 h | 88.1% |
| 10 h | 91.3% |
| 12 h | 95.4% |
| 16 h | 99.0% |

EXAMPLE 11

In Example 11 morphine sulphate modified release coated cores were prepared by coating the cores with an amount of 8% (% of core weight).

The cores were prepared as described in Example 10. However, the cores were coated with an amount of inner, middle and outer coat as follows:
Inner coat:
  5.6 kg coating solution/suspension
  (Dry matter: 3.0% of the core weight)
Middle coat:
  4.61 kg coating solution/suspension
  (Dry matter: 4.0% of the core weight)
Outer coat:
  3.50 kg coating solution/suspension
  (Dry matter: 1.0% of the core weight)
and throughout the coating process the bed temperature was maintained substantially in the interval from 18.5 to 22.0° C. by adjustment of the liquid flowrate.

The coated cores thus produced had the dissolution data shown in Table 15 (determined by the dissolution method III mentioned above):

TABLE 15

| | |
| --- | --- |
| 10 min | 38.5% |
| 20 min | 70.2% |
| 30 min | 86.6% |
| 40 min | 94.0% |
| 50 min | 97.8% |
| 60 min | 99.6% |

EXAMPLE 12

In Example 12 the coated cores from Example 10 and Example 11 were mixed in a drum mixer for 5 min. The proportions mixed were:
Example 10: 20.09 kg
Example 11: 4.73 kg
These proportions were calculated on the basis that 80.0% of the morphine sulphate in the mixture should be in the form of coated cores prepared in accordance with Example 10, and 20.0% of the morphine sulphate in the mixture should be in the form of coated cores prepared in accordance with Example 11.

The mixture of cores were admixed 0.186 kg of talc in the drum mixer for 5 min.

The mixture of coated cores thus produced had the dissolution data shown in Table 16 (determined by the dissolution method III mentioned above):

TABLE 16

| | |
|---|---|
| 1 h | 24.0% |
| 2 h | 31.8% |
| 3 h | 41.7% |
| 4 h | 52.7% |
| 5 h | 63.5% |
| 6 h | 73.1% |
| 7 h | 80.1% |
| 8 h | 85.6% |
| 9 h | 89.8% |
| 10 h | 92.8% |
| 12 h | 96.8% |
| 16 h | 100.5% |

The mixture of coated cores were filled into capsules by the means of a Zanasi AZ 40 capsule filler. The characteristics for the capsules are listed in Table 17 (determined by the dissolution method II mentioned above):

TABLE 17

| Capsule size | 5 | 3 | 1 |
|---|---|---|---|
| Amount of coated cores (mg) | 62.5 | 187.4 | 374.8 |
| Dose of morphine sulphate (mg) | 10 | 30 | 60 |
| 1 h dissolution (%) | 23.1 | 22.1 | 22.9 |
| 3 h dissolution (%) | 41.3 | 40.0 | 40.8 |
| 6 h dissolution (%) | 72.9 | 71.8 | 72.4 |
| 9 h dissolution (%) | 91.3 | 88.9 | 89.8 |

EXAMPLE 13

In Example 13 morphine sulphate modified release coated cores were prepared by a manufacture of cores and subsequent coating with an amount of 12.5% (% of core weight).

The coated cores were prepared as described in Example 10 with the exception that the cores were coated with an amount of inner, middle and outer coat as follows:

Inner coat:

14.0 kg coating solution/suspension (Dry matter: 7.5% of the core weight)
Middle coat:

4.61 kg coating solution/suspension (Dry matter: 4.0% of the core weight)
Outer coat:

3.50 kg coating solution/suspension (Dry matter: 1.0% of the core weight)

and throughout the coating process the bed temperature was maintained substantially in the interval from 18.0 to 22.0° C. by adjustment of the liquid flowrate.

The coated cores thus produced had the dissolution data shown in Table 18 (determined by the dissolution method III mentioned above):

TABLE 18

| | |
|---|---|
| 1 h | 10.5% |
| 2 h | 26.5% |
| 3 h | 42.0% |
| 4 h | 55.9% |
| 5 h | 67.5% |
| 6 h | 76.8% |
| 7 h | 83.7% |
| 8 h | 88.4% |
| 9 h | 91.8% |
| 10 h | 94.5% |
| 12 h | 97.4% |
| 16 h | 99.9% |

EXAMPLE 14

In Example 14 morphine sulphate modified release coated cores were prepared by manufacturing of cores and subsequent coating with an amount of 14.5% (% of core weight).

The manufacture of these coated cores were done as described in Example 10 with the exception that the cores were coated with an amount of inner, middle and outer coat as follows:
Inner coat:

17.75 kg coating solution/suspension (Dry matter: 9.5% of the core weight)
Middle coat:

4.61 kg coating solution/suspension (Dry matter: 4.0% of the core weight)
Outer coat:

3.50 kg coating solution/suspension (Dry matter: 1.0% of the core weight)
and throughout the coating process the bed temperature was maintained substantially in the interval from 18.0 to 22.2° C. by adjustment of the liquid flowrate.

The coated cores thus produced had the dissolution data shown in Table 19 (determined by the dissolution method III mentioned above):

TABLE 19

| | |
|---|---|
| 1h | 3.3% |
| 2h | 9.4% |
| 3h | 18.3% |
| 4h | 30.4% |
| 5h | 43.7% |
| 6h | 56.8% |
| 7h | 67.1% |
| 8h | 75.4% |
| 9h | 81.7% |
| 10h | 86.6% |
| 12h | 92.6% |
| 16h | 98.0% |

EXAMPLE 15

In Example 15 morphine sulphate modified release sachettes were prepared by manufacturing of cores and subsequent coating with an amount of 15.0% (% of core weight).

The cores were prepared by the use of an extrusion/spheronization technique. The ingredients are listed in Table 20. The ingredients were mixed and wetted in a Fielder high shear mixer.

TABLE 20

| Ingredients | Amount (kg) |
| --- | --- |
| Morphine sulphate | 0.900 |
| Microcrystalline cellulose | 1.200 |
| Maize starch | 1.800 |
| Lactose | 1.980 |
| Polyvidone | 0.120 |
| Purified water | 2.550 |

The wetted mass was extruded in a Nica E 140 extruder with a screen size of 0.6 mm. The extrudate was spheronized in lab unit for 1.75 min. The cores thus produced were dried on trays for approximately 5 h at 40° C.

The dried cores were fractionated in a Retsch apparatus equipped with a lower screen of 0.500 mm and an upper screen of 0.800 mm.

100 g of these cores were coated with an inner coat, a middle coat and an outer coat in a lab fluid bed with a 0.7 mm spray nozzle and a spray pressure of 0.6 bar. The composition of the coating is shown in Table 21.

TABLE 21

| Ingredients | Amount (g) |
| --- | --- |
| Inner coat | |
| Hydroxypropylmethylcellulose | 6.50 |
| Magnesium stearate | 1.35 |
| Talc | 12.15 |
| Simethicon emulsion | 1.00 |
| Eudragit NE 30 D | 432.00 |
| Purified water | 547.00 |
| Total | 1000.00 |
| Middle coat | |
| Calcium sulphate | 79.00 |
| Hydroxypropylmethylcellulose | 10.00 |
| Simethiconemulsion | 0.50 |
| Polysorbatum 20 | 0.75 |
| Eudragit NE 30 D | 105.50 |
| Purified water | 304.25 |
| Total | 500.00 |
| Outer coat | |
| Hydroxypropylmethylcellulose | 10.00 |
| Talc | 10.00 |
| Purified water | 230.00 |
| Total | 250.00 |

In the coating process the following amount of inner, middle and outer coat were applied:
Inner coat:
 66.70 g coating solution/suspension
 (Dry matter: 10.0% of the core weight)
Middle coat:
 16.50 g coating solution/suspension
 (Dry matter: 4.0% of the core weight)
Outer coat:
 12.50 g coating solution/suspension
 (Dry matter: 1.0% of the core weight)

Throughout the coating process the inlet air temperature was kept at approximately 40° C. and the outlet temperature at approximately 30° C. After the application of the coat the coated cores were cured at a bed temperature of approximately 70° C. for 30 min. and thereafter the coated cores were cooled to a bed temperature below 35° C.

After the coating the coated cores were screened through a 1.0 mm screen. Oversized material was discarded.

45.0 g of the coated cores thus produced and 35 g of a mixture of the composition shown in Table 22 were filled into sachettes filling 230 mg coated cores and 171 mg of the mixture shown in Table 22 in each sachette.

TABLE 22

|  | (mg) |
| --- | --- |
| Sodium citrate | 41.00 |
| Sodium bicarbonate | 77.80 |
| Titanium dioxide | 51.10 |
| Tartaric acid | 45.00 |
| Lemon juice flavour | 4.10 |
| Lemon flavour | 4.10 |
| Aspartam | 4.10 |
| Sodium alginate LF 200S | 122.80 |

The sodium citrate, Sodium bicarbonate and the titanium dioxide were milled in a Fritzh lab mill equipped with a 0.2 mm screen. The tartaric acid was also milled in the Fritzh equipment.

The mixture of coated cores and powder from the sachettes had the dissolution data shown in Table 23 (determined by the dissolution method I mentioned above):

TABLE 23

| 1 h | 5.4% |
| --- | --- |
| 2 h | 17.5% |
| 3 h | 32.8% |
| 4 h | 47.1% |
| 5 h | 58.8% |
| 6 h | 68.3% |
| 7 h | 75.1% |
| 8 h | 80.7% |
| 9 h | 84.2% |
| 12 h | 91.1% |
| 16 h | 95.5% |

EXAMPLE 16

In Example 16 morphine sulphate modified release sachettes were prepared by the manufacture of cores and subsequent coating with an amount of 11% (% of core weight).

The sachettes were prepared as described in Example 15 with the exception that the cores were coated with an amount of inner, middle and outer coat as follows:
Inner coat:
 40 g coating solution/suspension
 (Dry matter: 6.0% of the core weight)
Middle coat:
 16.5 kg coating solution/suspension
 (Dry matter: 4.0% of the core weight)
Outer coat:
 12.5 kg coating solution/suspension
 (Dry matter: 1.0% of the core weight)

The mixture of coated cores and powder from the sachettes had the dissolution data shown in Table 24 (determined by the dissolution method I mentioned above):

TABLE 24

| 0.5 h | 19.6% |
| --- | --- |
| 1 h | 47.2% |
| 1.5 h | 66.4% |
| 3 h | 91.5% |
| 6 h | 101.1% |

EXAMPLE 17

In Example 17 4 batches of morphine sulphate modified release coated cores were prepared by the manufacture of cores and subsequent coating with an amount of 7.0% or 9.0% or 11.0% or 13.0% (% of core weight).

The cores were prepared by the use of an extrusion/spheronization technique. The ingredients are listed in Table 25. The ingredients are mixed and wetted in a Kenwood Major laboratory mixer.

TABLE 25

| Ingredients | Amount (g) |
| --- | --- |
| Morphine sulphate | 75.00 |
| Microcrystalline cellulose | 85.00 |
| Lactose | 340.00 |
| Purified water | 180.00 |

The wetted mass was extruded in a Nica E 140 extruder with a screen size of 0.6 mm. The extrudate was spheronized in a laboratory unit for 2 min. The cores thus produced were dried in a laboratory scale fluid bed at 40° C. for approximately 8 min.

The dried cores were fractionated in a Retsch apparatus equipped with a lower screen of 0.500 mm and an upper screen of 0.800 mm.

100 g of these cores were coated with an inner and an outer coat in a laboratory fluid bed with a 0.7 mm spray nozzle and a spray pressure of 0.6 bar. The composition of the coating is shown in Table 26.

TABLE 26

| Ingredients | Amount (g) |
| --- | --- |
| Inner coat | |
| Hydroxypropylmethylcellulose | 1.30 |
| Magnesium stearate | 0.27 |
| Talc | 2.43 |
| Simethicon emulsion | 0.20 |
| Eudragit NE 30 D | 86.40 |
| Purified water | 109.40 |
| Total | 200.00 |
| Outer coat | |
| Hydroxypropylmethylcellulose | 4.00 |
| Talc | 4.00 |
| Purified water | 92.00 |

The following amounts of inner and outer coat were applied

I
Inner coat:
  39.84 g coating solution/suspension
  (Dry matter: 6.0% of the core weight)
Outer coat:
  12.50 g coating solution/suspension
  (Dry matter: 1.0% of the core weight)
II
Inner coat:
  53.12 g coating solution/suspension
  (Dry matter: 8.0% of the core weight)
Outer coat:
  12.50 g coating solution/suspension
  (Dry matter: 1.0% of the core weight)
III
Inner coat:
  66.40 g coating solution/suspension
  (Dry matter: 10.0% of the core weight)
Outer coat:
  12.50 g coating solution/suspension
  (Dry matter: 1.0% of the core weight)
IV
Inner coat:
  79.70 g coating solution/suspension
  (Dry matter: 12.0% of the core weight)
Outer coat:
  12.50 g coating solution/suspension
  (Dry matter: 1.0% of the core weight)

Throughout the coating process the inlet air temperature was kept at approximately 40° C. and the outlet air temperature at approximately 33° C. After the application of the coat the coated cores were cured at a bed temperature of approximately 70° C. for 30 min and thereafter the coated cores were cooled to a bed temperature below 35° C.

After coating, the coated cores were screened through a 1.0 mm screen. Oversized material was discarded.

The coated cores thus produced had the dissolution data shown in Table 27 (determined by the dissolution method III mentioned above):

TABLE 27

|  | I (%) | II (%) | III (%) | IV (%) |
| --- | --- | --- | --- | --- |
| 1 h | 15.4 | 8.9 | 7.4 | 2.7 |
| 2 h | 29.4 | 15.9 | 11.9 | 4.8 |
| 3 h | 43.1 | 23.7 | 15.6 | 7.1 |
| 4 h | 55.9 | 33.9 | 21.6 | 10.8 |
| 6 h | 75.1 | 55.6 | 41.7 | 26.9 |
| 9 h | 88.7 | 77.2 | 67.7 | 56.2 |
| 10 h | 90.9 | 81.5 | 73.6 | 63.4 |
| 11 h | 92.3 | 84.5 | 77.8 | 69.2 |
| 12 h | 93.8 | 87.5 | 81.9 | 74.0 |
| 16 h | 96.2 | 92.8 | 90.0 | 85.3 |

EXAMPLE 18

In Example 18 morphine sulphate modified release coated cores were prepared by a manufacture of cores and subsequent coating with an amount of 13.0% (% of core weight). The cores thus produced were compressed into tablets.

The cores were prepared by the use of an extrusion/spheronization technique. The ingredients are listed in Table 28. The ingredients were mixed and wetted in a Kenwood Major lab mixer.

TABLE 28

| Ingredients | Amount (g) |
| --- | --- |
| Morphine sulphate | 37.50 |
| Microcrystalline cellulose | 42.50 |
| Lactose | 170.00 |
| Purified water | 90.00 |

The wetted mass was extruded in a Nica E 140 extruder with a screen size of 0.6 mm. The extrudate was spheronized in laboratory unit for 2 min. The cores thus produced were dried in a laboratory scale fluid bed at 40° C. for approximately 10 min.

The dried cores were fractionated in a Retsch apparatus equipped with a lower screen of 0.500 mm and an upper screen of 0.800 mm.

100 g of these cores were coated as described in Example 17 with the application of the following amount of inner and outer coating:

Inner coat:
 79.70 g coating solution/suspension
 (Dry matter: 12.0% of the core weight)
Outer coat:
 12.50 g coating solution/suspension
 (Dry matter: 1.0% of the core weight)

These coated cores were mixed in a cubic mixer with two batches of approximately 100 g of coated cores produced as described in Example 17 (by application of 12.0%+1.0% dry matter) giving a total batch of approximately 300 g of coated cores.

These coated cores were used in a dry granulation. The composition of this granulate is described in Table 29

TABLE 29

| Ingredients | Amount (g) |
| --- | --- |
| Morphine, coated cores | 67.50 |
| Starch 1500 | 6.03 |
| Microcrystalline cellulose | 12.06 |
| Tablettose | 1.53 |
| Syloid | 1.08 |
| Magnesium stearate | 0.18 |
| Talc | 1.62 |

The mixing was done in a cubic mixer as known per se. The dry granulation was replicated giving a total of 180 g of granulate.

Tablets were produced from this granulate by the use of a Fette exacta compression machine. The compression force applied was either approximately 17 kN (designated 1) or approximately 9 kN (designated 2) and the mass of the tablets were approximately 400 mg.

The tablets thus produced had the dissolution data shown in Table 30 (determined by the dissolution method IV described above). The data for the release of the corresponding coated cores are shown in Table 31 (determined by the dissolution method IV described above):

TABLE 30

| | (1) (%) | (2) (%) |
| --- | --- | --- |
| 1 h | 35.2 | 32.1 |
| 3 h | 60.9 | 57.1 |
| 6 h | 77.6 | 75.4 |
| 9 h | 87.2 | 87.3 |
| 12 h | 94.0 | 94.4 |
| 15 h | — | 100.4 |
| 16 | 97.2 | — |

TABLE 31

| 1 h | 8.9% |
| --- | --- |
| 3 h | 18.8% |
| 6 h | 38.7% |
| 9 h | 59.5% |
| 12 h | 74.3% |
| 15 h | 82.9% |

EXAMPLE 19

In Example 19 the coated cores from Example 1, 2 and 3 were mixed in a drum mixer for 5 min. The proportions mixed were:
Example 1: 29.5 kg
Example 2: 20.5 kg
Example 3: 12.1 kg These proportions were calculated so that 80.0% of the resulting amount of the morphine sulphate in the mixture would come from the morphine in the Example 1 and the Example 2 formulations and 20.0% of the morphine sulphate in the mixture would come from the morphine in the Example 3 formulation.

The amounts of Example 1 and Example 2 formulations were chosen in order to get the dissolution of this mixture as close as possible to the target described in Example 1.

The overall mixture of cores described above were admixed 0.466 kg of talc in the drum mixer for 5 min.

The mixture of coated cores thus produced had the dissolution data shown in Table 32 (determined by the dissolution method III mentioned above):

TABLE 32

| 1 h | 29.7% |
| --- | --- |
| 2 h | 41.2% |
| 3 h | 52.2% |
| 4 h | 62.3% |
| 5 h | 71.2% |
| 6 h | 78.5% |
| 7 h | 84.8% |
| 8 h | 88.9% |
| 9 h | 92.2% |
| 10 h | 94.8% |
| 12 h | 98.1% |

The mixture of coated cores were filled into capsules by the means of a Zanasi AZ 40 capsule filler. The characteristics for the capsules are listed in Table 33 (dissolution determined by the dissolution method V mentioned above):

TABLE 33

| Capsule size | 3 | 1 |
| --- | --- | --- |
| Amount of coated cores (mg) | 125.8 | 377.5 |
| Dose of morphine sulphate (mg) | 20 | 60 |
| 1 h dissolution | 30.3 | 29.6 |
| 3 h dissolution | 53.7 | 52.2 |
| 6 h dissolution | 80.3 | 79.7 |
| 9 h dissolution | 94.4 | 94.5 |

EXAMPLE 20

In Example 20 the coated cores from Example 4, 5 and 6 were mixed in a drum mixer for 5 min. The proportions mixed were:
Example 4: 31.2 kg
Example 5: 30.1 kg
Example 6: 14.5 kg These proportions were calculated as described above on the basis that 80.0% of the morphine sulphate in the mixture should be in the form of the Example 4 and the Example 5 formulations and 20.0% of the morphine sulphate in the mixture should be in the form of the Example 6 formulation.

The amounts of Example 4 and Example 5 formulation were chosen in order to get the dissolution of this mixture as close as possible to the target described in Example 1.

The overall mixture of cores described above were admixed 0.569 kg of talc in the drum mixer for 5 min.

The mixture of coated cores thus produced had the dissolution data shown in Table 34 (determined by the dissolution method III mentioned above):

TABLE 34

| | |
|---|---|
| 1 h | 23.3% |
| 2 h | 38.4% |
| 3 h | 44.3% |
| 4 h | 55.2% |
| 5 h | 65.3% |
| 6 h | 73.2% |
| 7 h | 80.2% |
| 8 h | 85.1% |
| 9 h | 88.8% |
| 10 h | 91.3% |
| 12 h | 94.9% |
| 16 h | 98.0% |

The mixture of coated cores were filled into capsules by the means of a Zanasi AZ 40 capsule filler. The characteristics for the capsules are listed in Table 35 (dissolution determined by the dissolution method V mentioned above):

TABLE 35

| | |
|---|---|
| Capsule size | 00 |
| Amount of coated cores (mg) | 629.1 |
| Dose of morphine sulphate (mg) | 100 |
| 1 h dissolution (%) | 26.5 |
| 3 h dissolution (%) | 48.0 |
| 6 h dissolution (%) | 77.5 |
| 9 h dissolution (%) | 93.5 |

EXAMPLE 21

In Example 21 the coated cores from the Examples 7, 8 and 9 were mixed in a drum mixer for 5 min. The proportions mixed were:
Example 7: 32.2 kg
Example 8: 13.3 kg
Example 9: 25.0 kg These proportions were calculated as described above on the basis that 80.0% of the morphine sulphate in the mixture should be in the form of the Example 7 and the Example 9 formulations, and 20.0% of the morphine sulphate in the mixture should be in the form of the Example 8 formulation.

The amounts of the Example 7 and the Example 8 formulations were chosen in order to get the dissolution of this mixture as close as possible to the target described in Example 1.

The mixture of cores were admixed 0.530 kg of talc in the drum mixer for 5 min.

The mixture of coated cores thus produced had the dissolution data shown in Table 36 (determined by the dissolution method III mentioned above):

TABLE 36

| | |
|---|---|
| 1h | 24.7% |
| 2h | 36.2% |
| 3h | 47.2% |
| 4h | 59.3% |
| 5h | 69.3% |
| 6h | 77.1% |
| 7h | 83.1% |
| 8h | 86.9% |
| 9h | 89.7% |
| 10h | 91.8% |
| 12h | 94.4% |
| 16h | 96.6% |

The mixture of coated cores were filled into capsules by the means of a Zanasi AZ 40 capsule filler. The characteristics for the capsules are listed in Table 37 (dissolution determined by the dissolution method V mentioned above):

TABLE 37

| | Capsule size | | |
|---|---|---|---|
| | 4 | 3 | 1 |
| Amount of coated cores (mg) | 62.9 | 188.7 | 314.6 |
| Dose of morphine sulphate (mg) | 10 | 30 | 50 |
| 1h dissolution (%) | 23.9 | 25.4 | 23.8 |
| 3h dissolution (%) | 44.6 | 47.5 | 47.6 |
| 6h dissolution (%) | 76.2 | 79.3 | 78.6 |
| 9h dissolution (%) | 90.2 | 92.5 | 92.9 |

EXAMPLE 22

In Example 22 morphine sulphate modified release coated cores were prepared and subsequent coated as described in Example 1. The amount of cores coated and inner coat applied as well as the dissolution data method for determination of the release of morphine sulphate (determined by the dissolution method III mentioned above) appear from Table 38 below:

TABLE 38

| | Batch No. | |
|---|---|---|
| | 1 | 3 |
| Amount of cores coated: (kg) | 27.7 | 27.7 |
| Inner coat applied (%, of cores) | 7.5 | 8.9 |
| Product temperature, coating (approx. ° C.) | 19.0–21.8 | 19.4–21.6 |
| 1h dissolution (%) | 9.9 | 3.9 |
| 2h dissolution (%) | 25.9 | 10.8 |
| 3h dissolution (%) | 41.7 | 21.5 |
| 4h dissolution (%) | 56.7 | 34.6 |
| 5h dissolution (%) | 69.0 | 48.9 |
| 6h dissolution (%) | 78.3 | 61.0 |
| 9h dissolution (%) | 92.3 | 83.7 |
| 10h dissolution (%) | 94.6 | 87.7 |
| 14h dissolution (%) | — | 95.8 |
| 16h dissolution (%) | 99.7 | — |

| | Batch No. | |
|---|---|---|
| | 4 | 5 |
| Amount of cores coated: (kg) | 27.7 | 27.9 |
| Inner coat applied (%, of cores) | 8.0 | 8.4 |
| Product temperature, coating (approx. ° C.) | 18.8–22.0 | 19.5–21.6 |
| 1h dissolution (%) | 6.3 | 4.7 |
| 2h dissolution (%) | 18.0 | 11.7 |
| 3h dissolution (%) | 32.4 | 22.2 |
| 4h dissolution (%) | 47.6 | 35.5 |
| 5h dissolution (%) | 61.2 | 49.4 |
| 6h dissolution (%) | 72.0 | 61.7 |
| 7h dissolution (%) | — | 71.4 |
| 9h dissolution (%) | 89.9 | 84.2 |
| 10h dissolution (%) | 92.8 | 87.8 |
| 15h dissolution (%) | 99.3 | — |
| 16h dissolution (%) | — | 97.2 |

| | Batch No. 2 |
|---|---|
| Amount of cores coated: (kg) | 27.7 |
| Inner coat applied (%, of cores) | 3.0 |
| Product temperature, coating (approx, ° C.) | 19.0–21.9 |
| 10 min dissolution (%) | 50.9 |
| 20 min dissolution (%) | 78.9 |
| 30 min dissolution (%) | 91.0 |
| 40 min dissolution (%) | 96.2 |
| 50 min dissolution (%) | 98.7 |
| 60 min dissolution (%) | 100.1 |

EXAMPLE 23

In Example 23 the coated cores from Example 22 Batch Nos 1, 2 and 3 were mixed in a drum mixer for 5 min. The proportions mixed were:
Example 22 Batch No. 1: 27.3 kg
Example 22 Batch No. 2: 13.2 kg
Example 22 Batch No. 3: 28.4 kg These proportions were calculated as described above on the basis that 80.0% of the morphine sulphate in the mixture should be in the form of the Example 22 Batch No. 1 and the Example 22 Batch No. 3 formulations and 20.0% of the morphine sulphate in the mixture should be in the form of the Example 22 Batch No. 2 formulation.

The amounts of Example 22 Batch No. 1 and Example 22 Batch No. 3 formulations were chosen in order to get the dissolution of this mixture as close as possible to the target described in Example 1.

The mixture of cores were admixed 0.520 kg of talc in the drum mixer for 5 min.

The mixture of coated cores thus produced had the dissolution data shown in Table 39 (determined by the dissolution method III mentioned above):

TABLE 39

| | |
|---|---|
| 1h | 23.0% |
| 2h | 32.2% |
| 3h | 43.1% |
| 4h | 54.6% |
| 5h | 65.0% |
| 6h | 73.6% |
| 7h | 79.9% |
| 8h | 84.6% |
| 9h | 87.9% |
| 10h | 90.3% |
| 12h | 93.3% |
| 16h | 96.0% |

The mixture of coated cores were filled into capsules by the means of a Zanasi AZ 40 capsule filler. The characteristics for the capsules are listed in Table 40 (dissolution determined by the dissolution method V mentioned above):

TABLE 40

| | Capsule size 00 |
|---|---|
| Amount of coated cores (mg) | 629.1 |
| Dose of morphine sulphate (mg) | 100 |
| 1h dissolution (%) | 25.1 |
| 3h dissolution (%) | 45.6 |
| 6h dissolution (%) | 76.1 |
| 9h dissolution (%) | 90.4 |

EXAMPLE 24

In Example 24 the coated cores from Example 22 Batch Nos 2, 4 and 5 were mixed in a drum mixer for 5 min. The proportions mixed were:
Example 22 Batch No. 2: 12.1 kg
Example 22 Batch No. 4: 29.0 kg
Example 22 Batch No. 5: 21.9 kg These proportions were calculated on the basis that 80,0% of the morphine sulphate in the mixture should be in the form of the Example 22 Batch No. 4 and the Example 22 Batch No. 5 formulations, and 20.0% of the morphine sulphate in the mixture should be in the form of the Example 22 Batch No. 2 formulation.

The amounts of Example 22 Batch No. 4 and Example 22 Batch No. 5 formulation were chosen in order to get the dissolution of this mixture as close as possible to the target described in Example 1.

The mixture of cores were admixed 0.470 kg of talc in the drum mixer for 5 min.

The mixture of coated cores thus produced had the dissolution data shown in Table 41 (determined by the dissolution method III mentioned above):

TABLE 41

| | |
|---|---|
| 1h | 21.8% |
| 2h | 30.7% |
| 3h | 40.3% |
| 4h | 51.2% |
| 5h | 61.3% |
| 6h | 70.3% |
| 7h | 77.3% |
| 8h | 81.9% |
| 9h | 85.4% |
| 10h | 88.1% |
| 12h | 91.9% |
| 16h | 94.6% |

The mixture of coated cores were filled into capsules by the means of a Zanasi AZ 40 capsule filler. The characteristics for the capsules are listed in Table 42 (dissolution determined by the dissolution method V mentioned above):

TABLE 42

| | Capsule size | |
|---|---|---|
| | 4 | 0 |
| Amount of coated cores (mg) | 62.9 | 377.9 |
| Dose of morphine sulphate (mg) | 10 | 60 |
| 1h dissolution (%) | 22.7 | 25.0 |
| 3h dissolution (%) | 40.9 | 44.1 |
| 6h dissolution (%) | 71.7 | 73.8 |
| 9h dissolution (%) | 88.4 | 89.2 |

Clinical Study

In the following tests, modified release capsules prepared in accordance with Example 12 are referred to as Repro-Dose® Morphine.

Test 1 (code PDMO-012):

A comparative, single dose, open, randomised, three phase, cross-over study in healthy volunteers evaluating the bioavailability of two modified release preparations: Repro-Dose® Morphine (RDM) and Kapanol® (KAP) versus a plain morphine tablet, Morfin DAK® (MOR).

Trial Centre: Daw Park Repatriation Hospital, Daws Road, Daw Park, Adelaide, South Australia 5041

Trial objectives:

The aim of the study was i) to investigate the single dose pharmacokinetic profiles of morphine from Repro-Dose® Morphine, Kapanol® and Morfin DAK® in order to compare the rate and extent of absorption plus the in vivo release characteristics of a single dose of the three preparations and ii) to investigate in vitro/in vivo correlations and to evaluate the adverse events reported during the trial period.

Design and number of volunteers:

The study was a single dose, open, randomised, three phase, cross-over study in 24 healthy volunteers. All drop-outs and withdrawals were replaced.

Volunteers:

Healthy volunteers of either sex, 18–45 years, weight ±10% of ideal body weight based on age, height and body frame, who had given written informed consent. Volunteers who took other medication, who had a drug exposure amounting to drug abuse or addiction, who had made blood donations within 3 months prior to study, who had participated in studies during the last 3 months, who had any history of emotional instability or psychiatric disorder, who were not likely to comply with the protocol, who had received any opiates (other than codeine) in the 6 months prior to the study and who had taken codeine in the month prior to the study, whose alcohol consumption exceeded more than 40 g alcohol (4 standard alcoholic drinks) for men and 20 g alcohol (2 standard alcoholic drinks) for women respectively, who had positive Hepatitis B and/or Hepatitis C surface antigen or HIV, who had any allergy or intolerance to the compounds, who had acute or chronic diseases which could influence the health of the volunteer or the study result, who had clinically relevant abnormal laboratory tests or who were pregnant or lactating were not included.

Trial medication:

Repro-Dose® Morphine modified release capsules 30 mg, Kapanol® modified release capsules 20 mg or Morfin DAK® tablets 30 mg.

Single doses of 60 mg of Repro-Dose Morphine® and Kapanol® and 30 mg of Morfin DAK® were given with 240 ml water.

Primary variable:

The areas under the plasma concentration-time curve of morphine from zero to 36 hours ($AUC^{0-36}$) (RDM and KAP) and from zero to 16 hours ($AUC^{0-16}$) (MOR) are the primary test variable for bioavailability.

Secondary variables:

The other derived pharmacokinetic variables were regarded as secondary test variables ($AUC^{0-36}$ (M-6-G, M-3-G), $AUC^{0-\infty}$, $C_{max}$, $T_{max}$, $T_{lag}$, MRT, HVD, $T_{\geq 75}\% C_{max}$, $k_e$).

Safety parameters:

Volunteers were asked to report any changes in normal health to the investigator. The investigator recorded in the CRFs the event, date and time for onset and cessation, frequency, severity, outcome, causality, classification and any action taken.

Trial conductance:

Each volunteer underwent pre-study screening within 4 weeks prior to the first dose of the study medication. The screening included medical history, physical examination and laboratory investigations.

The evening before dosing the volunteer reported to Daw Park Repatriation Hospital at 18.00 hours and was questioned to confirm their eligibility. Further a urine sample was screened for drug abuse.

On the morning of dosing female volunteers underwent a pregnancy test, which had to be negative.

The volunteers had physiological monitoring (pulse rate, blood pressure, respiratory rate and pulse oximetry) pre-dose and at 2, 4, 6, 8, 10, 12, 16, 23 and 36 hours post dosing in periods in which Kapanol® or Repro-Dose® morphine was administered and pre-dose, 0.5, 1, 1.5, 2, 3, 4, 6, 10 and 16 hours after the dose in the period in which Morfin DAK® was given. The volunteers had to stay at Daw Park Repatriation Hospital for 36 hours after dosing. The volunteers had to fast from after supper at 10 pm on the evening before until after the 4 hour sample. Fluid intake from 1 hour before and until 4 hours after dosing was standardised. Meals were standardised for the first 24 hours. In the periods where the two modified release preparations were administered blood samples were obtained just prior to the dose and 1, 2, 3, 4, 5, 6, 7, 8, 10, 12, 16, 23, 27, 31 and 36 hours after the dose. Blood sampling was performed pre-dose and 0.25, 0.5, 0.75, 1, 1.5, 2, 2.5, 3, 4, 5, 6, 8, 10, 12 and 16 hours following the dose in the period where volunteers received the plain morphine tablet. Samples were analysed at PMC in Sweden.

Volunteers had a wash-out period of one week between study periods.

The volunteers underwent a post-study screening including laboratory investigations within 3–10 days of discharge from last study period.

Results of bioavailability study:

In total 26 volunteers were included in the study. Two volunteers dropped out during the first period (RDM and KAP) and were replaced. In total 24 volunteers completed the trial. The 24 volunteers who completed the study were 15 males and 9 females. Their age ranged from 18–38 years with a mean age of 24.1±5.3 years. Their weight ranged from 50–82 kg with a mean weight of 66.1±9.1 kg.

Figure 16:
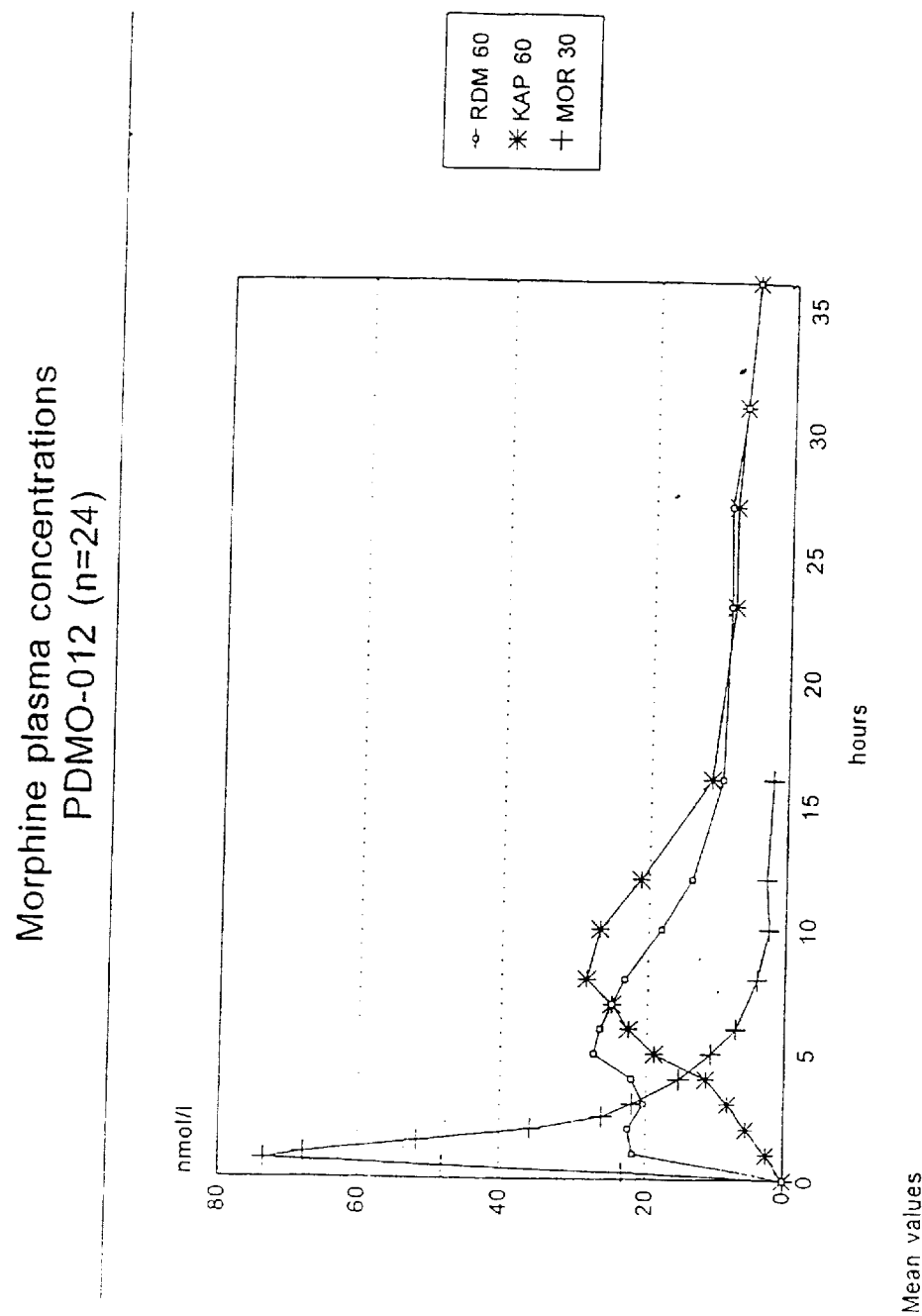
FIG. 16 shows a diagram of morphine plasma concentration after administration of three different morphine composition. For further details see test 1.

The plasma concentration-time curves for morphine are shown in FIG. 16. For morphine the mean±SD $AUC^{0-36}$ (nmol/l×hr) was found to be 467±191 (RDM) and 445±175 (KAP) and $AUC^{0-16}$ was found to be 201±64 (MOR 30 mg) and 402±128 (MOR normalised to 60 mg).

The ratio (%) and the 90% confidence limits for RDM/KAP was 104.1% [97.1;111.6], for RDM/MOR (60) the ratio was 113.0% [105.4;121.1]. RDM is absorbed to the same extent as KAP and slightly more than MOR however both the confidence limits were within the bioequivalence limits 80–125%.

For morphine the mean±SD $C_{max}$ (nmol/l) was determined to be 29.8±12.3 (RDM), 34.4±20.6 (KAP), 84.4±35.0 (MOR 30 mg) and 168.8±69.9 (MOR normalised to 60 mg). The decreased maximum concentrations after RDM and KAP compared to MOR treatment resulted in smoother plasma concentration time curves.

Median (range) $T_{max}$ (hours:min) for morphine was determined to be 5:00 (1:00–8:00) for RDM, 8:00 (1:00–12:00) for KAP and 0:45 (0:15–1:30) for MOR. A significant delay of time to maximum concentration was seen for KAP compared to RDM both of which were considerably delayed compared to MOR.

The results for $T_{lag}$ also showed a slight delay in absorption of KAP when compared with RDM.

The prolonged release profiles of RDM and KAP in comparison to MOR are confirmed by the differences detected in MRT, HVD and $T_{\geq 75 \% Cmax}$ determined for the three preparations.

The pharmacokinetic profiles of the morphine metabolites were as expected from the morphine levels for the three preparations.

Of the 24 volunteers completing the study 16 volunteers reported 38 episodes of adverse events (AEs).

Significantly more volunteers reported adverse events during the KAP period than during the RDM period ($p<0.014$).

The AEs reported in all three treatments were mainly mild, a few moderate and only 2 were reported as severe. The AEs reported as likely to be related to RDM, KAP and MOR were all common and well known AEs after administration of morphine; e.g. vomiting, nausea, headache and dizziness.

None of the pharmacokinetic profiles for the individual volunteers showed evidence of dose dumping secondary to any of the treatments.

No serious AEs and no unexpected AEs occurred.

Conclusion:

The amount of morphine absorbed from RDM is found to be approximately 104% (90% confidence interval 97.1–111.6%) of that absorbed from KAP when the preparations are given as single equal doses in fasting state. The preparations can therefore, be regarded as equivalent (90% confidence interval within 80–125%) under these circumstances.

The plasma profiles for morphine following administration of RDM and KAP demonstrate prolonged absorption and smoother plasma concentration-time curves than that recorded for MOR.

The peak concentration occurs earlier for RDM than for KAP and RDM has a tendency towards being more prolonged than KAP.

Fewer volunteers experienced adverse events with RDM than with KAP.

The pharmacokinetic and the adverse event data reported in this study indicate that RDM may be a valuable formulation for once daily dosing and may offer clinically relevant advantages over KAP.

Figure 17:
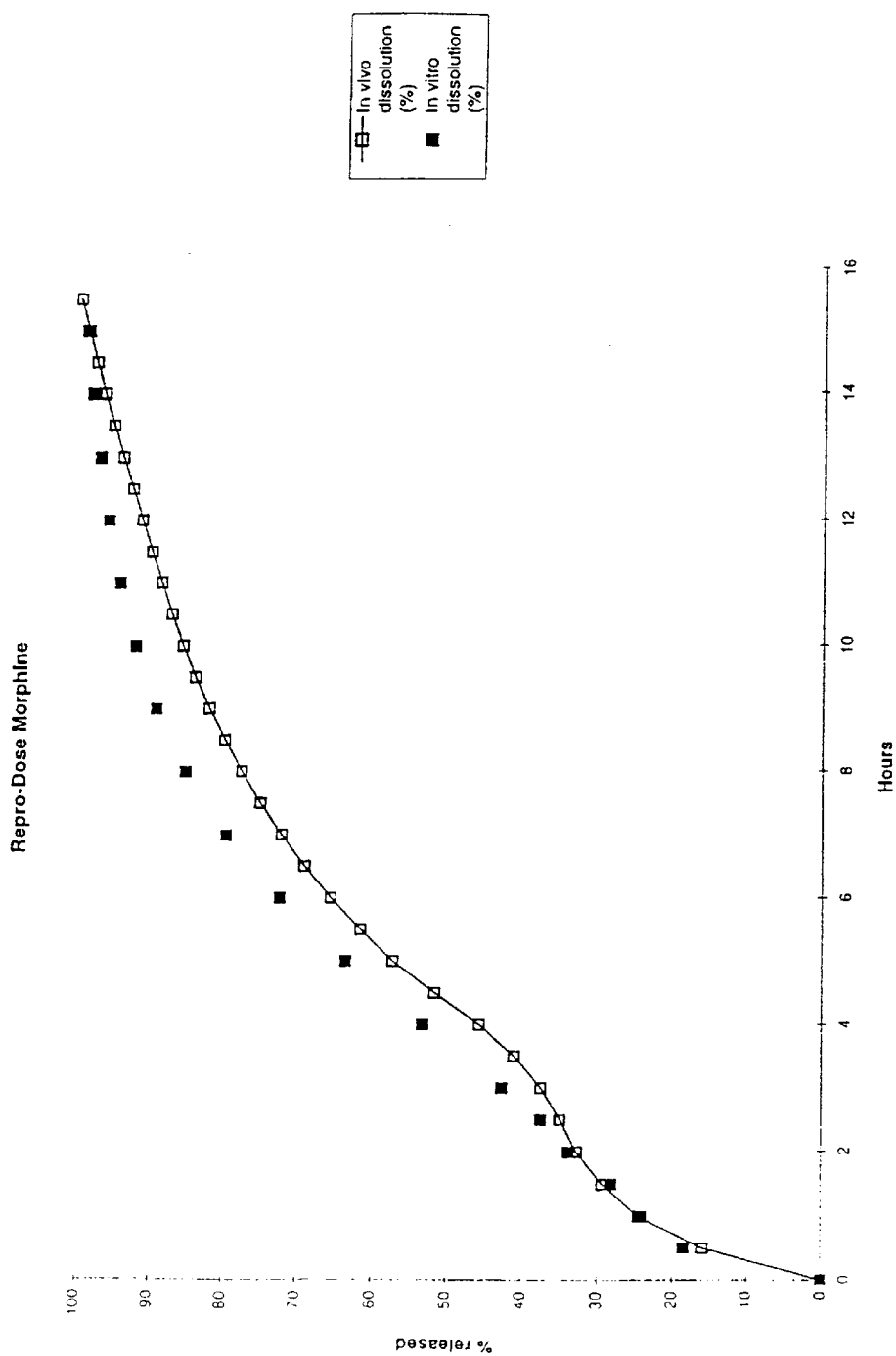
FIG. 17 shows in vivo and in vitro dissolution profiles, respectively, for Repro-Dose® Morphine, cf. test 1.

Results of in vitro—in vivo correlations:

When using deconvolution techniques on the plasma data from RDM and KAP compared with MOR and oral solution data (internal data), in vivo dissolution profiles have been found (FIG. 17). These profiles correlate well with in vitro dissolution data at Level A:

in vivo % released=b×in vitro % released+a

| Preparation | b | a | $R^2$ | N |
|---|---|---|---|---|
| RDM | 0.9535 | −1.0058 | 0.9926 | 19 |
| KAP | 0.6635 | −3.7095 | 0.953 | 5 |

Figure 18:
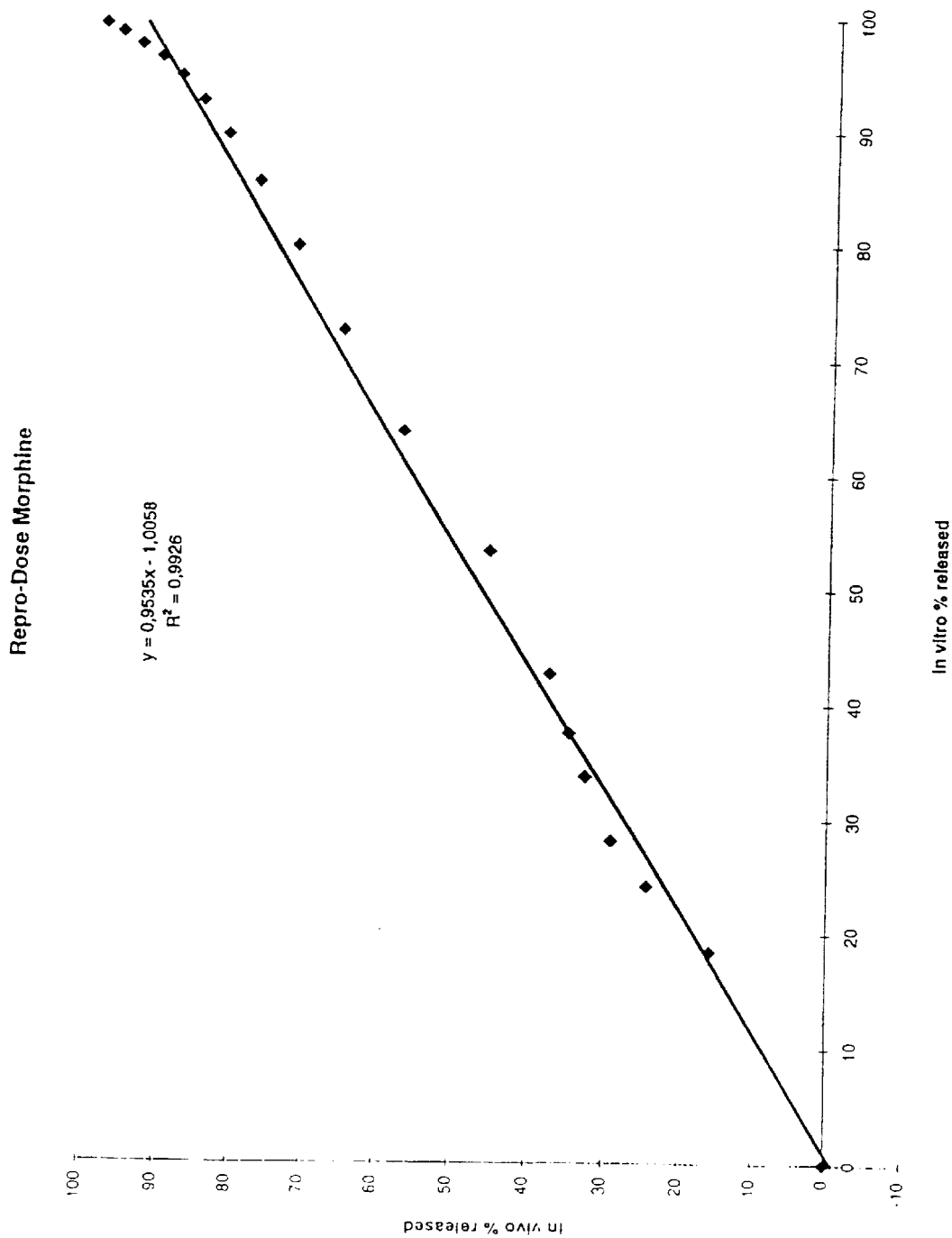
FIG. 18 shows the correlation between the in vitro and in vivo dissolution of Repro-Dose® Morphine, cf. test 1.

These data show a good correlation between in vitro and in vivo dissolution profiles for the RDM preparation (FIG. 18) and a poorer correlation for the KAP preparation.

Figure 19:
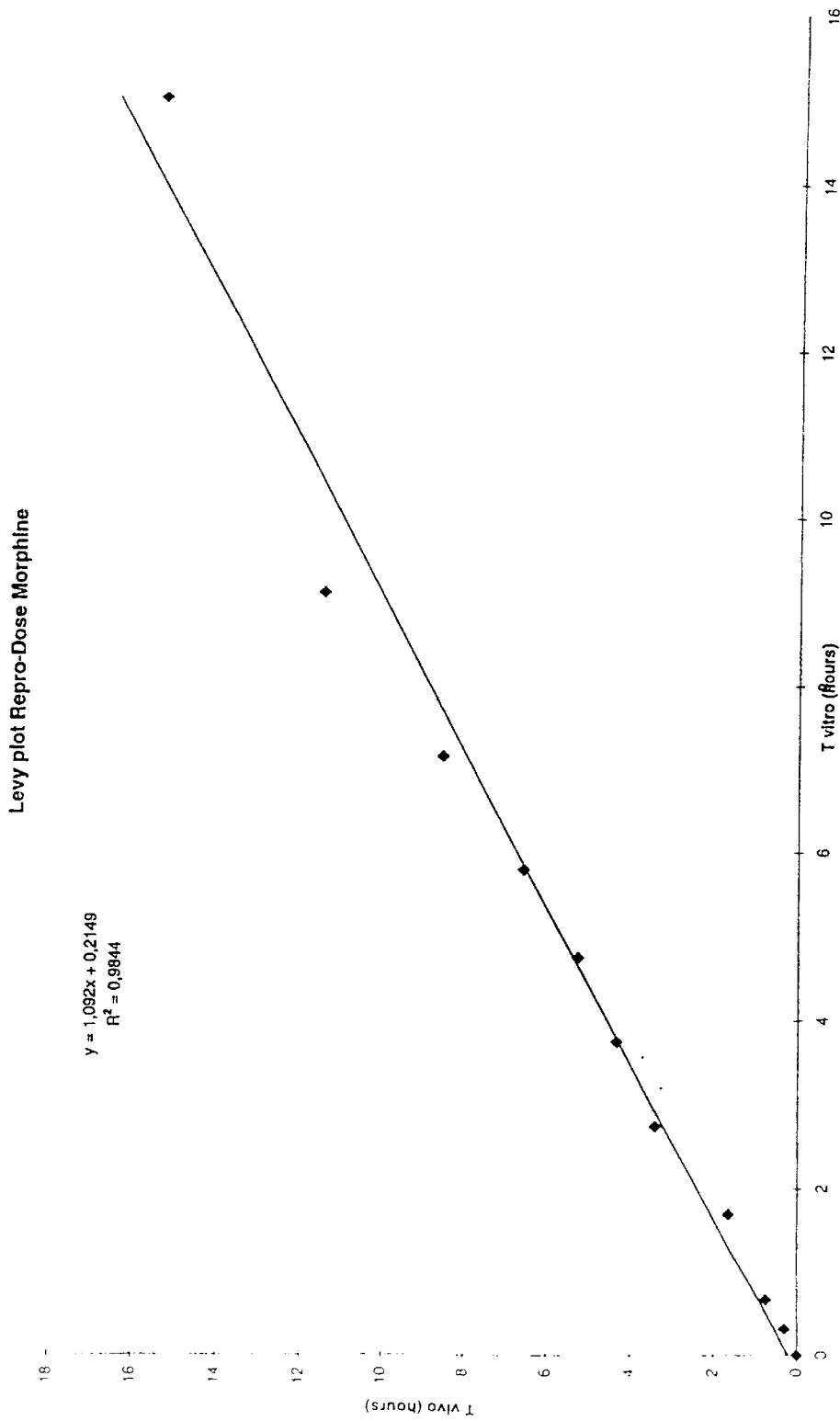
FIG. 19 shows a Levy plot for Repro-Dose® Morphine, cf. test 1.

When using Levy plots (FIG. 19) based on the following formula: T vivo=b×T vitro+a, the correlation are:

| Preparation | b | a | $R^2$ | N |
|---|---|---|---|---|
| RDM | 1.092 | 0.2149 | 0.9844 | 11 |
| KAP | 1.6085 | 0.336 | 0.9966 | 11 |

For both preparations the intercept (a) is close to zero for RDM the slope (b) is close to 1 and for both preparations the correlation coefficients are rather high meaning that the in vitro and in vivo dissolution profiles are very similar and close to a 1:1 correlation.

Figure 20:
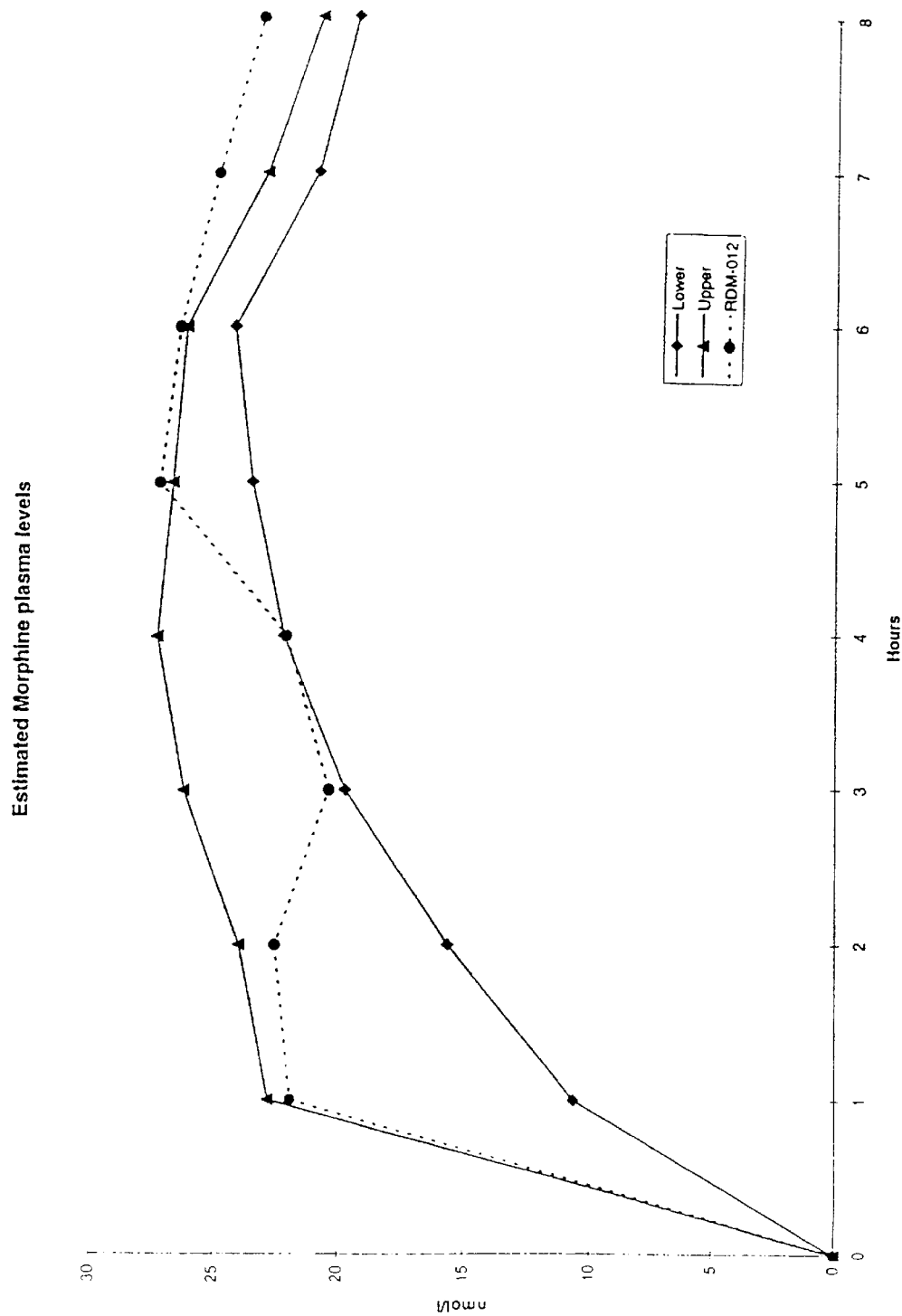
FIG. 20 shows estimated morphine plasma levels; for further details see test 1.

When using convolution techniques on the in vitro dissolution upper and lower specification limits plasma levels can be estimated and surrounds the obtained plasma profiles very nicely for RDM (FIG. 20).

Test 2 (code PDMO-013):

Single dose, open, randomised, four-way cross-over study in healthy volunteers evaluating bioavailability of Repro-Dose® Morphine and MST Continus® with and without food.

Trial Centre: Leicester Clinical Research Centre Limited, 72 Hospital Close, Evington, Leicester, LE5 4WW, United Kingdom Trial objectives:

The aim of the study was i) to compare the bioavailability of Repro-Dose® Morphine to that of MST Continus® in healthy volunteers and ii) to investigate food influence on absorption of Repro-Dose® Morphine and MST Continus® and to evaluate the adverse events reported during the trial period.

Design and number of volunteers:

The study was a single dose, open, randomised, four-way, cross-over study in 16 healthy volunteers. All dropouts and withdrawals were replaced.

Volunteers:

Healthy volunteers of either sex, 18–50 years, weight 55–110 kg, who had given written informed consent. Volunteers who took other medication, who had a drug exposure amounting to drug abuse or addiction, who had made blood donations within 3 months prior to study, who had participated in studies during the last 3 months, who had any history of emotional instability or psychiatric disorder, who were not likely to comply with the protocol, who had received any opioids within 1 year prior to the study, who consumed alcohol which amount to alcohol abuse, who had positive Hepatitis B surface antigen or HIV, who had any allergy or intolerance to the compounds, who had acute or chronic diseases which could influence the health of the volunteer or the study result, who had clinically relevant abnormal laboratory tests or who were pregnant or lactating were not included.

Trial medication:

Repro-Dose® Morphine modified release capsules 30 mg or MST Continus® modified release tablets 30 mg.

Single doses of 60 mg were given with or without standardised breakfast.

Primary variable:

The area under the plasma concentration-time curve of morphine from zero to 36 hours ($AUC^{0-36}$) was the primary test variable for bioavailability.

Secondary variables:

The other derived pharmacokinetic variables were regarded as secondary test variables ($AUC^{0-36}$ (M-6-G, M-3-G), $AUC^{0-\infty}$, $C_{max}$, $T_{max}$, $T_{lag}$, MRT, HVD, $T_{\geq 75\% C_{max}}$, $k_e$).

Safety parameters:

Volunteers were asked to report any changes in normal health to the investigator. The investigator recorded in the CRFs the event, date and time for onset and cessation, frequency, severity, outcome, causality, classification and any action taken.

Trial conductance:

Each volunteer underwent pre-study screening 3 weeks prior to the first dose of the study medication. The screening included medical history, physical examination and laboratory investigations.

The evening before dosing the volunteer reported to LCRC by 19.00 hours and was questioned to confirm their eligibility. Further a urine sample was screened for drug abuse.

On the morning of dosing female volunteers underwent a pregnancy test, which had to be negative.

The volunteers had physiological monitoring (pulse rate, blood pressure and respiratory rate) pre-dose and at 2, 8, 24 and 48 hours post dosing. Further a pulse oximeter were placed on the volunteers during periods of sleep in the first 24 hours post-dose. The volunteers had to stay at LCRC for 48 hours after dosing. The volunteers had to fast from after supper at 10 pm on the evening before until after the 4 hour sample. On the study days with food a standardised breakfast was given no more than 20 minutes before drug intake which took place in the morning together with 240 ml of water. Fluid intake from 1 hour before and until 3 hours after dosing was standardised. Meals were standardised for the first 24 hours. Blood sampling took place at pre-dose (½ hour) and at ½, 1, 1½, 2, 2½, 3, 4, 5, 6, 8, 10, 12, 16, 20, 24, 28 and 36 hours post dosing. Samples were analyzed at PMC, Sweden.

Volunteers had a wash-out period of one week between study periods.

The volunteers underwent a post-study screening including laboratory investigations within 3–10 days of discharge from last study period.

Results:

In total 17 volunteers were included in the study. One volunteer dropped out before dosing and was replaced. In total 16 volunteers completed the trial. The 16 volunteers who completed the study were 9 males and 7 females. Their age ranged from 19–49 years with a mean age of 28.2±8.7 years. Their weight ranged from 54.6–89 kg with a mean weight of 70.8±9.9 kg.

Figure 21:
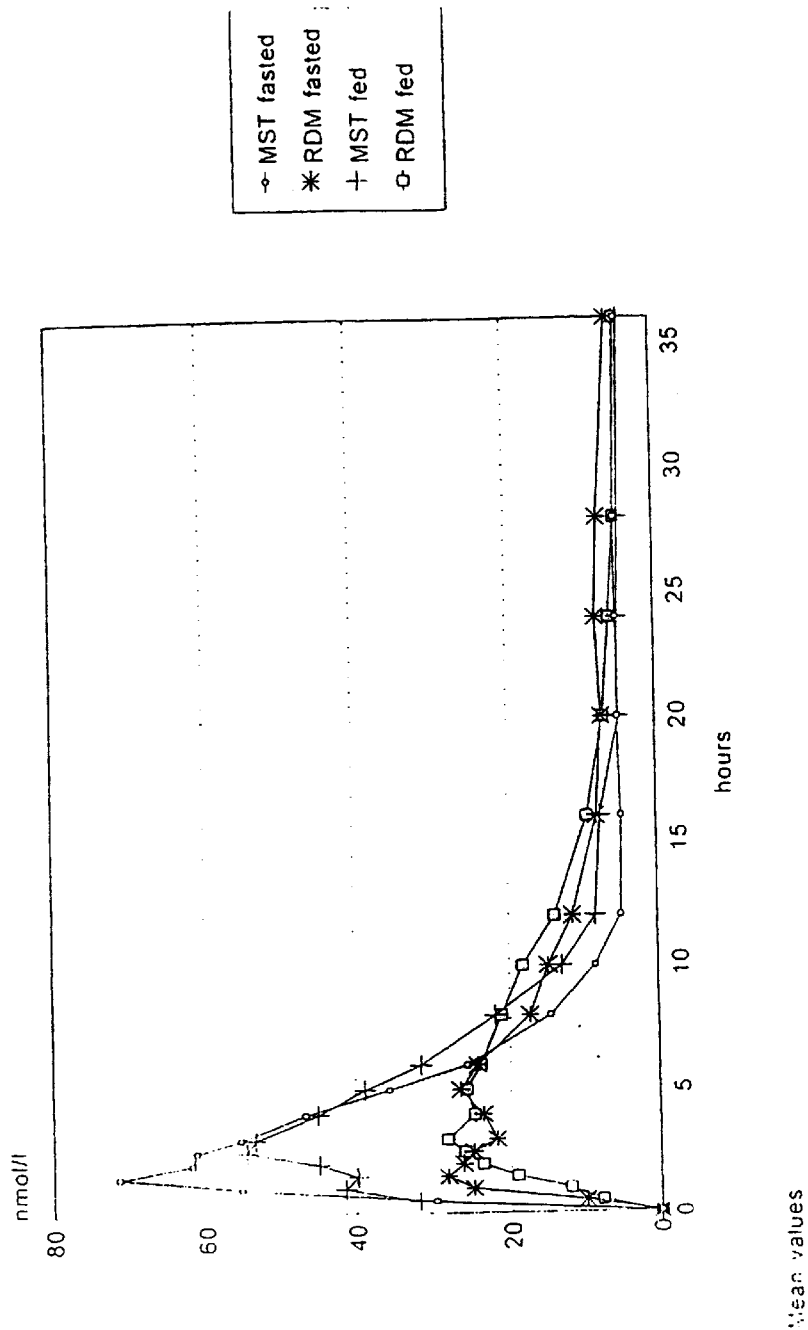
FIG. 21 shows a diagram of morphine plasma concentrations after single dose of a modified release multiple units capsule prepared in accordance with Example 12, referred to as Repro-Dose® Morphine (RDM) and MST Continus® (MST) taken without food (fasted) and with food (fed). Further details appear from test 2.
Figure 22:
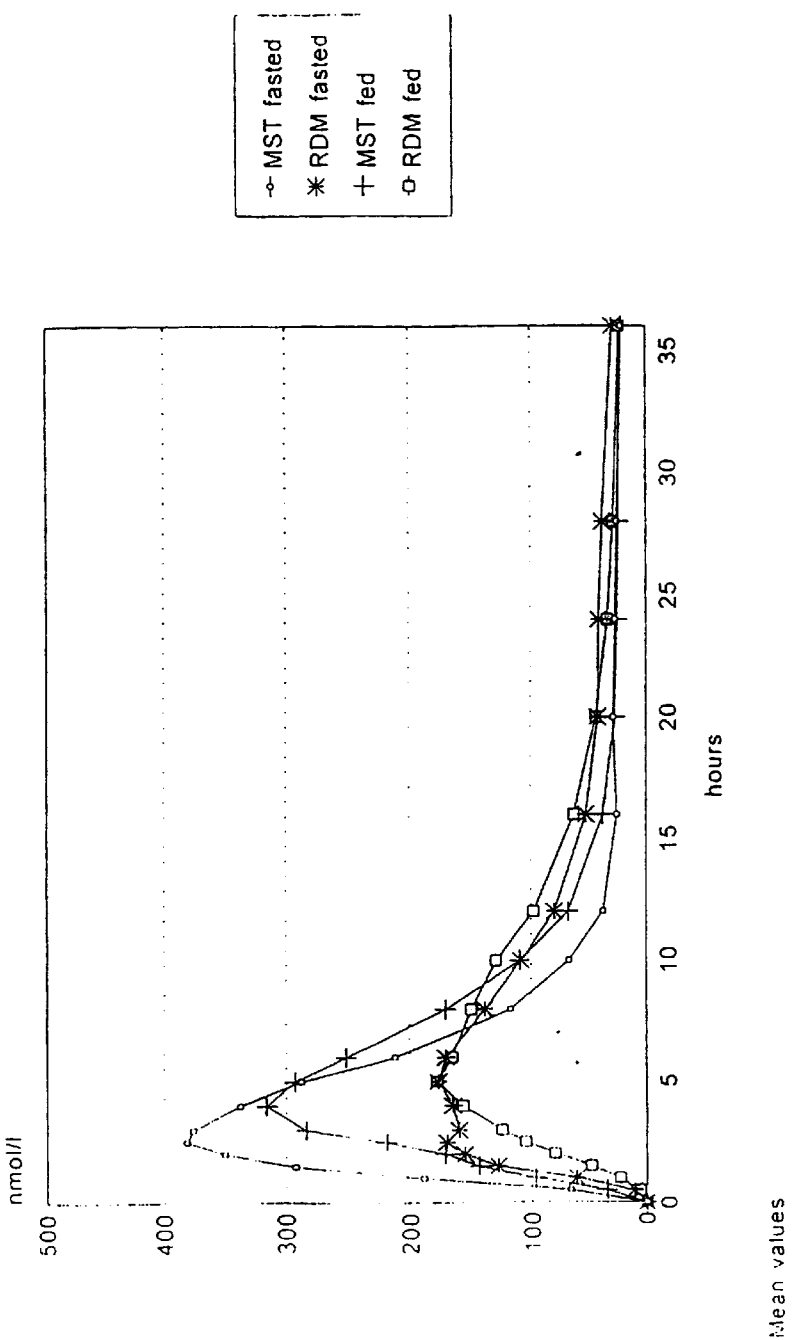
FIG. 22 shows a diagram corresponding to the one shown in FIG. 21, except that morphine-6-glucuronide plasma concentrations are shown.
Figure 23:
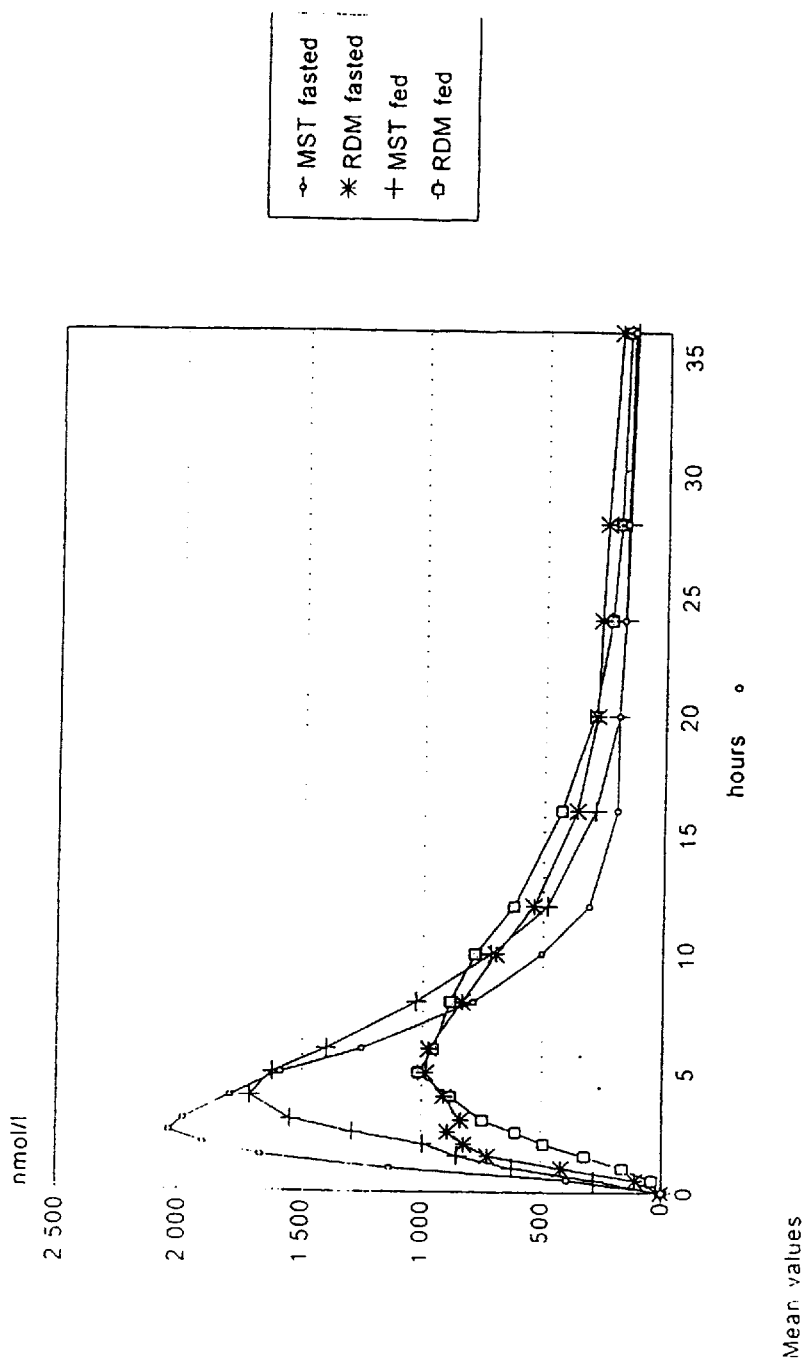
FIG. 23 shows a diagram corresponding to the one shown in FIG. 21, except that morphine-3-glucuronide plasma concentrations are shown.

The plasma concentration-time curves for morphine are shown in FIG. 21. For morphine the mean±SD $AUC^{0-36}$ (nmol/l×hr) was found to be 426×127 (RDM fasted), 416× 116 (RDM fed), 473×138 (MST fasted) and 483×126 (MST fed). The ratio (%) and the 90% confidence limits for RDM/MST was 89.6% [84.1;95.5] (fasted), 86.1% [80.8;91.7] (fed). For the comparison of RDM fed/fasted the ratio was 98.5% [92.5;105.0]. RDM is absorbed to the same extend as MST as judged by the confidence limits being within the bioequivalence limits 80–125%.

For morphine the mean±SD $C_{max}$ (nmol/l) was determined to be 34.2±12.2 (RDM fasted), 33.0±11.7 (RDM fed), 82.8±35.5 (MST fasted) and 68.3±26.6 (MST fed). The decreased maximum concentrations after RDM treatment resulted in smoother plasma concentration time curves.

Median (range) $T_{max}$ (hours:min) for morphine was determined to be 1:48 (1:00–6:00) for RDM fasted, 2:30 (1:00–8:00) for RDM fed, 1:30 (0:30–2:30) for MST fasted and 2:30 (1:00–5:00) for MST fed. A non-significant delay of time to maximum concentration was seen when RDM and MST were administered with food.

The results for $T_{lag}$ also showed a slight delay in absorption of RDM when given with a high fat breakfast.

The prolonged release proffile of RDM in comparison to that of MST is confirmed by the difference detected in MRT, HVD and $T_{\geq 75\%Cmax}$ determined for the two preparations.

No significant food effect for either morphine or the two metabolites was seen for RDM.

The pharmacokinetic profiles of the morphine metabolites were as expected from the morphine levels for the two preparations.

Of the 16 volunteers completing the study 12 volunteers reported 83 episodes of adverse events (AEs). Significantly more volunteers reported adverse events during the MST periods than during the RDM periods in both the fed and fasted states (p<0.046), but there was no difference in the occurrence of adverse events during the fed and fasted periods for RDM.

The AEs reported in all four treatments were mainly mild, a few moderate and only 3 were reported as severe. The AEs reported as likely to be related to RDM and MST were all common and well known AEs after administration of morphine; e.g. Vomiting, nausea, headache and dizziness. A trend towards a lower incidence of drug-related AEs was noted for RDM compared to MST treatments.

None of the pharmacokinetic profiles for the individual volunteers showed evidence of dose dumping secondary to any of the treatments.

No serious AEs and no unexpected AEs occurred.

Conclusions:

The amount of morphine absorbed from RDM is found to be approximately 90% (90% confidence interval 84.1–95.5%) of that absorbed from MST when the two preparations are given as single equal doses in fasting state. The preparations can therefore be regarded as equivalent (90% confidence interval within 80–125%) under these circumstances.

The plasma profile for morphine following administration of RDM demonstrates prolonged absorption and a smoother plasma concentration-time curve than that recorded for MST.

There was no influence of food on the bioavailability of RDM.

Fewer volunteers experienced adverse events with RDM than with MST.

The pharmacokinetic and the adverse event data reported in this study indicate that RDM may be a valuable formulation for once daily dosing and may offer clinically relevant advantages over MST.

Test 3 (code PDMO-018):

Open, randomised, two-way cross-over study in healthy volunteers evaluating bioavailability of Repro-Dose® Morphine once daily and MST Continus® twice daily in steady state.

Trial Centre: Leicester Clinical Research Centre Limited, 72 Hospital Close, Evington, Leicester, LE5 4WW, United Kingdom Trial objectives:

The aim of the study was i) to compare the bioavailability in steady state of Repro-Dose® Morphine once daily to that of MST Continus® twice daily in healthy volunteers, and ii) to evaluate the adverse events reported during the trial period.

Design and number of volunteers:

The study was a multi dose, open, randomised, two-way, cross-over study in 16 healthy volunteers. All dropouts and withdrawals were replaced.

Volunteers:

Healthy volunteers of either sex, 18–50 years, weight 55–110 kg, who had given written informed consent. Volunteers who took other medication, who had a drug exposure amounting to drug abuse or addiction, who had made blood donations within 3 months prior to study, who had participated in studies during the last 3 months, who had any history of emotional instability or psychiatric disorder, who were not likely to comply with the protocol, who had received any opioids within 1 year prior to the study, who consumed alcohol which amount to alcohol abuse, who had positive Hepatitis B or C surface antigen or HIV, who had any allergy or intolerance to the compounds, who had acute or chronic diseases which could influence the health of the volunteer or the study result, who had clinically relevant abnormal laboratory tests or who were pregnant or lactating were not included.

Trial medication:

Repro-Dose® Morphine modified release capsules 30 mg or MST Continus® modified release tablets 30 mg.

Single doses of 60 mg of Repro-Dose® Morphine were given every morning for 5 days.

Single doses of 30 mg of MST Continus® were given every morning and evening for 5 days.

Primary variable:

The area under the plasma concentration-time curve of morphine from zero to 24 hours ($AUC^{0-24}$) was the primary test variable for bioavailability.

Secondary variables:

The other derived pharmacokinetic variables were regarded as secondary test variables ($AUC^{0-24}$ (M-6-G, M-3-G), $AUC^{0-12}$, $AUC^{12-24}$, $C_{max}$, $C_{min}$, $C_{trough}$, $C_{av}$, % PTF, $T_{max}$, HVD, $T_{\geq 75\% C_{max}}$).

Safety parameters:

Volunteers were asked to report any changes in normal health to the investigator. The investigator recorded in the CRFs the event, date and time for onset and cessation, frequency, severity, outcome, causality, classification and any action taken.

Trial conductance:

Each volunteer underwent pre-study screening within 3 weeks prior to the first dose of the study medication. The screening included medical history, physical examination and laboratory investigations.

All volunteers reported to Leicester Clinical Research Centre by 26 hours before the first morphine dosing in each period and were questioned to confirm their eligibility. Further a urine sample was screened for drug abuse and pregnancy test was performed for female volunteers. If negative drugs of abuse and pregnancy test the volunteers were challenged in the first period only with a direct i.v. injection of about 0.5 ml naloxone 0.4 mg/ml (Narcan®). If no adverse events occurred from the challenge after at least 15–20 minutes, 2 naltrexone tablets were given orally (100 mg) approximately 24 hours before the first morphine dose.

The volunteers had physiological monitoring (pulse rate, blood pressure and respiratory rate) pre-dose and at 2 and 8 hours post morning dosing on day 1 and at 4 hours post morning dosing on day 2–5. Further a pulse oximeter were placed on the volunteers during periods of sleep every night until 24 hours after last morning dose in each period. The volunteers had to stay at LCRC for 48 hours after the last morning dose. Repro-Dose® Morphine was given in the morning and MST Continus® in the morning and in the evening (on day 5 after the 12 hour sample point). Naltrexone was given within 24 hours of each of the morphine doses and at 24 hours after the last morphine dose. Naltrexone and morphine doses were separated by at least 60 minutes. The volunteers had to fast from after supper at 10 pm on the evening (day 4) before sampling (day 5), until after completion of the 4 hour post dose sample point. The volunteers fasted from 10 hour to 16 hour sample where a light snack was served. Breakfast next morning was given after the 24 hour sample point. The meals were standardised throughout both study periods. On day 5 fluid intake was not allowed from 1 hour before morning dose to 1 hour after dosing and again from 1 hour before evening dose to 1 hour after dosing, except the 240 ml water which had to be taken together with the morphine dose. On day 3 and 4 blood sampling took place immediately before the morning dose in each study period. On day 5 blood sampling took place at pre-dose (0 hour) and at 1, 2, 4, 6, 8, 10, 12, 13, 14, 16, 18, 20, 22 and 24 hours post morning dose. Samples were analyzed at Department of Drug Disposition, Linz.

Volunteers had a wash-out period of two weeks between study periods.

The volunteers underwent a post-study screening including laboratory investigations within 3–10 days of discharge from last study period.

Results:

19 volunteers were included in the study. Three volunteers dropped out, one after naltrexone/naloxone, but before trial drugs and 2 in the MST period. All three volunteers were replaced. In total 16 volunteers completed the trial. The 16 volunteers who completed the study were 9 males and 7 females. Their age ranged from 22–46 years with a mean age of 31.4±7.2 years. Their weight ranged from 55.0–88.6 kg with a mean weight of 68.4±10.1 kg.

The mean trough concentrations $C_{trough}$ day 3–5 indicated that steady state level was achieved for both treatment periods.

Figure 24:
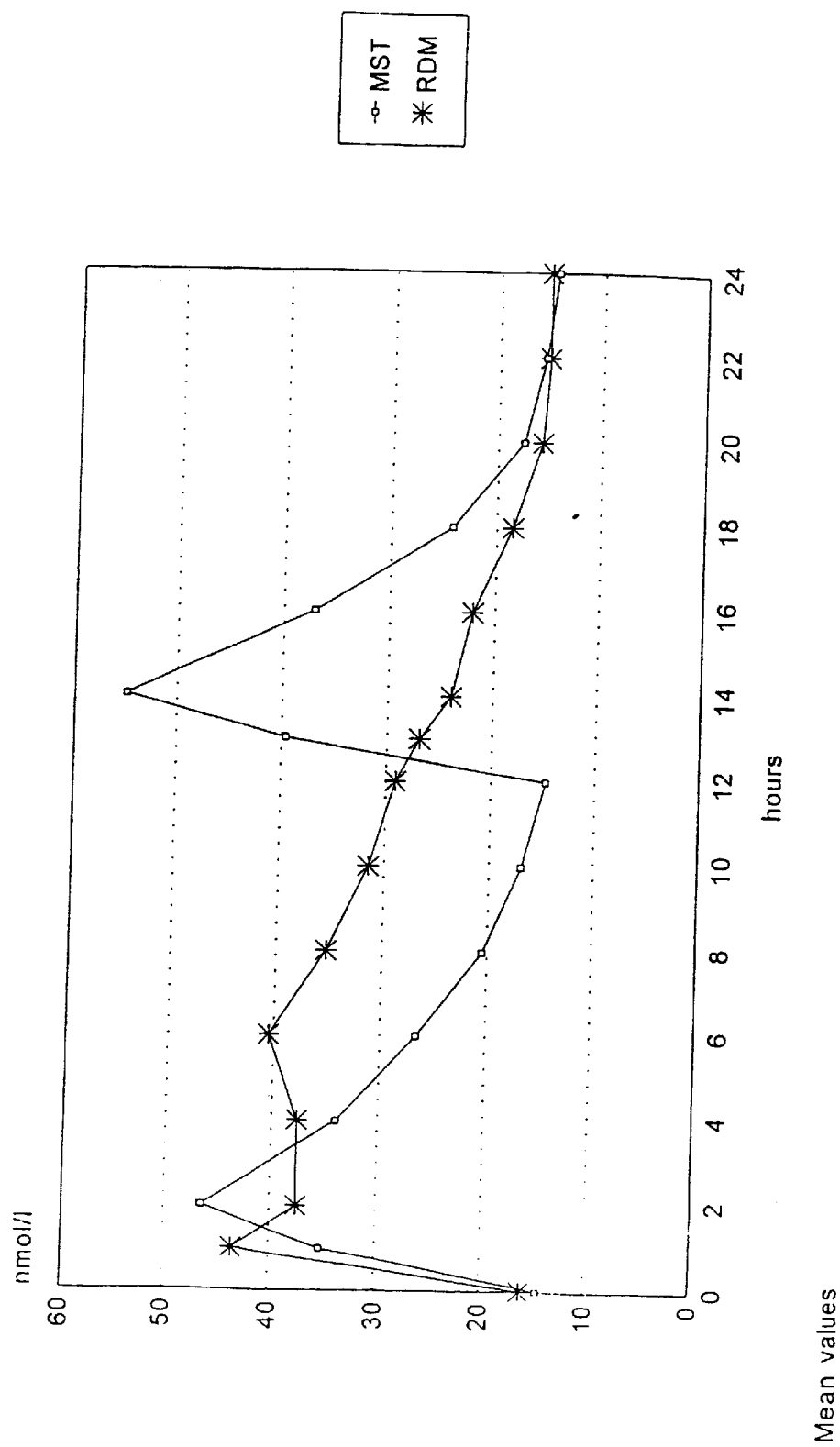
FIG. 24 shows a diagram of morphine plasma concentrations after administration of two different morphine composition, cf. test 3.

The plasma concentration-time curves for morphine are shown in FIG. 24. The mean $AUC^{0-24}$ for both preparations was 657 nmol/l×h with regard to morphine. The ratio found by pairwise comparison was 101% with confidence limits of 92–111%. Equivalence with regard to $AUC^{0-24}$ was also found for the metabolites (90% confidence interval within 80–125%).

The $AUC^{0-12}$ was higher for RDM compared to MST for all three analytes. On the contrary, the area under the curve was higher for MST in the 12 to 24 hour interval.

$C_{max}$ obtained for the RDM and MST respectively were 50±20 and 62±30 nmol/l. Equivalence with regard to this parameter was not found. Higher peak plasma concentrations for MST were also found for the metabolites.

The median $T_{max}$ occurred 1.5 hours later in the RDM period; MST reaching peak level after median 2 hours.

The fluctuations of morphine in the RDM and MST periods were 135% and 184%, respectively. The fluctuations for M-6-G and M-3-G were also more pronounced in the MST period.

The morphine HVD for RDM (14.1 hours) was twice the HVD for MST (7.3 hours). Supportive data with regard to $T_{\geq 75\% C_{max}}$ was found for morphine 6.5 hours (RDM) and 3.3 hours (MST) respectively. Results for the metabolites with respect to these parameters were consistent with the results for morphine.

Of the 19 volunteers entering the study 14 volunteers reported 44 episodes of adverse events (AEs); 13 AEs (RDM), 14 AEs (MST), 13 AEs (naltrexone) and 4 AEs (pre-or post study).

No significant difference in number of volunteers reporting AEs was found between the RDM and MST treatments.

The AEs reported were predominantly mild and the majority had character of opioid side effects, especially GI-system disorders. The safety profile for the MST treatment tended to be no different from that seen for RDM, although fewer AEs were reported for RDM. In contrast to the MST period, no psychiatric disorders were reported in the RDM period. Further, more cases of vomiting were reported in the MST period. None of the pharmacokinetic profiles for the individual volunteers showed evidence of dose dumping from any of the treatments.

No serious or unexpected AEs occurred.

Conclusions:

The study demonstrated that chronic dosing with RDM given once daily and MST dosed twice daily were equivalent with regard to the $AUC^{0-24}$ for both morphine and its metabolites (M-6-G and M-3-G) in steady state conditions. Although the RDM treatment resulted in lower $C_{max}$ which occurred later than $C_{max}$ for MST, the RDM formulation gave initial plasma concentrations comparable to the concentrations in the MST period. However, the RDM formulation extended the release of morphine and thus gave rise to a smoother and more prolonged plasma profile. Furthermore the RDM formulation successfully minimized the fluctuation during the 24 hour dosing interval compared to MST. These features indicate that RDM may offer significant clinical advantages over MST and enable a once daily regimen to be used.

In this study naltrexone was used to antagonize the possible side effects of chronic morphine treatment. This treatment made a volunteer study safe. No serious or unexpected AEs were reported. The safety profile for the two treatment periods were indistinguishable.

Test 4 (code PDMO-001):

A randomised, double-blind, cross-over study evaluating efficacy and bioavailability in chronic pain patients treated with Repro-Dose® Morphine and MST Continus® in steady state.

Trial centres: King's College Hospital, Denmark Hill, London SE5 9RS, United Kingdom, St. Christopher's Hospice, 51-59 Lawrie Park Road, Sydenham, London SE 26, United Kingdom and St. Francis' Hospice, The Hall, Broxhill Road, Havering-atte-Bower, Romford, Essex, United Kingdom.

Trial objectives:

The aim of the study was i) to investigate the analgesic efficacy and adverse drug reaction profile of Repro-Dose®

Morphine in comparison to that of MST Continus® in patients with stable opioid responsive chronic pain, and ii) to investigate the pharmacokinetic profile of Repro-Dose® Morphine in comparison to that of MST Continus®.

Design and number of patients:

The study was a cross-over study, and 40 patients were randomly allocated to one of the treatment groups below after a 5-day screening period. Drop-outs and withdrawals were replaced.

Group A: MST Continus® for 5 days followed by Repro-Dose® Morphine for 5 days. Group B: Repro-Dose® Morphine for 5 days followed by MST Continus® for 5 days.

The two treatments were given in daily doses of: 20, 40, 60, 90 or 120 mg.

Up to 10 patients with daily morphine requirements of 40, 60, 90 or 120 mg was included in the pharmacokinetic part of the study.

Patients:

Patients included in this trial were in- and outpatients suffering from pain secondary to cancer, severe vascular disease or other chronic pain requiring chronic morphine treatment. They were males and females of at least 18 years of age, and the body weight for patients included in the pharmacokinetic part was between 40–90 kg. They should be receiving MST Continus® at stable doses during the 5-day screening period prior to inclusion. Their morphine requirement should be 20, 40, 60, 90 or 120 mg daily during the trial period. Patients were allowed to take other medication to obtain pain relief (e.g. NSAIDs, corticosteroids, anticonvulsants, tricyclic antidepressants), but this medication should be taken in stable doses during the screening period and during the trial. Other concomitant treatment (e.g. radiotherapy, chemotherapy) was not allowed. Patients suffering from gastrointestinal diseases or with decreased liver and/or kidney function were excluded from this study as this may influence the absorption, metabolism and/or excretion of the drug. Pregnant or lactating females were excluded from the trial.

Trial medication:

The Repro-Dose® Morphine modified release capsules in daily doses of 20, 40, 60, 90 or 120 mg once daily was to be compared to MST Continus® modified release tablets twice daily in the mentioned daily doses. MST Continus® was, however, dosed as 10, 20, 30, 45 or 60 mg twice daily.

Both preparations were encapsulated in red gelatine capsules and given orally.

Escape medication was provided as Palfium (dextromoramide) tablets 5 mg.

Primary efficacy variable:

The primary efficacy variable for this trial was the number of treatment failures. A patient was considered a treatment failure if he/she consumed more escape medication during the last three days of the Repro-Dose® Morphine period of the trial than during the last three days of the MST Continus® period.

Secondary efficacy variables:

The secondary variables to be evaluated were: Time until first escape medication after each dosing (morning, evening) for the last three days of each period, mean pain intensity score the last three days of each of the periods, patients' overall assessment for each of the treatments, patients' preference for either of the treatment periods.

Safety parameters:

Patients were asked every evening by the investigator whether or not they had experienced and noted any adverse events. If the answer was positive the investigator recorded the type, severity, duration, outcome, adjuvant treatment and recorded the relation to the trial medication on an adverse event form.

Trial conductance:

Five days prior to inclusion patients were screened for the trial and given written and oral information concerning the trial. If, following the screening period, the patient wished to be included in the trial he/she was asked to give his/her written consent. At this screening visit patients' demographic data, medical history, co-medication, site of pain and determination of liver and kidney function after blood sampling were recorded.

During the 5-day screening period the patient's pain intensity and medication was monitored by the investigator, and if it remained stable, the patient was eligible for the study.

At day 0 patients were included in the study, given trial medication and escape medication (Palfium tablets) for the following 5 days.

On day 5 patients switched to the opposite treatment and returned all remaining medication (incl. escape medication) for the former 5 days.

During the entire study period patients assessed their pain intensity twice daily before consumption of trial medication and in the evening record in their diary whether or not they had experienced an adverse event.

At the end of each of the treatment periods patients assessed their overall opinion of the treatment, and in the end of the trial they gave their preference to either of the treatments, if possible.

On day 10 (at the end of the study) patients' total bilirubin and s-creatinine concentrations were determined to evaluate whether the patients' liver and kidney function had been stable during the study period.

Patients participating in the pharmacokinetic part of the study had blood samples taken during a 24 hour period on day 4–5 and 9–10. Furthermore, urine for these 24-hour periods was collected.

Results—clinical part:

The study was conducted from 19 February 1994 to 8 February 1996. A total number of 55 patients were screened, and 47 patients were included. Forty patients were evaluated in the intent-to-treat (ITT) population and 31 patients in the per-protocol population. The ITT population consisted of 19 males and 21 females; 30 were cancer patients and 10 non-cancer patients; mean age 68.3 years (range 42.5–86.3), and mean weight 63.9 kg (±12.1). Seven patients dropped out or were withdrawn from the study including 3 patients who dropped out because of AEs, 1 because of lack of effect, 2 because of problems with trial medication, and 1 because of concomitant disease. Analysis was performed regarding the data as from a single centre using data from all dose levels given.

Fourteen (35%) patients consumed less Palfium in the RDM period than in the MST period and 15 (38%) consumed equal amounts in both periods. In total 29 (72.5%) patients (95% confidence interval 56.1–85.4%) were treatment successes. That is that at least 56% of the patients did not need any escape medication at all, or needed less than or equal amounts of escape medication in the RDM period compared to the MST period and can be regarded as treatment successes at the 97.5% confidence level.

Twenty-five (63%) patients took escape medication during the last 3 days of the RDM period and 27 (68%) patients in the MST period. The difference between the percentage of patients who took escape medication during the two treatment periods was not significant.

In the last 3 days of the RDM period median time to first escape medication was between 22 and 25 hours. In the last 3 days of the MST period median time to first escape medication was between 10 and 13 hours in the night intervals and 13 hours in all day intervals.

Figure 25:
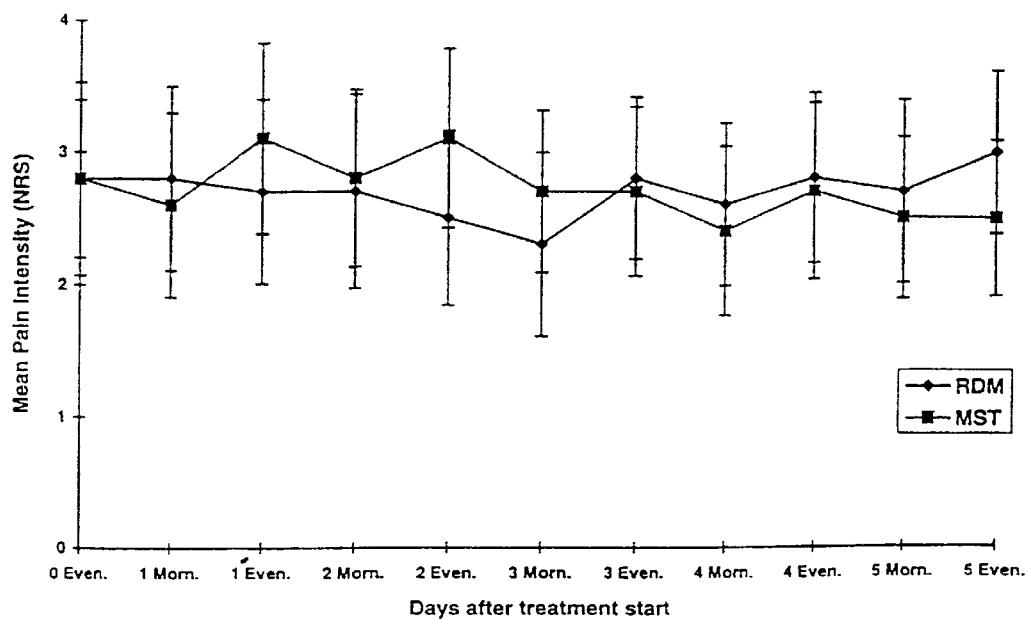
FIG. 25 shows a diagram of mean pain intensity; for further details see test 3.

Mean pain intensity (Numerical Rating Scale) and 90% confidence interval over the last 3 treatment days was 2.7 (2.2–3.2) in the RDM period and 2.5 (2.0–3.1) in the MST period (FIG. 25). There was no significant difference between mean pain intensity in the two treatment periods.

Mean overall assessment±standard deviation was 3.2±0.9 in the RDM period and 3.0±0.9 in the MST period. There was no difference in patients' overall assessment of the treatments.

Figure 26:
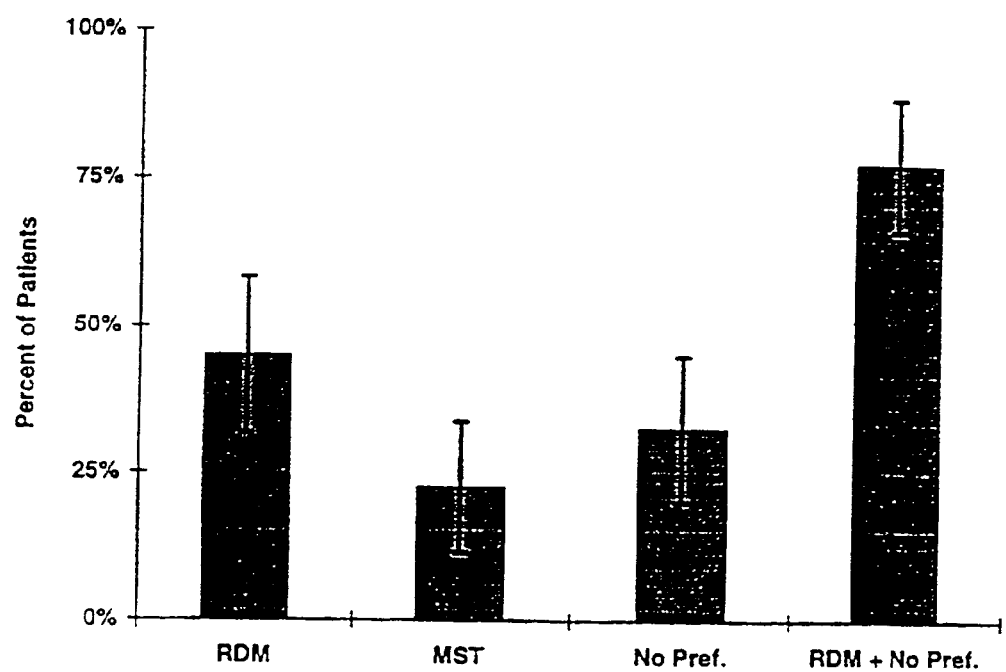
FIG. 26 shows an effect evaluation of treatment preference, cf. test 3.

Eighteen (45%) patients had a preference for the RDM treatment period, 9 (22.5%) patients for the MST period and 13 (32.5%) patients had no preference (FIG. 26). The percentage of patients preferring EDM treatment plus those who had no preference was significantly higher than the percentage of patients who preferred MST treatment (p=0.0003).

No dose-effect was seen for the various dose levels in this study.

Thirty-eight of 47 included patients reported a total of 158 adverse events (AEs), of which 42 AEs were reported by patients who dropped out or were withdrawn. In total 116 AEs were reported by 31 patients in the intent-to-treat population, including 24 patients who reported 56 AEs in the RDM period and 26 patients who reported 60 AEs in the MST period.

No SAEs occurred during the trial periods. Two SAEs occurred during the RDM follow-up treatment; none of which were drug-related.

The AEs reported by patients were well-known opioid or disease related events. A considerable proportion of the reported AEs was considered unlikely to be related to the trial drug. The AEs were mainly mild or moderate, and few severe. The AEs were evenly distributed between treatments. The most common AEs were nausea and vomiting.
Conclusions—clinical part:

The results indicate that RDM administered once daily is as efficacious and as well tolerated as an equal dose of MST administered in two divided doses.

RDM once daily was preferred by more patients than MST twice daily.

The consistency of the data obtained in this study indicate that the design used is valid for this type of efficacy study, and has considerable power. There was a good correlation between relevant parameters used to assess efficacy.

The safety profile of RDM is similar to that of MST.

All AEs classified as drug-related have previously been described for morphine treatment. No SAEs were seen during the trial periods. During the RDM follow-up treatment 2 SAEs were seen, none of which were drug-related.
Results—pharmacokinetic part:

The first patient was included 28 January and the study is still ongoing. The last patient included in the data lists completed May 22, 1996. Five patients were included in the interim clinical trial report, 4 of whom completed the study. Samples for one of the completed patients have not been analyzed yet. All patients included were male in the range of 55–72 years of age (p 8), weight 50–68 kg. One patient dropped out because he stopped taking the trial medication.

All patients had the same overall assessments for RDM and MST. One patient preferred RDM, the others had no preference.

The following ratios (RDM/MST) for patient Nos. 137, 140, and 155, respectively, were calculated: $AUC^{0-24}$ (0.86; 0.85; 0.84), $AUC^{0-12}$ (1.22; 1.51; 1.18), $AUC^{12-24}$ (0.47; 0.47; 0.58), $C_{max}$ (0.83; 0.72; 0.60), $C_{min}$ (0.89; 1.98; 0.57), $C_{trough}$ (0.78; 1.38; 0.62), fluctuation index (0.95; 0.72; 0.72), and Xu total (1.63; 0.83; 0.68).

The following differences in hours (RDM-MST) for patient Nos. 137, 140, and 155, respectively, were calculated: $T_{max}$ (0; −3; −2), HVD (5.45; −0.63; 1.93), and $T_{\geq 75\%Cmax}$ (3.53; −1.88; −5.03).

Four patients reported 23 episodes of adverse events (AEs). Three of the patients who completed the study reported 20 AEs, including 2 patients who reported 10 AEs in the RDM period and 3 patients who reported 10 AEs in the MST period.

No SAEs occurred during this part of the study.
Test 5 (code PDMO-009):

A randomised, double-blind, three-way, cross-over study evaluating the efficacy and the bioavailability in chronic pain patients treated with Repro-Dose® Morphine and Contalgin® in steady state.

Trial centre: Geriatric Treatment Centre, Tranehaven, Schioldannsvej 31, DK-2920 Charlottenlund, Denmark.
Trial objectives:

The aim of the study is i) to investigate the analgesic efficacy and adverse drug reaction proffie of Repro-Dose® Morphine administered once or twice daily in comparison to that of Contalgin® administered twice daily in patients with stable opioid responsive chronic pain, and ii) to investigate the pharmacokinetic profile of Repro-Dose® Morphine in comparison to that of Contalgin® in the mentioned dosage regimen.
Design and number of patients:

The study is a three way cross-over study, and 42 patients are randomly allocated to one of the treatment sequences below after a 5-day screening period. Drop-outs and withdrawals will be replaced.

Each of the mentioned treatments are administered during a five days period:
A-B-C
A-C-B
B-A-C
B-C-A
C-A-B
C-B-A Treatment A: Contalgin®. Half the daily dose of morphine is given in the morning and half the daily dose in the evening.

Treatment B: Repro-Dose® Morphine (once daily dosage). The total daily dose of morphine is given in the evening while placebo capsules are given in the morning.

Treatment C: Repro-Dose® Morphine (twice daily dosage). Half the daily dose of morphine is given in the morning and half the daily dose in the evening.

The three treatments are given in daily doses of: 20, 40, 60, 80 or 120 mg.

Eighteen of the included patients whose daily morphine requirement are 60, 80 or 120 mg will be included in the pharmacokinetic part of the study.
Patients:

Patients included in this trial are in- and outpatients suffering from chronic morphine requiring pain secondary to osteoarthritis, rheumatoid arthritis and prostatic cancer. They are males and females of at least 18 years of age, and the body weight for patients included in the pharmacokinetic part is between 40–100 kg. They should be receiving Doltard® or Contalgin® at stable doses during the 5-day screening period prior to inclusion. Their morphine requirement should be 20, 40, 60, 80 or 120 mg daily during the trial period. Patients are allowed to take medication other than opioids to obtain pain relief (e.g. NSAIDs, corticosteroids, anticonvulsants, tricyclic antidepressants) and disease modifying agents (DMARDs incl. corticosteroids), but this medication should be taken in stable doses during the screening period and during the trial. Other concomitant treatment (e.g. radiotherapy, chemotherapy) is not allowed. Patients suffering from gastrointestinal diseases or with decreased liver and/or kidney function are excluded from this study as this may influence the absorption, metabolism and/or excretion of the drug.

Trial medication:

The Repro-Dose® Morphine modified release capsules in daily doses of 20, 40, 60, 80 or 120 mg (administered once or twice daily) is to be compared to Contalgin® modified release tablets twice daily in the mentioned daily doses. Contalgin® will however be dosed as 10, 20, 30, 40 or 60 mg twice daily. Both preparations are encapsulated in red gelatine capsules and given orally. Escape medication will be provided as Palfium (dextromoramide) tablets 5 mg.

Primary efficacy variable:

The primary efficacy variable of Repro-Dose® Morphine (once daily) will be the number of treatment failures. A patient is considered a treatment failure if he/she consumes more escape medication during the last three days of the Repro-Dose® Morphine (once daily) period of the trial than during the last three days of the Contalgin® period.

Primary efficacy variable of Repro-Dose® Morphine (twice daily) will be consumption of escape medication in the last three days of the Repro-Dose® Morphine (twice daily) period compared with the consumption of escape medication in the last three days of the Contalgin® period.

Secondary efficacy variables:

The secondary variables to be evaluated are: Time until first escape medication after each dosing (morning, evening) for the last three days in each period, mean pain intensity score the last three days of each of the periods, patients' and investigator's overall assessment for each of the treatments and patients' and investigator's preference for either of the treatment periods, if possible.

Safety parameters:

Patients will be asked every evening by the investigator whether or not they have experienced and noted any adverse events. If the answer is positive the investigator will record the event, severity, duration, outcome, intensity and record the relation to the trial medication on an adverse event form.

Trial conductance:

Five days prior to inclusion patients will be screened for the trial and given written and oral information concerning the trial. If the patient wishes to be included in the trial he/she will be asked to give his/her written consent. At this screening visit patients' demographic data, medical history, co-medication, reason for morphine treatment and determination of liver and kidney function after blood sampling will be recorded.

During the 5-day screening period the patient's pain intensity and medication will be monitored by the investigator, and if it remains stable, the patient will be eligible for the study.

At day 0 patients are included in the study, given trial medication and escape medication (Palfium tablets) for the following 5 days.

On day 5 and day 10 patients will switch to the next treatment in the sequence and return all remaining medication (incl. escape medication) for the former 5 days.

During the entire study period patients will assess their pain intensity twice daily before consumption of trial medication and in the evening record in their diary whether or not they have experienced and adverse event.

At the end of each of the treatment periods patients and investigator will assess their overall opinion of the treatment, and in the end of the trial they will give their preference to either of the three treatments, if possible.

On day 15 (at the end of the study) patients' total bilirubin and s-creatinine concentrations will be determined to evaluate whether the patients' liver and kidney function has been stable during the study period.

Patients also participating in the pharmacokinetic part of the study will have blood samples taken during a 24 hour period on day 4–5, 9–10 and 14–15. Furthermore urine for these 24-hour periods will be collected.

Repro-Dose® Morohin—overall conclusion

Clinical results show that Repro-Dose® Morphine has a more prolonged plasma profile than MST Continus® and at the same time provide early plasma concentrations to secure a clinical effect. A comparison between Repro-Dose® Morphine once daily and MST Continus® twice daily in chronic pain patients shows efficacy and safety of the two treatment regimens. However, more patients preferred the Repro-Dose® period even though it was a blinded study where they were dosed twice daily (Placebo in the morning). When given once daily even more patients may prefer Repro-Dose® Morphine due to more convenience in the treatment regimen and a higher compliance may be expected.

Compared to Kapanol®, Repro-Dose® morphine shows equal prolongation in plasma profile but earlier peak concentration, which may be an advantage to avoid break through pain.

What is claimed is:

1. An oral pharmaceutical modified release multiple-units composition for the administration of analgesically effective amount of an opioid to obtain both a relatively fast onset of the analgesic effect and the maintenance of an analgesically active plasma concentration for at least 12 hours, a unit dosage of the composition comprising at least two fractions of multiple-units as follows:

a first fraction of modified release coated multiple-units that comprise a coating of a substantially water insoluble material for relatively fast release in vivo of an opioid to obtain a therapeutically active plasma concentration within a relative short period of time, and a second fraction of modified release coated multiple-units for delayed release in vivo of an opioid to maintain an analgesically active plasma concentration for a period of at least 12 hours, the formulation of the first and the second fractions, with respect to modified release therefrom and with respect to the ratio between the first and the second fraction in the unit dosage, being adapted so as to obtain:

i) a relative fast in vitro release of the opioid from the first fraction of modified release multiple-units, as measured by a dissolution method employing a USP/Ph.Eur. dissolution apparatus equipped with a paddle, a rotation speed of 1000 rpm and 0.1 N HCl as dissolution medium, ii) a delayed in vitro release of the opioid from the second fraction of modified release multiple-units relative to the in vitro release of the first fraction of the opioid, as measured by said dissolution method, the fast release and the delayed in vitro release being adapted so that the first fraction is substantially released when the release from the second fraction is initiated corresponding to at least 50% release of the opioid contained in the first fraction at the time when 10% of the opioid contained in the second fraction is released as measured by said dissolution method, the ratio between the first and the second fraction of modified release multiple-units in the composition being in the range of 1:20–1:2 calculated on the weight of the fractions.

2. A composition according to claim 1, wherein the in vitro dissolution characteristics of the first fraction of modified release multiple-units provides within 0.5 hours a release as defined by said dissolution method of at least 30% of the opioid.

3. A composition according to claim 1, wherein the in vitro dissolution characteristics of the first fraction of modified release multiple-units provides within 0.5 hour a release as defined by said dissolution method of at least 40% of the opioid.

4. A composition according to claim 1, wherein the in vitro dissolution characteristics of the first fraction of modified release multiple-units provides within 0.5 hour a release as defined by said dissolution method of at least 50% of the opioid.

5. A composition according to claim 1, wherein the in vitro dissolution characteristics of the first fraction of modified release multiple-units provides within 0.5 hour a release as defined by said dissolution method of at least 60% of the opioid.

6. A composition according to claim 1, wherein the in vitro dissolution characteristics of the first fraction of modified release multiple-units provides within 0.5 hour a release as defined by said dissolution method of at least 70% of the opioid.

7. A composition according to claim 1, wherein the in vitro dissolution characteristics of the first fraction of modified release multiple-units provides within 0.5 hour a release as defined by said dissolution method of at least 90% of the opioid.

8. A composition according to claim 1, wherein the in vitro dissolution characteristics of the first fraction of modified release multiple-units provides within 1 hour a release as defined by said dissolution method of at least 50% of the opioid.

9. A composition according to claim 1, wherein the in vitro dissolution characteristics of the first fraction of modified release multiple-units provides within 1 hour a release as defined by said dissolution method of at least 60% of the opioid.

10. A composition according to claim 1, wherein the in vitro dissolution characteristics of the first fraction of modified release multiple-units provides within 1 hour a release as defined by said dissolution method of at least 70% of the opioid.

11. A composition according to claim 1, wherein the in vitro dissolution characteristics of the first fraction of modified release multiple-units provides within 1 hour a release as defined by said dissolution method of at least 80% of the opioid.

12. A composition according to claim 1, wherein the in vitro dissolution characteristics of the first fraction of modified release multiple-units provides within 1 hour a release as defined by said dissolution method of at least 90% of the opioid.

13. A composition according to claim 1, wherein the in vitro dissolution characteristics of the first fraction of modified release multiple-units provides within 1 hour a release as defined by said dissolution method of at least 95% of the opioid.

14. A composition according to claim 1, wherein the in vitro dissolution characteristics of the second fraction of modified release multiple-units provides within 1 hour a release as defined by said dissolution method in the range of 0%–30% of the opioid.

15. A composition according to claim 1, wherein the in vitro dissolution characteristics of the second fraction of modified release multiple-units provides within 1 hour a release as defined by said dissolution method in the range of 0%–10% of the opioid.

16. A composition according to claim 1, wherein the in vitro dissolution characteristics of the second fraction of modified release multiple-units provides within 1 hour a release as defined by said dissolution method of about 5% of the opioid.

17. A composition according to claim 1, wherein the in vitro dissolution characteristics of the second fraction of modified release multiple-units provides within 3 hours a release as defined by said dissolution method in the range of 10%–70% of the opioid.

18. A composition according to claim 1, wherein the in vitro dissolution characteristics of the second fraction of modified release multiple-units provides within 3 hours a release as defined by said dissolution method in the range of 15%–60% of the opioid.

19. A composition according to claim 1, wherein the in vitro dissolution characteristics of the second fraction of modified release multiple-units provides within 3 hours a release as defined by said dissolution method in the range of 20%–50% of the opioid.

20. A composition according to claim 1, wherein the in vitro dissolution characteristics of the second fraction of modified release multiple-units provides within 3 hours a release as defined by said dissolution method in the range of 25%–45% of the opioid.

21. A composition according to claim 1, wherein the in vitro dissolution characteristics of the second fraction of modified release multiple-units provides within 3 hours a release as defined by said dissolution method of about 35% of the opioid.

22. A composition according to claim 1, wherein the in vitro dissolution characteristics of the second fraction of modified release multiple-units provides within 6 hours a release as defined by said dissolution method in the range of 35%–95% of the opioid.

23. A composition according to claim 1, wherein the in vitro dissolution characteristics of the second fraction of modified release multiple-units provides within 6 hours a release as defined by said dissolution method in the range of 50%–90% of the opioid.

24. A composition according to claim 1, wherein the in vitro dissolution characteristics of the second fraction of modified release multiple-units provides within 6 hours a release as defined by said dissolution method in the range of 60%–80% of the opioid.

25. A composition according to claim 1, wherein the in vitro dissolution characteristics of the second fraction of modified release multiple-units provides within 6 hours a release as defined by said dissolution method in the range of 65%–75% of the opioid.

26. A composition according to claim 1, wherein the in vitro dissolution characteristics of the second fraction of modified release multiple-units provides within 6 hours a release as defined by said dissolution method in the range of about 70% of the opioid.

27. A composition according to claim 1, wherein the in vitro dissolution characteristics of the second fraction of modified release multiple-units provides within 9 hours a release as defined by said dissolution method in the range of 50%–100% of the opioid.

28. A composition according to claim 1, wherein the in vitro dissolution characteristics of the second fraction of modified release multiple-units provides within 9 hours a release as defined by said dissolution method in the range of 60%–98% of the opioid.

29. A composition according to claim 1, wherein the in vitro dissolution characteristics of the second fraction of modified release multiple-units provides within 9 hours a release as defined by said dissolution method in the range of 70%–95% of the opioid.

30. A composition according to claim 1, wherein the in vitro dissolution characteristics of the second fraction of modified release multiple-units provides within 9 hours a release as defined by said dissolution method in the range of 80%–90% of the opioid.

31. A composition according to claim 1, wherein the in vitro dissolution characteristics of the second fraction of modified release multiple-units provides within 9 hours a release as defined by said dissolution method of about 85% of the opioid.

32. A composition according to claim 1, wherein the in vitro dissolution characteristics of the first and second fractions are adapted so that the first fraction is substantially released when the release from the second fraction is initiated corresponding to at least 50% release of the first fraction at the time 5% of the second fraction is released as measured by said dissolution method.

33. A composition according to claim 1, wherein the in vitro dissolution characteristics of the first and second fractions are adapted so that the first fraction is substantially released when the release from the second fraction is initiated corresponding to at least 70% release of the first fraction at the time 10% of the second fraction is released as measured by said dissolution method.

34. A composition according to claim 1, wherein the in vitro dissolution characteristics of the composition provides within 1 hour a release of the opioid in the first and second fractions in the range of 5%–50% as defined by said dissolution method.

35. A composition according to claim 1, wherein the in vitro dissolution characteristics of the composition provides within 1 hour a release of the opioid in the first and second fractions in the range of 5%–45% as defined by said dissolution method.

36. A composition according to claim 1, wherein the in vitro dissolution characteristics of the composition provides within 1 hour a release of the opioid in the first and second fractions in the range of 15%–40% as defined by said dissolution method.

37. A composition according to claim 1, wherein the in vitro dissolution characteristics of the composition provides within 1 hour a release of the opioid in the first and second fractions in the range of 20–35% as defined by said dissolution method.

38. A composition according to claim 1, wherein the in vitro dissolution characteristics of the composition provides within 1 hour a release of the opioid in the first and second fractions of about 27% as defined by said dissolution method.

39. A composition according to claim 1, wherein the in vitro dissolution characteristics of the composition provides within 3 hours a release as defined by said dissolution method in the range of 20%–80% of the opioid.

40. A composition according to claim 1, wherein the in vitro dissolution characteristics of the composition provides within 3 hours a release as defined by said dissolution method in the range of 25%–70% of the opioid.

41. A composition according to claim 1, wherein the in vitro dissolution characteristics of the composition provides within 3 hours a release as defined by said dissolution method in the range of 30%–60% of the opioid.

42. A composition according to claim 1, wherein the in vitro dissolution characteristics of the composition provides within 3 hours a release as defined by said dissolution method in the range of 35%–55% of the opioid.

43. A composition according to claim 1, wherein the in vitro dissolution characteristics of the composition provides within 3 hours a release as defined by said dissolution method of about 50% of the opioid.

44. A composition according to claim 1, wherein the in vitro dissolution characteristics of the composition provides within 6 hours a release as defined by said dissolution method in the range of 40%–98% of the opioid.

45. A composition according to claim 1, wherein the in vitro dissolution characteristics of the composition provides within 6 hours a release as defined by said dissolution method in the range of 50%–95% of the opioid.

46. A composition according to claim 1, wherein the in vitro dissolution characteristics of the composition provides within 6 hours a release as defined by said dissolution method in the range of 60%–90% of the opioid.

47. A composition according to claim 1, wherein the in vitro dissolution characteristics of the composition provides within 6 hours a release as defined by said dissolution method in the range of 65%–85% of the opioid.

48. A composition according to claim 1, wherein the in vitro dissolution characteristics of the composition provides within 6 hours a release as defined by said dissolution method in the range of 70%–83% of the opioid.

49. A composition according to claim 1, wherein the in vitro dissolution characteristics of the composition provides within 6 hours a release as defined by said dissolution method of about 80% of the opioid.

50. A composition according to claim 1, wherein the in vitro dissolution characteristics of the composition provides within 9 hours a release as defined by said dissolution method in the range of 50%–100% of the opioid.

51. A composition according to claim 1, wherein the in vitro dissolution characteristics of the composition provides within 9 hours a release as defined by said dissolution method in the range of 60%–90% of the opioid.

52. A composition according to claim 1, wherein the in vitro dissolution characteristics of the composition provides within 9 hours a release as defined by said dissolution method in the range of 75%–97% of the opioid.

53. A composition according to claim 1, wherein the in vitro dissolution characteristics of the composition provides within 9 hours a release as defined by said dissolution method in the range of 80%–96% of the opioid.

54. A composition according to claim 1, wherein the in vitro dissolution characteristics of the composition provides within 9 hours a release as defined by said dissolution method in the range of 85%–96% of the opioid.

55. A composition according to claim 1, wherein the in vitro dissolution characteristics of the composition provides within 9 hours a release as defined by said dissolution method of about 95% of the opioid.

56. A composition according to claim 1, wherein the ratio between the first and second fraction of modified release multiple-units in the composition is in the range of 1:10–1:3 calculated on the weight of the fractions.

57. A composition according to claim 1, wherein the ratio between the first and the second fraction of modified release multiple-units in the composition is in the range of 1:8–1:3 calculated on the weight of the fractions.

58. A composition according to claim 1, wherein the ratio between the first and the second fraction of modified release multiple-units in the composition is in the range of 1:7–1:3.5 calculated on the weight of the fractions.

59. A composition according to claim 1, wherein the ratio between the first and the second fraction of modified release multiple-units in the composition is in the range of 1:3.5–1:4.5 calculated on the weight of the fractions.

60. A composition according to claim 1, wherein the ratio between the first and the second fraction of modified release multiple-units in the composition is in the range of 1:4 calculated on the weight of the fractions.

61. A composition according to claim 1, wherein the multiple-units are coated cross-sectionally substantially homogeneous pellets.

62. A composition according to claim 1, wherein the individual units of the first fraction are of substantially the same size and weight as the individual units of the second fraction.

63. A composition according to claim 1, wherein the first fraction results in a peak plasma concentration of opioid which is substantially the same as the peak plasma concentration resulting from the second fraction.

64. A composition according to claim 1, wherein the first fraction results in a peak plasma concentration of opioid which is higher than the peak plasma concentration resulting from the second fraction.

65. A composition according to claim 1, wherein the first fraction results in a peak plasma concentration of opioid which is lower than the peak plasma concentration resulting from the second fraction.

66. A composition according to claim 1, wherein the first fraction results in a therapeutically active plasma concentration of opioid until the delayed release of an opioid from the second fraction of modified release multiple-units contributes to the maintenance of a therapeutically active plasma concentration of opioid.

67. A composition according to claim 1, wherein the modified release coating of each fraction comprises substantially the same coating components.

68. A composition according to claim 1, wherein the amount of modified release coating of the first fraction calculated on the dry weight of the coating is present in a range corresponding to about 10% to about 80% calculated on the dry weight of the amount of the modified release coating of the second fraction.

69. A composition according to claim 1, wherein the modified release coating of the fractions are substantially water-insoluble, but water-diffusible and substantially pH-independent.

70. A composition according to claim 1, wherein a unit dosage of the composition comprises about 10 mg of the opioid.

71. A composition according to claim 1, wherein a unit dosage of the composition comprises about 20 mg of the opioid.

72. A composition according to claim 1, wherein a unit dosage of the composition comprises about 30 mg of the opioid.

73. A composition according to claim 1, wherein a unit dosage of the composition comprises about 50 mg of the opioid.

74. A composition according to claim 1, wherein a unit dosage of the composition comprises about 60 mg of the opioid.

75. A composition according to claim 1, wherein a unit dosage of the composition comprises about 100 mg of the opioid.

76. A composition according to claim 1, comprising a unit dosage for the administration of the analgesically effective amount of the opioid twice daily.

77. A composition according to claim 1 comprising a unit dosage for the administration of the analgesically effective amount of the opioid once daily.

78. A composition according to claim 1, wherein the unit dosage of the composition is in the form of a capsule.

79. A composition according to claim 1, wherein the opioid is morphine or a pharmaceutically acceptable salt thereof.

80. A composition according to claim 1, wherein the opioid is morphine sulphate.

81. A composition according to claim 1, wherein the opioid is tramadol or a pharmaceutically acceptable salt thereof.

82. A process for the preparation of a unit dosage of an oral pharmaceutical modified release multiple-units composition according to claim 1, the process comprising incorporating into the unit dosage at least two fractions of coated multiple-units as follows:

a first fraction of modified release coated multiple-units for relatively fast release in vivo of an opioid to obtain a therapeutically active plasma concentration within a relatively short period of time, and a second fraction of modified release coated multiple-units for delayed release in vivo of an opioid to maintain an analgesically active plasma concentration for a period of at least 12 hours, the formulation of the first and the second fractions, with respect to modified release therefrom and with respect to the ratio between the first and the second fraction in the unit dosage, being adapted so as to obtain:

i) a relative fast in vitro release of the opioid from the first fraction of modified release multiple-units, as measured by said dissolution method, the ratio between the first and the second fraction of modified release multiple-units in the composition being in the range of 1:20–1:2 calculated on the weight of the fractions, ii) a delayed in vitro release of the opioid from the second fraction of modified release multiple-units relative to the in vitro release of the first fraction of the opioid, as measured by said dissolution method, the fast release and the delayed in vitro release being adapted so that the first fraction is substantially released when the release from the second fraction is initiated corresponding to at least 50% release of the opioid contained in the first fraction at the time when 10% of the opioid contained in the second fraction is released as measured by said dissolution method.

* * * * *

UNITED STATES PATENT AND TRADEMARK OFFICE
CERTIFICATE OF CORRECTION

PATENT NO. : 6,159,501
DATED : December 12, 2000
INVENTOR(S) : Annette Skinhoj

It is certified that error appears in the above-identified patent and that said Letters Patent is hereby corrected as shown below:

Column 15,
Line 5, "Ming Tal" should read -- Ming Tai --.
Line 22, "Polyplasdone° XL" should read -- Polyplasdone® XL --.

Column 31,
Table 13, "Hydropropylmethylcellulose" should read -- Hydroxypropylmethylcellulose --.

Column 33,
Line 5, "tale" should read -- talc --.

Column 44,
Line 3, "tale" should read -- talc --.

Column 51,
Line 16, "..a pulse oximeter were placed" should read -- ..a pulse oximeter was placed. --.

Column 55,
Line 15, "EDM treatment" should read -- RDM treatment --.

Column 56,
Line 22, "proffie" should read -- profile --.

Signed and Sealed this

Twelfth Day of March, 2002

*Attest:*

JAMES E. ROGAN
*Attesting Officer*     *Director of the United States Patent and Trademark Office*